United States Patent
Lee et al.

(10) Patent No.: US 12,139,733 B2
(45) Date of Patent: Nov. 12, 2024

(54) ORNITHINE DECARBOXYLASE VARIANT AND METHOD FOR PRODUCING PUTRESCINE BY USING SAME

(71) Applicant: CJ CHEILJEDANG CORPORATION, Seoul (KR)

(72) Inventors: Jaehun Lee, Seoul (KR); Hee-See Moon, Seoul (KR); Ae Ji Jeon, Seoul (KR); Young Lyeol Yang, Seoul (KR); Byung-Gee Kim, Seoul (KR); Eun Young Hong, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 1008 days.

(21) Appl. No.: 17/044,726

(22) PCT Filed: Dec. 24, 2019

(86) PCT No.: PCT/KR2019/018404
§ 371 (c)(1),
(2) Date: Oct. 1, 2020

(87) PCT Pub. No.: WO2020/138919
PCT Pub. Date: Jul. 2, 2020

(65) Prior Publication Data
US 2023/0287382 A1    Sep. 14, 2023

(30) Foreign Application Priority Data

Dec. 27, 2018  (WO) ............... PCT/KR2018/016764
Dec. 28, 2018  (TW) .................................. 107147749

(51) Int. Cl.
*C12N 9/88*    (2006.01)
*C12P 13/00*   (2006.01)

(52) U.S. Cl.
CPC .............. *C12N 9/88* (2013.01); *C12P 13/001* (2013.01); *C12Y 401/01017* (2013.01)

(58) Field of Classification Search
CPC .......... C12N 9/88; C12P 13/001; C12P 13/00; C12Y 401/01017; C12Y 401/01018
See application file for complete search history.

(56) References Cited

U.S. PATENT DOCUMENTS 9,234,205 B2    1/2016  Hatzfeld
2007/0118916 A1*  5/2007  Puzio ................. C12N 15/8243
                                                  800/278
(Continued)

FOREIGN PATENT DOCUMENTS

EP    2281880 A2    2/2011
EP    3181690 A1    6/2017
(Continued)

OTHER PUBLICATIONS

Hong et al., Rational engineering of ornithine decarboxylase with greater selectivity for ornithine over lysine through protein network analysis, Journal of Biotechnology, vol. 281, p. 175-182, 2018. (Year: 2018).*

(Continued)

*Primary Examiner* — Soren Harward
*Assistant Examiner* — Naghmeh Nina Moazzami
(74) *Attorney, Agent, or Firm* — Christensen, Fonder, Dardi PLLC; Diane E. Bennett; Peter S. Dardi

(57) ABSTRACT

The present application relates to a variant of ornithine decarboxylase or protein, a polynucleotide encoding the same, a microorganism containing the same, and a method for producing putrescine using the same.
The present invention achieves effects of increasing putrescine productivity, production efficiency or production selec- (Continued)

tivity, suppressing side reactions, and saving the cost involved in purifying putrescine.

17 Claims, 5 Drawing Sheets

Specification includes a Sequence Listing.

(56) References Cited

U.S. PATENT DOCUMENTS

| | | |
|---|---|---|
| 2014/0004577 A1 | 1/2014 | Choi et al. |
| 2014/0363859 A1 | 12/2014 | Lee et al. |
| 2016/0168605 A1 | 6/2016 | Choi et al. |
| 2017/0314007 A1 | 11/2017 | Liu |
| 2018/0170960 A1 | 6/2018 | Asano et al. |
| 2020/0208182 A1 | 6/2020 | Kim et al. |

FOREIGN PATENT DOCUMENTS

| | | |
|---|---|---|
| JP | 2014-500728 A2 | 1/2014 |
| JP | 2016-524919 A | 8/2016 |
| KR | 10-2009-0107920 A | 10/2009 |
| KR | 10-2015-0009890 A | 1/2015 |
| KR | 10-2018-0136612 A | 12/2018 |
| KR | 10-2019-0002239 A | 1/2019 |
| WO | 2009-125924 A2 | 10/2009 |
| WO | 2016-199898 A1 | 3/2018 |

OTHER PUBLICATIONS

Jonson et al., A critical view on conservative mutations, 2001, Protein Engin. Design & Sel., vol. 14, Iss 6, p. 397-402 (Year: 2001).*

H95306, PIR database, 2001. (Year: 2001).*

Office Action from corresponding Japanese Patent Application No. 2019-233558 dated Aug. 9, 2022. (Google trans).

GenBank AAA64830.1, "ornithine decarboxylase [*Lactobacillus* sp.]", Oct. 8, 1994.

Hackert et al., "Sequence of Ornithine Decarboxylase from *Lactobacillus* sp. Strain 30a", Journal of Bacteriology, p. 7391-7394, (Dec. 1994).

Hong et al., "Rational engineering of ornithine decarboxylase with greater selectivity for ornithine over lysine through protein network analysis", Journal of Biotechnology, vol. 281, p. 175-182, (2018).

International Search Report and Written Opinion for Patent Application No. PCT/KR2019/018404 dated May 1, 2020.

International Search Report and Written Opinion for Patent Application No. PCT/KR2018/016764 dated Sep. 24, 2019.

* cited by examiner

FIG. 4

| Variant | Ornithine[a] | | | Lysine[b] | | |
|---|---|---|---|---|---|---|
| | $K_M$(mM) | $k_{cat}$(s$^{-1}$) | $k_{cat}/K_M$(s$^{-1}$mM$^{-1}$) | $K_M$(mM) | $k_{cat}$(s$^{-1}$) | $k_{cat}/K_M$(s$^{-1}$mM$^{-1}$) |
| Wild type | 0.65 ± 0.09 | 39.1 ± 1.22 | 60.5 | 26.7 ± 3.04 | 2.04 ± 0.06 | 0.077 |
| E898D | 0.96 ± 0.05 | 32.2 ± 0.48 | 33.4 | 16.5 ± 2.34 | 0.98 ± 0.03 | 0.060 |
| A713L | 0.64 ± 0.07 | 39.7 ± 1.07 | 61.5 | 23.8 ± 3.17 | 0.95 ± 0.03 | 0.040 |
| E898D/A713L | 0.64 ± 0.07 | 26.0 ± 0.62 | 40.6 | 16.9 ± 3.53 | 0.79 ± 0.05 | 0.046 |

ORNITHINE DECARBOXYLASE VARIANT AND METHOD FOR PRODUCING PUTRESCINE BY USING SAME

CROSS REFERENCE TO RELATED APPLICATIONS

This application is a National Stage filing of PCT Application No. PCT/KR2019/018404 filed Dec. 24, 2019, entitled "Ornithine Decarboxylase Variant and Method For Producing Putrescine By Using Same", which claims priority to PCT Application No. PCT/KR2018/016764 filed Dec. 27, 2018, and to Taiwan Patent Application No. 107147749 filed Dec. 28, 2018, all of which are incorporated herein by reference.

TECHNICAL FIELD

The present application relates to a variant of ornithine decarboxylase, a gene encoding the variant of ornithine decarboxylase, a microorganism containing the variant of ornithine decarboxylase, and a synthesis of putrescine using the same.

The present application claims the benefit of priorities based on International Patent Application No. PCT/KR2018/016764 filed on Dec. 27, 2018 and Taiwan Patent Application No. 107147749 filed on Dec. 28, 2018, and all the contents disclosed in these patent applications is included as a part of the specification of the present application.

BACKGROUND TECHNOLOGY

Putrescine (1,4-diamino-butane) is a substance that causes odors from decayed organisms, but is industrially produced in that it can be used for a synthesis of 4,6-nylon. Currently, the putrescine is produced in more than 10,000 tons per year by petroleum resources, but has a problem that the supply and demand of raw materials is unstable due to frequent fluctuations in oil prices. Further, there is a problem that the putrescine may cause environmental pollution due to a large amount of toxic substances generated in the production process.

In order to solve these problems, researches on bio-derived putrescine synthesis have been actively conducted. For example, the researches have been conducted on a method for synthesizing putrescine from bio-derived ornithine or producing large quantities of putrescine from microorganisms using a sugar.

In the method for producing putrescine from the microorganisms, various biological engineering methods have been used to increase the putrescine production. The methods may include, for example, regulating the activity of an enzyme involved in putrescine biosynthesis with a promoter, overexpressing a reverse transporter so that putrescine is easily released out of a cell, or blocking a pathway that decomposes putrescine. Among them, it is known that the method of regulating the activity of the enzyme involved in the putrescine biosynthesis within microorganisms can greatly contribute to an increase in the putrescine production.

Ornithine decarboxylase is an enzyme that synthesizes putrescine by cutting a terminal carboxyl group of ornithine, and is one of the enzymes that play an important role in the putrescine biosynthesis. However, since the ornithine decarboxylase not only synthesizes putrescine from ornithine, but also has the activity (side reaction) of synthesizing from lysine to cadaverine (1,5-diamino-pentane), when the activity becomes higher, the cadaverine may be produced together with putrescine, thereby lowering the putrescine production. The cadaverine may also cause a number of problems even when putrescine is purified. Specifically, in the process of purifying a microbial culture solution by distillation, the structure of putrescine ($H_2N(CH_2)_4NH_2$) and cadaverine ($H_2N(CH_2)_5NH_2$) is very similar, and thus, it is expensive and time consuming to selectively purify putrescine.

Therefore, in order to regulate the activity of ornithine decarboxylase, it is very important to decrease the activity (side reaction) of synthesizing from lysine to cadaverine while maintaining the activity of synthesizing putrescine from ornithine.

Thus, the present inventors discovered a novel ornithine decarboxylase, and completed the invention by confirming that the ornithine decarboxylase lowers the activity of synthesizing cadaverine and increases the activity of synthesizing putrescine.

DETAILED DESCRIPTION OF THE INVENTION

Technical Tasks

The present application provides an ornithine decarboxylase or a variant thereof.

The present application also provides a polynucleotide encoding the ornithine decarboxylase or the variant thereof.

The present application is to provide a microorganism that produces putrescine, containing the ornithine decarboxylase or the variant thereof.

Another object of the present application is to provide a method for producing putrescine, comprising culturing the microorganism in a medium.

Another object of the present application is to provide a method for increasing a purity of putrescine, comprising culturing the microorganism in the medium.

Another object of the present application is to provide a method for increasing a ratio of putrescine to cadaverine, comprising culturing the microorganism in the medium.

Furthermore, another object of the present application is to provide a use of putrescine for synthesizing a polyamide-based polymer.

Technical Solution

The detailed description on the above is as follows. Meanwhile, each explanation and embodiment disclosed in the present application may be applied to each other explanation and embodiment. That is, all combinations of the various elements disclosed in the present application fall within the scope of the present application. Further, the scope of the present application is not considered to be limited by the specific explanations described below.

An aspect of the present application provides a variant of ornithine decarboxylase having putrescine production activity, which comprises one or more amino acid substitutions in the amino acid sequence of SEQ ID NO. 1.

Specifically, the present application provides a variant of a protein in which i) alanine, the 713th amino acid, is substituted with another amino acid and/or ii) glutamic acid, the 698th amino acid, is substituted with another amino acid, in the amino acid sequence of SEQ ID NO. 1. The substitution of the amino acid may include those that i) alanine, the 713th amino acid, is substituted with an amino acid selected from leucine, isoleucine, valine, arginine, aspartic acid, tryptophan and glutamine, and/or ii) glutamic acid, the 698th amino acid, is substituted with aspartic acid.

The term "putrescine" in this application is a substance produced by decarboxylation of ornithine or hydrolysis of agmatine, which is also present in a decayed material, but is widely distributed as a normal component in a living body. It is a kind of polyamine that composes ribosome and promotes cell growth or RNA synthesis. In particular, industrially, it is an important raw material for the production of polyamide 4 and 6, including nylon 4 and 6, and is a material that continuously require a research for mass production.

Putrescine may be produced by using ornithine as a substrate. Further, putrescine may be produced by synthesizing ornithine using a substance that is a precursor of ornithine as the substrate. The synthesis of ornithine can be applied without limitation as long as it can be easily selected by those skilled in the art.

The term "ornithine" in this application is a basic amino acid that plays an important role in the ornithine cycle, and especially, L-ornithine is widely found in plants, animals and microorganisms. In general, the ornithine plays a metabolically important role in relation to urea production in a living body having the ornithine cycle. Further, it can be converted to each other with arginine, glutamic acid, and proline in the living body, and carries ketone acid, glyoxalic acid, and amino group. It is synthesized to a polyamine through a substrate that produces amine (putrescine) by the ornithine decarboxylase. In the present invention, particularly, it may be L-ornithine which can be used as a substrate of the ornithine decarboxylase.

The term "ornithine decarboxylase (ODC)" in this application is an enzyme that catalyzes the following reaction formula, which is the first step for synthesizing polyamine and the final step in a pathway that produces the putrescine. In this application, the ornithine decarboxylase may be used interchangeably with ornithine decarbonation enzyme. The ODC produces putrescine using L-ornithine as a substrate, and act as a co-factor of pyridoxal phosphate (PLP).

L-ornithine<=>putrescine+CO$_2$ [Reaction formula]

FIG. 1 shows a chemical reaction formula of the process for synthesizing putrescine with ornithine as a substrate using the ornithine decarboxylase. A cadaverine synthesis pathway, which is a side reaction of the ornithine decarboxylase to be suppressed, is also shown.

In the present application, various methods well known in the art may be applied to the method for securing the ornithine decarboxylase (ODC). Examples of such methods may include a gene synthesis technology comprising codon optimization to ensure high efficiency of enzymes in microorganisms that are widely used for enzyme expression, and a method for screening useful enzymatic resources by bioinformatics based on mass genome information of microorganisms, but is not limited thereto.

In the present application, SEQ ID NO. 1 refers to an amino acid sequence of the ornithine decarboxylase having putrescine production activity. The amino acid sequence of SEQ ID NO. 1 can be obtained from GenBank of NCBI which is a known database. As an example, the ornithine decarboxylase may be derived from *Lactobacillus* sp., *Saccharomyces* sp., or *Escherichia coli* (*E. coli*), and in particular, derived from *Lactobacillus saerimneri*. However, the ornithine decarboxylase is not limited thereto and may be used without any limitation as long as it is the amino acid sequence of a protein having the same activity as the protein containing the amino acid sequence. In addition, although the protein containing the amino acid sequence of SEQ ID NO. 1 is described as the ornithine decarboxylase having the putrescine production activity in the present application, it does not exclude proteins which can add meaningless sequences before and after the amino acid sequence of SEQ ID NO. 1, or a mutation or a silent mutation thereof which can naturally occur. It is apparent to those skilled in the art that a protein having the same or corresponding activity as the protein containing the amino acid sequence of SEQ ID NO. 1 is included in the protein having the putrescine activity of the present application. For a specific example, the protein having the putrescine production activity of the present application may have the amino acid sequence of SEQ ID NO. 1, or a protein consisting of an amino acid sequence with homology or identity of at least 80%, 85%, 90%, 95%, 96%, 97%, 98%, or 99% to the amino acid sequence of SEQ ID NO. 1. Further, It is obvious that the amino acid sequences having such homology or identity and exhibiting an efficacy corresponding to the above protein are included within the scope of the protein subject to variation of the present application regardless of whether some of the sequences are deleted, modified, substituted, or added.

That is, even though 'a protein or a polypeptide having an amino acid sequence listed by a specific sequence number', 'a protein or a polypeptide comprising an amino acid sequence listed by a specific sequence number' are described in the present application, it is apparent that a protein having the same or corresponding activity as a polypeptide consisting of the amino acid sequences of the corresponding sequence number can be also used in the present application regardless of whether some of the sequences are deleted, modified, substituted, or added. For example, it is obvious that if a polypeptide consists of a sequence corresponding to SEQ ID NO. 1 or having the same or corresponding activity as the sequence, the polypeptide can belong to the 'polypeptide consisting of the amino acid sequence of SEQ ID NO. 1'. For example, it is obvious that in case of having the same or corresponding activity as the variant protein, addition of a sequence that does not change the function of the protein before and after the amino acid sequence, a naturally occurring mutation, a silent mutation thereof or a conservative substitution is not excluded and a protein having such sequence addition or mutation is also within the scope of the present application.

The term "conservative substitution" in this application means substitution of one amino acid with another amino acid having similar structural and/or chemical properties. Such a variant can still have one or more biological activities, but, for example, have one or more conservative substitutions. Such amino acid substitutions can generally occur based on the similarity in polarity, charge, solubility, hydrophobicity, hydrophilicity and/or amphipathic nature of residues. For example, positively charged (basic) amino acids among the amino acids with electrically charged side chains include arginine, lysine, and histidine; negatively charged (acidic) amino acids include glutamic acid and aspartic acid; nonpolar amino acids among the amino acids having uncharged side chains include glycine, alanine, valine, leucine, isoleucine, methionine, phenylalanine, tryptophan and proline; polar or hydrophilic amino acids include serine, threonine, cysteine, tyrosine, asparagine, and glutamine; and, aromatic amino acids among the nonpolar amino acids include phenylalanine, tryptophan, and tyrosine.

As used herein, the term "variant" refers to a protein that one or more amino acids are different from the sequences mentioned above in conservative substitution and/or modification, but maintain function or property of the protein. The variant is different from the sequence identified by several numbers of amino acid substitutions, deletions or additions. Such variant can generally be identified by modifying one or more amino acids among the amino acid sequences of the protein and evaluating the properties of the modified protein. That is, an ability of the variant may be increased, unchanged, or decreased compared to a native protein. Further, some variants may include variants having one or more moieties removed, such as an N-terminal leader sequence or a transmembrane domain. Other variants may include variants having some moieties removed from a N- and/or C-terminal of a mature protein. The term "variant" may be used in the terminologies such as a modification, a modified protein, a modified polypeptide, a mutant, a mutein, a divergent, etc. If the term is used in a mutated sense, it is not limited the above. For the purposes of the present application, the variant may have an increased activity of the modified protein compared to a naturally wild or unmodified protein, but is not limited thereto.

Further, the variant may include deletion or addition of amino acids minimally affecting the properties and the secondary structure of a polypeptide. For example, the polypeptide may be conjugated with signal (or leader) sequences of the protein N-terminal involved in transfer of the protein co-translationally or post-translationally. In addition, the polypeptide may be conjugated with other sequences or linkers to identify, purify, or synthesize the polypeptide.

The protein variant in the present application may be a variant of ornithine decarboxylase. In the present application, the term "variant of ornithine decarboxylase" may be used interchangeably with 'variant ODC protein, ODC variant, variant ornithine decarbonation enzyme, variant ornithine decarboxylase, variant ODC enzyme protein, variant ODC enzyme, etc.'.

The above variant may be the one that one or more amino acids of the 713th and the 698th amino acids of the amino acid sequence of SEQ ID NO. 1 are substituted with an amino acid different from the amino acid before substitution.

The 'substitution with different amino acid' is not limited as long as it is an amino acid different from the amino acid before substitution. For example, alanine, the 713th amino acid of the amino acid sequence of SEQ ID NO. 1, may include the ones substituted with a hydrophobic amino acid, a basic amino acid, an acidic amino acid, a neutral amino acid, or an aromatic amino acid, other than alanine. That is, as long as alanine, the 713th amino acid in the amino acid sequence of SEQ ID NO. 1, is substituted with an amino acid residue other than alanine, or glutamic acid, the 698th amino acid sequence, is substituted with an amino acid residue other than glutamic acid, they are not limited the above. On the other hand, the expression 'a specific amino acid is substituted' in the present application is obviously meant to be substituted with an amino acid different from the amino acid before substitution, even if it is not separately indicated that the amino acid has been substituted with another amino acid.

Specifically, the above variant may be a variant in which i) alanine, the 713th amino acid, is substituted with other amino acid and/or ii) glutamic acid, the 698th amino acid, is substituted with other amino acid, in the amino acid sequence of SEQ ID NO. 1. Substitution with the other amino acid may include the ones that i) alanine, the 713th amino acid, is substituted with an amino acid selected from leucine, isoleucine, valine, arginine, aspartic acid, tryptophan and glutamine, and/or ii) glutamic acid, the 698th amino acid, is substituted with aspartic acid. More specifically, the variant may be a variant in which i) alanine, the 713th amino acid, is substituted with an amino acid selected from leucine, isoleucine, valine, arginine, aspartic acid, tryptophan and glutamine, and/or ii) glutamic acid, the 698th amino acid, is substituted with aspartic acid.

In the amino acid sequence of SEQ ID NO. 1, the variant that i) alanine, the 713th amino acid, is substituted with an amino acid selected from leucine, isoleucine, valine, arginine, aspartic acid, tryptophan and glutamine and/or ii) glutamic acid, the 698th amino acid, is substituted with aspartic acid may include any one of the amino acid sequences selected from SEQ ID NO. 4, SEQ ID NO. 8, SEQ ID NO. 9, and SEQ ID NOS. 19 to 23. Specifically, the variant may be essentially consisting of any one of the amino acid sequences of SEQ ID NO. 4, SEQ ID NO. 8, and SEQ ID NOS. 19 to 23. More specifically, the variant may be consisting of any one of the amino acid sequences of SEQ ID NO. 4, SEQ ID NO. 8, SEQ ID NO. 9, and SEQ ID NOS. 19 to 23. However, the variant is not limited thereto.

The variant may be substituted with other amino acid at the positions corresponding to the 713th position and/or the 698th position of SEQ ID NO. 1, and may have a sequence homology of at least 80%, 90%, 95%, 96% 97%, 98%, or 99% or more, and less than 100%, with the amino acid sequence of SEQ ID NO. 1, and may have putrescine production activity.

Further, the variant may include any one of the amino acid sequences of SEQ ID NO. 4, SEQ ID NO. 8, SEQ ID NO. 9, and SEQ ID NOS. 19 to 23 or amino acid sequences having homology or identity of 80% or more with the amino acid sequences, but is not limited thereto. Specifically, the variant of the present application may include a polypeptide having the homology or identity of at least 80%, 90%, 95%, 96%, 97%, 98%, or 99% with any one of the amino acid sequences of SEQ ID NO. 4, SEQ ID NO. 8, SEQ ID NO. 9, and SEQ ID NOS. 19 to 23. In addition, it is obvious that if amino acid sequences have such homology or identity and exhibit an efficacy corresponding to the protein, proteins having amino acid sequences in which some sequences are deleted, modified, substituted or added also belong to the scope of the present application in addition to the amino acids of 713th or 698th positions.

The term 'homology' or 'identity' in this application refers to a degree associated with two given amino acid sequences or base sequences and may be expressed as a percentage (%). The terms homology and identity can often be used each other interchangeably.

The sequence homology or identity of a conserved polynucleotide or polypeptide may be determined by a standard alignment algorithm, and used together with a default gap penalty established by the program currently utilized. Substantially, the homologous or identical sequences can generally hybridize at moderate or high stringent conditions along at least about 50%, 60%, 70%, 80% or 90% of the entire sequence or the sequence full-length. The hybridization also contemplates polynucleotides containing degenerate codons instead of codons in the polynucleotide.

Whether any two polynucleotide or polypeptide sequences have homology, similarity or identity, can, for example, be determined by using known computer algorithms such as the "FASTA" program that utilizes the default parameters as in Pearson et al (1988) [Proc. Natl. Acad. Sci. USA 85]: 2444. Alternatively, it can be determined by using the Needleman-Wunsch algorithm (Needleman and Wunsch, 1970, J. Mol. Biol. 48: 443-453), as performed in the Needleman program of the EMBOSS package (EMBOSS: The European Molecular Biology Open Software Suite, Rice et al., 2000, Trends Genet. 16: 276-277) (version 5.0.0 or later) (including GCG program package (Devereux, J., et al, Nucleic Acids Research 12: 387 (1984), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.] (1988) SIAM J Applied Math 48: 1073). For example, the homology, similarity or identity can be determined by using BLAST of National Center for Biotechnology Information Database, or ClustalW.

The homology, similarity or identity of the polynucleotide or polypeptide can, for example, be determined by comparing sequence information using a GAP computer program such as Needleman et al. (1970), J Mol Biol. 48: 443, as known in Smith and Waterman, Adv. Appl. Math (1981) 2: 482. In summary, the GAP program is defined as the total number of symbols in the shorter of the two sequences divided by the number of similar aligned symbols (i.e., nucleotides or amino acids). The default parameters for the GAP program may include (1) a binary comparison matrix (containing values of 1 for identity and 0 for non-identity), and a weighted comparison matrix (or EDNAFULL (EMBOSS version of NCBI NUC4.4) substitution matrix) of Gribskov et al (1986) Nucl. Acids Res. 14: 6745, as disclosed by Schwartz and Dayhoff, eds., Atlas Of Protein Sequence And Structure, National Biomedical Research Foundation, pp. 353-358 (1979); (2) a penalty of 3.0 for each gap and an additional penalty of 0.10 for each symbol in each gap (or gap open penalty of 10, gap extension penalty of 0.5); and (3) no penalty for end gap. Accordingly, as used herein, the term "homology" or "identity" shows relevance between the sequences.

Further, whether any two polynucleotide or polypeptide sequences have homology, similarity, or identity can be confirmed by comparing the sequences by Southern hybridization experiment under the defined stringent conditions, and the defined appropriate hybridization conditions belong to the scope of the relevant art and can be determined by methods well known to those skilled in the art (e.g., J. Sambrook et al., Molecular Cloning, A Laboratory Manual, 2nd Edition, Cold Spring Harbor Laboratory press, Cold Spring Harbor, New York, 1989; FM Ausubel et al., Current Protocols in Molecular Biology, John Wiley & Sons, Inc., New York).

In the present application, the term "variant of ornithine decarboxylase" may be interchangeably used with a variant polypeptide of ornithine decarboxylase, a variant of ornithine decarboxylase protein, a variant polypeptide of ornithine decarboxylase protein, a variant polypeptide of ornithine decarboxylase, a variant of ornithine decarboxylase, a variant of ornithine decarboxylase protein, a variant ornithine decarboxylase, a variant ornithine decarboxylase protein, etc having putrescine production capacity. In addition, the ornithine decarboxylase may be derived from *Lactobacillus* sp., *Saccharomyces* sp., or *Escherichia coli*(*E. coli*), but is not limited thereto.

The variant of ornithine decarboxylase may include variations at the 713th and/or the 698th positions in the amino acid sequence of SEQ ID NO. 1, and even if the amino acid sequence is added to or deleted from SEQ ID NO. 1, variants substituted with amino acids at the positions corresponding to the 713th and/or 698th amino acids from the N-terminal of SEQ ID NO. 1 are also included in the scope of the present application.

The term "corresponding to" described herein in relation to the position of the amino acid residue refers to an amino acid residue at a position listed in a protein or a peptide, or an amino acid residue similar to, identical to, or homologous to a residue listed in the protein or the peptide. As used herein, the expression "corresponding region" generally refers to similar position in a related protein a reference protein.

The variant of ornithine decarboxylase protein is the ones that the 713th and/or the 698th amino acid in the amino acid sequence of SEQ ID NO. 1 is substituted with other amino acid, and may include the amino acid sequence of SEQ ID NO. 1 or may be a variant ornithine decarboxylase protein having enhanced activity compared to a ornithine decarboxylase before mutation, derived from a wild type microorganism. This variant of ornithine decarboxylase protein means that the amino acid at the position corresponding to the 713th or 698th of SEQ ID NO. 1 is mutated in the amino acid having homology or identity of at least 80%, 85%, 90%, 95%, 96%, 97%, 98%, or 99% or more with the amino acid sequence of SEQ ID NO. 1 described above.

The mutation of the 713th and/or the 698th amino acid may be i) substitution of alanine, the 713th amino acid, with leucine, isoleucine, valine, arginine, aspartic acid, tryptophan or glutamine, and/or ii) substitution of glutamic acid, the 698th amino acid, with aspartic acid.

Specifically, the variant of ornithine decarboxylase may be the ones that i) alanine, the 713th amino acid, is substituted with leucine, isoleucine, valine, arginine, aspartic acid, tryptophan or glutamine and/or ii) glutamic acid, the 698th amino acid, is substituted with aspartic acid, in the amino acid sequence of SEQ ID NO. 1, and may have enhanced activity compared to a protein containing the amino acid sequence of SEQ ID NO. 1 or an ornithine decarboxylase protein before mutation derived from a wild type microorganism.

For the purpose of the present application, a microorganism containing the variant of ornithine decarboxylase protein is characterized by increasing an amount of putrescine, a purity of putrescine, or a selectivity of putrescine production. The protein variant of the present application is characterized by having a gene regulatory activity such that the putrescine production capacity, the putrescine purity or the selectivity of putrescine production is increased compared to a naturally wild or non-mutated ornithine decarboxylase. In particular, it is significant that the microorganisms introduced with protein variant of the present application can inhibit the synthesis of cadaverine, one of the side reactions of ornithine decarboxylase and increase an amount of putrescine production.

Another aspect of the present application provides a polynucleotide encoding the variant of ornithine decarboxylase protein.

The ornithine decarboxylase protein comprising the amino acid sequence of SEQ ID NO. 1 and the variant thereof are as described above.

As used herein, the term "polynucleotide" means DNA or RNA strands of a certain length or more as a polymer of nucleotide in which a nucleotide monomer is long chained by a covalent bond, and more specifically, refers to polynucleotide fragments encoding the above variant.

The polynucleotide encoding the variant of ornithine decarboxylase of the present application may be included without limitation as long as it is a polynucleotide sequence encoding a variant polypeptide which has putrescine production activity of the present application. The gene encoding the amino acid sequence of ornithine decarboxylase protein in the present application may be, for example, a speC, odc, spe1 or speF gene, and the gene may be derived from *Lactobacillus* sp., *Saccharomyces* sp., or *Escherichia coli* (*E. coli*), but is not limited thereto. In addition, the gene may be a base sequence encoding any one of the amino acid sequence of SEQ ID NO. 1, SEQ ID NO. 4, SEQ ID NO. 8, SEQ ID NO. 9, SEQ ID NOS. 19 to 23, and more specifically, may be a sequence comprising any one of the base sequences of SEQ ID NO. 10, SEQ ID. No. 13, SEQ ID NO. 17, SEQ ID NO. 18, and SEQ ID NOS. 24 to 28, but is not limited thereto.

Specifically, the polynucleotide of the present application can make various modifications in the coding region within the scope that does not change the amino acid sequence of the polypeptide, due to degeneracy of the codon or considering the preferred codon in an organism that wants to express the polypeptide. Specifically, the polynucleotide sequence encoding the variant of ornithine decarboxylase protein in which the 713th and/or the 698th amino acids in the amino acid sequence of SEQ ID NO. 1 are substituted with other amino acids can be included without any limitation.

Further, if probes that can be prepared from known gene sequences, for example, the 713th and/or the 698th amino acids in the amino acid sequence of SEQ ID NO. 1 are sequences encoding the ornithine decarboxylase protein having the putrescine production activity substituted with other amino acid by hybridizing with complementary sequences to all or part of the base sequence under a stringent condition, they may be included without any limitation. The term "stringent condition" refers to a condition that enables specific hybridization between the polynucleotides. This condition is concretely described in the literature (e.g., J. Sambrook et al., Homology). The stringent condition may include a condition that genes having higher homology or identity, for example, genes having the homology or identity of 40% or more, specifically 90% or more, more specifically 95% or more, furthermore specifically 97% or more, or most specifically 99% or more, hybridize only with themselves, and that genes having lower homology or identity do not hybridize with each other; or a condition that washes once, specifically 2 to 3 times at a salt concentration and a temperature corresponding to 60° C., 1×SSC, 0.1% SDS, specifically 60° C., 0.1×SSC, 0.1% SDS, more specifically 68° C., 0.1×SSC, 0.1% SDS, which is the washing condition of normal Southern hybridization.

The hybridization requires that two nucleic acids have complementary sequences, although a mismatch between the bases occurs depending on the stringency of hybridization. The term "complementary" is used to describe the relationship between nucleotide bases that can hybridize with each other. For example, with respect to DNA, adenosine is complementary to thymine and cytosine is complementary to guanine. Accordingly, the present application may also include isolated nucleic acid fragments complementary to the entire sequence as well as substantially similar nucleic acid sequences.

Specifically, the polynucleotides having homology or identity can be detected by using a hybridization condition including a hybridization step at a $T_m$ value of 55° C. and the above-described conditions. In addition, the $T_m$ value may be 60° C., 63° C. or 65° C., but may be appropriately adjusted by a person skilled in the art according to the purpose without being limited thereto.

The appropriate stringency for hybridizing the polynucleotide depends on a length and a degree of complementarity of the polynucleotide, and those variables are well known in the art (see Sambrook et al., Supra, 9.50-9.51, 11.7-11.8).

Another aspect of the present application provides a vector comprising the polynucleotide encoding the ornithine decarboxylase variant.

The ornithine decarboxylase comprising the amino acid sequence of SEQ ID NO. 1, its variant and the polynucleotide are as described above.

The term "vector" as used herein refers to a DNA preparation containing a base sequence of the polynucleotide encoding a target polypeptide operably linked to a suitable regulatory sequence so that the target polypeptide can be expressed in a suitable host. The regulatory sequence may include a promoter capable of initiating transcription, optional operator sequence for regulating such transcription, a sequence encoding a suitable mRNA ribosome binding site, and a sequence regulating the termination of transcription and translation. The vector is transformed into a suitable host cell, and then can be replicated or functioned independently of the host genome or be integrated into the genome itself.

The vector used in the present application is not particularly limited, and any vector known in the art can be used. Examples of commonly used vectors may include a natural or recombinant plasmid, a cosmid, a virus and a bacteriophage. For example, pWE15, M13, MBL3, MBL4, IXII, ASHII, APII, t10, t11, Charon4A, and Charon21A can be used as a phage vector or a cosmid vector, and pBR system, pUC system, pBluescriptII system, pGEM system, pTZ system, pCL system and pET system can be used as a plasmid vector. Specifically, pDZ, pACYC177, pACYC184, pCL, pECCG117, pUC19, pBR322, pMW118, pCC1BAC vectors, and the like can be used.

As an example, a polynucleotide encoding a target polypeptide in a chromosome may be inserted into the chromosome through a vector for intracellular chromosomal insertion. The insertion of the polynucleotide into the chromosome may be performed by any method known in the art, for example, by a homologous recombination, but is not limited thereto. A selection marker for identifying whether the chromosome is inserted may be further included. The selection marker is to select cells transformed with the vector, that is, to identify whether a target nucleic acid molecule is inserted, and markers conferring a selectable phenotype such as drug resistance, nutritional demand, resistance to a cytotoxic agent, or expression of a surface polypeptide may be used as the selection marker. Under an environment treated with a selective agent, only cells expressing the selection marker survive or exhibit a different expression trait so that the transformed cells can be selected.

As another aspect of the present application, the present application provides a microorganism that produces putrescine, including an ornithine decarboxylase or a variant thereof, or a polynucleotide encoding the ornithine decarboxylase.

In the present application, the term "microorganism comprising a variant polypeptide" or "microorganism comprising a variant of ornithine decarboxylase" includes any microorganism capable of producing putrescine, including the protein variant of the present application, but is not limited thereto. For example, the microorganism containing the protein variant of the present application may be a recombinant microorganism having increased putrescine production capacity, putrescine production purity or putrescine production selectivity, by expressing the protein variant of the present application in a naturally wild microorganism or a microorganism producing putrescine. The recombinant microorganism may be a microorganism having increased putrescine production capacity, production purity or putrescine production selectivity compared to the naturally wild microorganism or a non-variant microorganism, but is not limited thereto.

Specifically, the microorganism is a microorganism expressing the variant of ornithine decarboxylase containing at least one amino acid variation in the amino acid sequence of SEQ ID NO. 1, wherein the amino acid variation may include substitution of the 713th and/or the 698th amino acid from the N-terminal with other amino acids. In addition, the microorganism may be a microorganism expressing a variant polypeptide having a putrescine production activity, wherein the 713th or the 698th amino acid is substituted with other amino acid in the amino acid sequence of SEQ ID NO. 1, but is not limited thereto.

The putrescine, the ornithine decarboxylase protein comprising the amino acid sequence of SEQ ID NO. 1 and its variant are as described above.

In the present application, the term "a protein is expressed" means a state in which a target protein is introduced into a microorganism or modified to be expressed in the microorganism. In case the target protein is a protein present in the microorganism, it refers to a state in which its activity is enhanced compared to its intrinsic activity or the activity before modification. For the purposes of the present application, the "target protein" may be a variant of ornithine decarboxylase protein having the putrescine production capacity described above.

Specifically, the term "introduction of a protein" means that the microorganism exhibits activity of a specific protein which is not originally possessed or shows enhanced activity compared to the intrinsic activity of the protein or the activity before modification of the protein. For example, a polynucleotide encoding a specific protein may be introduced into a chromosome in the microorganism or a vector containing the polynucleotide encoding the specific protein may be introduced into the microorganism to exhibit its activity. In addition, the "activity enhancement" means that the activity is improved compared to the intrinsic activity or the activity before modification of a specific protein possessed by the microorganism. The "intrinsic activity" refers to an activity of the specific protein originally possessed by a parent strain before transformation, when a trait of the microorganism is modified due to a genetic variation caused by a natural factor or an artificial factor.

Specifically, the activity enhancement of the present application may be made by any one or more methods selected from the group consisting of a method of increasing the number of copies in cells of a gene encoding the protein variant of the present application, a method of introducing variation into the expression regulating sequence of the gene encoding the protein variant, a method of replacing the expression regulating sequence of the gene encoding the variant of ornithine decarboxylase protein with a sequence having strong activity, a method of replacing a gene encoding a wild type protein of ornithine decarboxylase on the chromosome with the gene encoding the protein variant, a method of additionally introducing variation into the gene encoding the ornithine decarboxylase protein to enhance the activity of the protein variant, and a method of introducing the protein variant into the microorganism, but it is not limited to thereto.

In the above, the increase in the number of copies of a gene is not particularly limited, but may be performed in a form operably linked to a vector or carried out by inserting the gene into a chromosome in a host cell. Specifically, a vector capable of replicating and functioning independently of the host, into which the polynucleotide encoding the protein of the present application is operably linked, may be introduced into the host cell. Alternatively, a vector capable of inserting the polynucleotide into the chromosome in the host cell, into which the polynucleotide is operably linked, may be introduced into the chromosome of the host cell. The insertion of the polynucleotide into the chromosome can be made by any method known in the art, for example, a homologous recombination.

Modification of the expression regulating sequence for increasing the expression of the polynucleotide is not particularly limited, but may be performed by deleting, inserting, or non-conservatively or conservatively substituting the nucleic acid sequence, or inducing variation on the sequence with a combination thereof so as to further enhance the activity of the expression regulating sequence, or replacing it with a nucleic acid sequence having stronger activity. The expression regulating sequence is not particularly limited, but may include a promoter, an operator sequence, a sequence encoding a ribosome binding site, a sequence that regulates termination of transcription and translation, and the like.

A strong promoter may be linked to an upper site of the polynucleotide expression unit, instead of an original promoter, but is not limited thereto. Example of the known strong promoter include cj1 to cj7 promoter (Korean Patent Registration No. 10-0620092), lac promoter, trp promoter, trc promoter, tac promoter, lambda phage PR promoter, PL promoter, tet promoter, gapA promoter, SPL7 promoter, SPL13 (sm3) promoter (Korean Patent Registration No. 10-1783170), 02 promoter (Korean Patent Registration No. 10-1632642), tkt promoter and yccA promoter, but are not limited thereto.

Modification of the polynucleotide sequence on the chromosome is not particularly limited, but may be performed by deleting, inserting, or non-conservatively or conservatively substituting the nucleic acid sequence, or inducing variation on the expression regulating sequence with a combination thereof so as to further enhance the activity of the polynucleotide sequence, or replacing it with a polynucleotide sequence improved to have stronger activity.

By introducing and enhancing such protein activity, the activity or concentration of the corresponding protein may generally be increased to at least 1%, 10%, 25%, 50%, 75%, 100%, 150%, 200%, 300%, 400% or 500%, or up to 1000% or 2000%, based on the activity or concentration of the protein in a wild type or non-variant microorganism strain, but is not limited thereto.

In the present application, the microorganism containing the variant of ornithine decarboxylase or containing the polynucleotide encoding it may be a recombinant microorganism prepared by transformation with a vector containing the polynucleotide, but is not limited thereto.

The term "transformation" in the present application means that a vector containing a polynucleotide encoding a target protein is introduced into a host cell so that the protein encoded by the polynucleotide can be expressed in the host cell. The transformed polynucleotides may include all of them regardless of whether they inserted and located inside the chromosome of the host cell or located outside the chromosome, as long as they can be expressed in the host cell. In addition, the polynucleotide includes DNA and RNA encoding the target protein. The polynucleotide may be introduced into the host cell and expressed in any form as long as it can be expressed. For example, the polynucleotide may be introduced into the host cell in the form of an expression cassette, which is a gene structure containing all elements necessary for self-expression. The expression cassette may include a promoter, a transcription-terminal signal, a ribosome binding site, and a translation-terminal signal, which are operably linked to the polynucleotide. The expression cassette may be in the form of an expression vector capable of self-replicating. In addition, the polynucleotide may be introduced into the host cell in its own form and may be operably linked to a sequence required for expression in the host cell, but is not limited thereto.

Further, the term "operably linked to" in the above means that the promoter sequence and the gene sequence that allow to initiate and mediate transcription of the polynucleotide encoding the target polypeptide of the present application are functionally linked with each other.

The term "non-variant microorganism" of the present application refers to a native strain itself, a microorganism that does not contain the protein variant of the present application, or a microorganism that is not transformed with a vector containing a polynucleotide encoding the protein variant of the present application.

The 'microorganism' of the present application may include any prokaryotic and eukaryotic microorganisms as long as it can produce putrescine.

In the present application, the term, "microorganisms producing putrescine" refers to a wild type microorganism that naturally has putrescine production capability or a microorganism having the putrescine production capability by introducing wild type or variant strains into a parent strain that does not have or has significantly less putrescine production capability. Specifically, it may be a microorganism having a weakened or strengthened certain mechanism due to a cause such as insertion of an external gene, or enhanced activity or inert activity of an intrinsic gene, including all microorganisms in which natural or artificial genetic modification has occurred, and may be a microorganism that is genetically modified or has enhanced activity for the putrescine production. For the purposes of the present application, the microorganism of the present application may include the protein variant of the present application, and may increase the production capacity, production purity, or production selectivity of putrescine. Specifically, the microorganism of the present application may be a microorganism that a part of the gene in a putrescine biosynthetic pathway is enhanced or weakened, or a part of the gene in a putrescine degradation pathway is enhanced or weakened. For the purposes of the present application, the microorganism producing putrescine may mean a microorganism, including the variant of ornithine decarboxylase, characterized in that the desired production amount, purity, or production selectivity of putrescine is increased from a carbon source in a medium, compared to a wild type or non-variant microorganism. In the present application, the "microorganism producing putrescine" may be used interchangeably with "microorganism having putrescine production capacity" or "putrescine production microorganism".

The microorganism producing putrescine may be a recombinant microorganism. The recombinant microorganism is as described above.

The microorganism producing putrescine is not particularly limited as long as it can produce putrescine, and specifically may include microorganisms belonging to *Corynebacterium* sp., *Escherichia* sp., *Enterbacter* sp., *Erwinia* sp., *Serratia* sp., *Providencia* sp. and *Brevibacterium* sp. More specifically, it may include microorganisms belonging to *Corynebacterium* sp., or *Escherichia* sp.

Furthermore specifically, *Escherichia* sp. microorganism may be *Escherichia coli*, and *Corynebacterium* sp. microorganism may include *Corynebacterium glutamicum*, *Corynebacterium ammoniagenes*, *Corynebacterium crudilactis*, *Corynebacterium deserti*, *Corynebacterium efficiens*, *Corynebacterium callunae*, *Corynebacterium stationis*, *Corynebacterium singulare*, *Corynebacterium halotolerans*, *Corynebacterium striatum*, *Corynebacterium pollutisoli*, *Corynebacterium imitans*, *Corynebacterium testudinoris*, *Corynebacterium flavescens*, *Corynebacterium glutamicum*, or the like. However, the microorganisms belonging to *Corynebacterium* sp. or *Escherichia* sp. that can increase the production amount of putrescine, the purity of putrescine, or the production selectivity of putrescine by introducing or enhancing the ornithine decarboxylase protein can also be included without any limitation.

In the present application, the parent strain of the microorganism that is modified to express the ornithine decarboxylase protein or the protein variant to producing the putrescine is not particularly limited as long as it is the microorganism producing putrescine.

Although the microorganism *Corynebacterium* sp. do not have a pathway for biosynthesis of putrescine, the putrescine can be synthesized by introducing the ornithine decarboxylase (ODC) from the outside.

Further, the microorganism that produces putrescine is not particularly limited, but additionally may include the ones that ornithine carbamoyltransferase (ArgF) involved in the synthesis of arginine from ornithine and a protein involved in release of glutamate (NCg11221)) are inactivated.

Further, the microorganism that produces putrescine is not particularly limited thereto, but, for example, for enhancing a biosynthetic pathway from glutamate to ornithine, may include acetylglutamate synthase that converts glutamate to acetylglutamate (N-acetylglutamate) or ornithine acetyltransferase (ArgJ) that converts acetylornithine to ornithine, acetylglutamate kinase (ArgB) that converts acetylglutamate to acetylglutamyl phosphate (N-acetylglutamyl phosphate), acetyl gamma glutamyl phosphate reductase (ArgC) that converts acetylglutamyl phosphate to acetylglutamate semialdehyde (N-acetylglutamate semialdehyde), or acetylornithine aminotransferase (ArgD) that converts acetylglutamate semialdehyde to acetylornithine (N-acetylornithine). Since these activities are enhanced compared to the intrinsic activity, the productivity of ornithine used as the biosynthetic raw material for putrescine can be improved.

Further, the microorganism that produces putrescine is not particularly limited thereto, but may further include the microorganism *Corynebacterium* sp. having putrescine production capacity, wherein the activity of putrescine acetyltransferase is attenuated. In addition, the microorganism that produces putrescine may have the activity of the putrescine release protein enhanced without limitation thereto.

In the present application, the term "enhancing/increasing" is refers to a concept encompassing both increased activity compared to intrinsic activity.

Enhancing or increasing of such gene activity can be achieved by application of various methods well known in the art. Examples of such methods may include any one or more methods selected from the group consisting of a method of increasing the number of copies in cells of a gene; a method of introducing variation into the expression regulating sequence of the gene; a method of replacing the expression regulating sequence of the gene with a sequence having strong activity; a method of additionally introducing variation into the gene to enhance the activity of the gene; and a method of introducing a foreign gene into the microorganism, and may further include a combination of the above methods, but is not particularly limited by the above examples.

In the present application, the term, "Inactivation" is a concept that includes both weakened or inactive activity compared to an intrinsic activity.

The inactivation of such gene activity can be achieved by application of various methods well known in the art. Examples of the methods may include a method of deleting all or part of a gene on a chromosome, including removal of the gene activity; a method of replacing the gene encoding the protein on the chromosome with a mutated gene so that the protein activity is reduced; a method of introducing variation into an expression regulating sequence of the gene on the chromosome encoding the protein; a method of replacing the expression regulating sequence of the gene encoding the protein with a sequence having weakened or inactive activity (e.g., a method of replacing a promoter of the gene with a weaker promoter than the intrinsic promoter); a method of deleting all or part of the gene on the chromosome encoding the protein; a method of introducing an antisense oligonucleotide (e.g., antisense RNA) that complementarily binds to a gene transcript on the chromosome to inhibit translation from the mRNA to a protein; a method of artificially adding a sequence complementary to a SD sequence to the front end of the SD sequence of the gene encoding the protein to form a secondary structure, thereby making it impossible to attach ribosome; a RTE (reverse transcription engineering) method of adding a promoter to reverse transcription at the 3' end of an ORF (open reading frame) of the sequence; and a combination thereof, but are not particularly limited by the above examples. In the present application, the term "intrinsic activity" refers to the activity of a specific protein originally possessed by a parent strain before transformation, when a trait of a microorganism changes by genetic variation due to natural or artificial factor.

In another aspect of the present application, there is provided a method for producing putrescine, comprising culturing a microorganism producing the putrescine in a medium.

The putrescine, the ornithine decarboxylase comprising the amino acid sequence of SEQ ID NO. 1, the variant thereof, expression of the protein, and the microorganism are as described above.

As used herein, the term "cultivation" refers to growing a microorganism under appropriately adjusted environmental condition. A culture process of the present application may be performed according to a suitable medium and the culture condition known in the art. This culture process can be easily adjusted and used by those skilled in the art according to a selected strain. Specifically, the cultivation may be performed batchwise, continuously and fed-batch, but is not limited thereto.

The term "medium" in the present application means a substance in which nutrients required for culturing the microorganism are mixed as main components, and supplies nutrients and growth factors, including water indispensable for survival and growth. Specifically, the medium and other culture condition used for culturing the microorganism of the present application can be used without any particular limitation as long as they are media used for cultivation of an ordinary microorganism. The microorganism of the present application can be cultured by adjusting a temperature, a pH, etc. under an aerobic condition in a normal medium containing a suitable carbon source, nitrogen source, phosphorus source, inorganic compound, amino acid and/or vitamin, and the like.

In the above method, a step of culturing the microorganism is not particularly limited, but may be performed by a known batch culture method, a continuous culture method, a fed-batch culture method, or the like. In this case, the culture condition is not particularly limited, and can be adjusted by using a basic compound (e.g., sodium hydroxide, potassium hydroxide or ammonia) or an acidic compound (e.g., phosphoric acid or sulfuric acid) at an appropriate pH (e.g., pH 5 to 9, specifically pH 6 to 8, most specifically pH 6.8), and the aerobic condition may be maintained by introducing an oxygen or an oxygen-containing gas mixture into the culture. The culture temperature may be maintained at 20 to 45° C., specifically 25 to 40° C., and the culture time may be about 10 to 160 hours, but they are not limited thereto. The putrescine produced by the culture may be secreted into the medium or remain in the cells.

Further, the culture medium may contain, as the carbon source, a sugar and carbohydrate (e.g., glucose, sucrose, lactose, fructose, maltose, molasse, starch and cellulose), an oil and fat (e.g., soybean oil, sunflower seed oil, peanut oil and coconut oil), a fatty acid (e.g., palmitic acid, stearic acid and linoleic acid), an alcohol (e.g., glycerol and ethanol), and an organic acid (e.g., acetic acid), individually or in combination. However, the culture medium is not limited to thereto. As the nitrogen source, a nitrogen-containing organic compound (e.g., peptone, yeast extract, gravy, malt extract, corn steep liquor, soybean meal, and urea), or an inorganic compound (e.g., ammonium sulfate, ammonium chloride, ammonium phosphate, ammonium carbonate, and ammonium nitrate) may be used individually or in combination, but is not limited thereto. As the phosphorus source, potassium dihydrogen phosphate, dipotassium hydrogen phosphate, and sodium-containing salt corresponding thereto may be used individually or in combination, but are not limited thereto. Additionally, the medium may contain other metal salt (e.g., magnesium sulfate or iron sulfate), an essential growth-promoting substance such as amino acid and vitamin.

A method for recovering putrescine produced by the culturing step of the present application may use a suitable method known in the art according to the culture method to collect the desired amino acid from the culture medium. For example, a centrifugation, a filtration, an anion exchange chromatography, a crystallization, and a HPLC may be used, and the desired putrescine can be recovered from the medium or the microorganism using a suitable method known in the art. The method for recovering putrescine may further include a purification step.

As another aspect of the present application, there is provided a method for increasing a purity of putrescine, comprising culturing the microorganism that produces putrescine. In addition, the present invention provides a method for increasing a ratio of putrescine to cadaverine, comprising culturing the microorganism that produces putrescine. The putrescine and the microorganism are as described above.

As another aspect of the present application, there is provided a use of putrescene in producing a polyamide, that is prepared by culturing the microorganism producing putrescine. In addition, the present application provides a composition for producing a polyamide containing the microorganism that produces putrescine. The putrescine and the microorganism are as described above.

The putrescine-producing microorganism comprises a microorganism containing ornithine decarboxylase, that comprises a polypeptide of SEQ ID NO. 1, or substitution of amino acids at the positions corresponding to a) the 713th, b) the 698th, or c) the 713th and the 698th of SEQ ID NO. 1, and a polypeptide having a sequence homology of at least 80% and less than 100% with the polypeptide of SEQ ID NO. 1. In addition, the step of culturing the microorganism producing putrescin comprises culturing a microorganism comprising ornithine decarboxylase, that comprises a polypeptide of SEQ ID NO. 1, or substitution of amino acids at the positions corresponding to a) the 713th, b) the 698th, or c) the 713th and the 698th of SEQ ID NO. 1, and a polypeptide having a sequence homology of at least 80% and less than 100% with the polypeptide of SEQ ID NO. 1.

The polyamide which is substances utilized in various materials is excellent in heat resistance and chemical resistance due to a hydrogen bond between the amide bonds, and has been developed as substances of various materials. For example, the polyamide may be a fiber raw material, specifically a nylon raw material. Since the polyamide fiber has excellent characteristics in high strength, abrasion resistance, softness, gloss property, and dyeing clarity, it can be used in clothing products including a leg wear such as a pantyhose, an inner wear, a sport wear, etc. In addition, the polyamide may be a raw material for pharmaceuticals, a surfactant, a film, a plastic, etc. For example, in case of preparing a film using the polyamide, it is possible to realize excellent optical and mechanical properties together with flexibility, and thus can be used as a material for various molded products. The polyamide film can be applied to a substrate for display, a protective film for display, a touch panel, a window cover of a foldable device, and the like.

Effects of the Invention

An ornithine decarboxylase of the present application has an effect of increasing putrescine productivity or production efficiency and suppressing side reactions. In particular, the present application has an effect of inhibiting a synthesis of cadaverine, which is one of the side reactions of the ornithine decarboxylase, thereby achieving simplification of the purification/separation process of putrescine and saving of production cost.

Further, the present application can embody a variety of utilizations such as polymer precursors, pharmaceuticals, chemical additives, etc. through mass production of putrescine.

BRIEF DESCRIPTION OF THE DRAWINGS

FIG. 1 also shows a synthesis pathway of cadaverine, a side reaction of the ornithine decarboxylase that should be inhibited.

FIG. 4 shows a comparison of kinetic coefficients for lysine and ornithine, using a purified Lactobacillus-derived wild type ornithine decarboxylase, a variant (E698D) that substituted the 698th glutamic with aspartic acid, a variant (A713L) that substituted the 713th alanine with leucine, and variants (E698D/A713L) that substituted the 698th glutamic acid with aspartic acid and the 713th alanine with leucine.

FIG. 5(a) shows a graph (see ●) obtained by quantifying synthesis of putrescine with an ornithine substrate and reacting a purified Lactobacillus-derived wild type ornithine decarboxylase in a buffer of 0.37 M concentration, a graph (see ○) obtained by reacting a variant that the 713th alanine of a wild type ornithine decarboxylase is substituted with leucine in a buffer of 0.37 M concentration, a graph (see ◆) obtained by reacting a wild type ornithine decarboxylase in a buffer of 0.1 M concentration, and a graph (see ◇) obtained by reacting a variant that the 713th alanine of a wild type ornithine decarboxylase is substituted with leucine in a buffer of 0.1 M concentration. FIG. 5(b) shows a graph (see ●) obtained by quantifying synthesis of cadaverine with a lysine substrate and reacting a purified Lactobacillus-derived wild type ornithine decarboxylase in a buffer of 0.37 M concentration, a graph (see ○) obtained by reacting a variant that the 713th alanine of a wild type ornithine decarboxylase is substituted with leucine in a buffer of 0.37 M concentration, a graph (see ◆) obtained by reacting a wild type ornithine decarboxylase in a buffer of 0.1 M concentration, and a graph (see ◇) obtained by reacting a variant that the 713th alanine of a wild type ornithine decarboxylase is substituted with leucine in a buffer of 0.1 M concentration.

THE BEST FORM FOR CARRYING OUT THE INVENTION

Hereinafter, the present application will be described in more detail by Examples. However, since these Examples are intended to illustrate the present application by way of example, the scope of the present application is not limited by these Examples, and it will be apparent to those skilled in the technical field to which this application belongs.

Example 1. Comparison of Activities of Variously Derived Ornithine Decarboxylases Substrate reactivities of ornithine decarboxylases derived from four microorganisms were compared. They are wild type ornithine decarboxylases derived from Lactobacillus saerimneri (inducible), Saccharomyces cerevisiae (inducible), E. coli (constitutive), E. coli (inducible), which were denoted as ODC_Lb, ODC_Sc, ODC_Ec, and ODC_Ef, respectively. After genes corresponding to the enzymes were inserted into a pET24ma vector, the proteins were expressed under the condition of 0.1 mM IPTG and 18° C., using *E. coli* BL21 (DE3). Then, the initial reaction rates were compared at 45° C. using 10% cell extract. The case of using ornithine of 4 mM and the case of using lysine of 4 mM as the substrates were compared, respectively.

Figure 1:
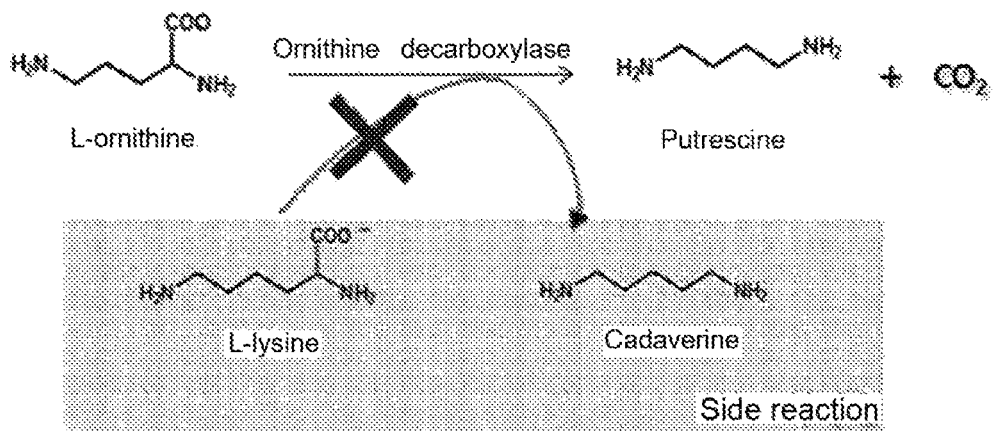
FIG. 1 is a schematic diagram showing synthesis of putrescine with an ornithine decarboxylase using ornithine as a substrate in the present application.
Figure 2:
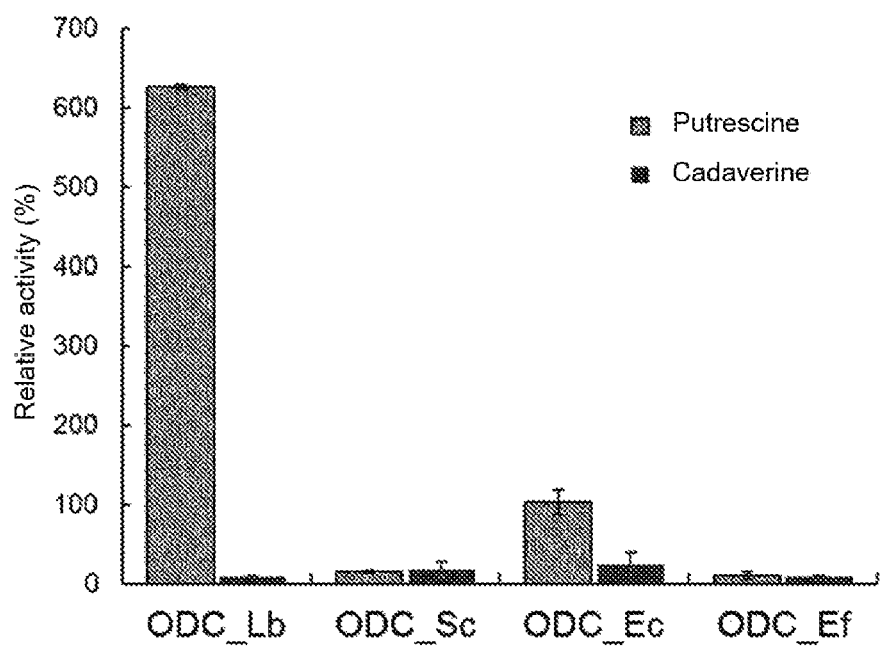
FIG. 2 confirms an activity of variously derived ornithine decarboxylases, and shows a relative activity between reactivity in case of using ornithine as a substrate and reactivity (side reaction) in case of using lysine as the substrate. ODC_Lb is derived from Lactobacillus saerimneri (inducible), ODC_Sc is derived from Saccharomyces cerevisiae (inducible), ODC_Ec is derived from E. coli (constitutive), and ODC_Ef is derived from E. coli (inducible).

FIG. 2 shows activities of the ODC enzymes derived from the four microorganisms. Specifically, FIG. 2 shows the activity of ornithine decarboxylase that produced putrescine using ornithine as a substrate, and the activity of lysine decarboxylase that produced cadaverine using lysine as the substrate. The activities of lysine decarboxylase were all similar, but the activities of ornithine decarboxylase were the best in the ornithine decarboxylase (ODC_Lb) derived from *Lactobacillus*. In other words, in connection with ODC_Lb, since a ratio of the activity of lysine decarboxylase to the activity of ornithine decarboxylase, that is, a production rate of side reactions, appears to be the lowest, production of the variant was performed based on the above ratio.

Example 2. Selection of Variation Site of Ornithine Decarboxylase

Since a crystal structure of *Lactobacillus* ornithine decarboxylase has been known, it is possible to predict a tunnel through which the substrate enters and exits the enzyme by analysis of the crystal structure. In order to select functional residues that perform saturation variation among the predicted tunnel sites, multiple sequence alignment was performed using sequence information of bioinformatics, and the positions of A696, V702, A713, and E698 were selected as variation positions from the N-terminal of the amino acid sequence of the ornithine decarboxylase used in the present invention.

Since residues conserving the amino acid residues at a specific position within the protein structure play a very important role in the structure and function of the protein and are particularly likely to play a direct role in the catalytic process, they are excluded as the variation residues.

Example 3 Performing Saturation Variation and Researching Variants on Functional Residues of Ornithine Decarboxylases Saturation variation refers to the introduction of changes in various base arrangements at a designated position in a gene. The saturation variation also means inserting a variation through PCR by inserting a NNK codon, instead of the sequence that is intended to be mutated, on a primer of a complementary sequence that binds to a template strand. In this case, in the NNK codon, N means A, T, G, C of a nucleotide, and K means T, G of the nucleotide.

The saturation variation was performed using the NNK codon on the selected functional residues, followed by screening against the variant libraries. All the libraries were subjected to primary and secondary screenings through an entire cell reaction. The entire cell reaction refers to a reaction which uses cell contents by crushing the cells containing a specific enzyme or uses entire intact cells without separating and purifying the enzyme. The first screening was conducted through the entire cell reaction of ornithine, and variants showing the activity similar to or faster than the wild type upon comparison were selected as change in absorbance. The secondary screening was conducted through the entire cell response of lysine, and among the variants selected from the primary screening, variants that the reactivity to lysine is lower than that of the wild type were selected.

A specific activity when ornithine or lysine was used as a substrate was measured for the selected variant enzymes. The specific activity refers to the activity per unit amount of pure protein from which impurities and other proteins are removed through enzymatic purification, and is usually expressed as the number of unit per 1 mg, wherein an amount of enzyme that catalyzes a substrate change of 1 µmol per minute is 1 unit. Specifically, the *Lactobacillus*-derived wild type and variant ornithine decarboxylases were transformed into *E. coli* BL21 (DE3) and expressed using IPTG as an inducer in a culture volume of 50 mL, and then only pure proteins were purified from them using a Ni-NTA column. First, after expression of the proteins, the cells were crushed with a sonic crusher, and centrifuged to obtain a cell extract. The cell extract was put in a column equilibrated with 50 mM phosphate buffer solution (pH8.0) to which 300 mM sodium chloride was added, and then bound with a nickel resin at 0° C. for 1 hour. Subsequently, a protein that failed to bind to the resin were shed, and other proteins that were non-specifically bound were removed with a Tris buffer solution containing 50 mM imidazole. Finally, only the desired protein was eluted with a Tris buffer solution containing 250 mM imidazole. In order to remove the imidazole from the eluted protein, a desalting process using a filtration column was performed to finally obtain only the active protein. Thereafter, an amount of the protein was measured using a Bradford protein quantification kit, and the specific activity was measured using the same amount of protein.

When ornithine or lysine was used as a substrate, the specific activity of *Lactobacillus*-derived wild type and variant ornithine decarboxylases was measured by HPLC (High-Performance Liquid Chromatography) analysis. The reaction was performed at 50° C. for 30 minutes to 300 minutes to obtain an average value from the experiments three times. The initial reaction rate was measured when a conversion yield of 10% to 25% was shown. A cation exchange column was used and the moving phase consisted of 0.6 g/L citric acid, 4 g/L tartaric acid, 1.4 g/L ethyldiamine, 5% methanol and 95% water. The buffer solution of pH used was a citric-sodium citrate buffer in case of pH 5.0. The specific activity of the wild type and variant ornithine decarboxylases was shown in FIG. 3.

Figure 3:
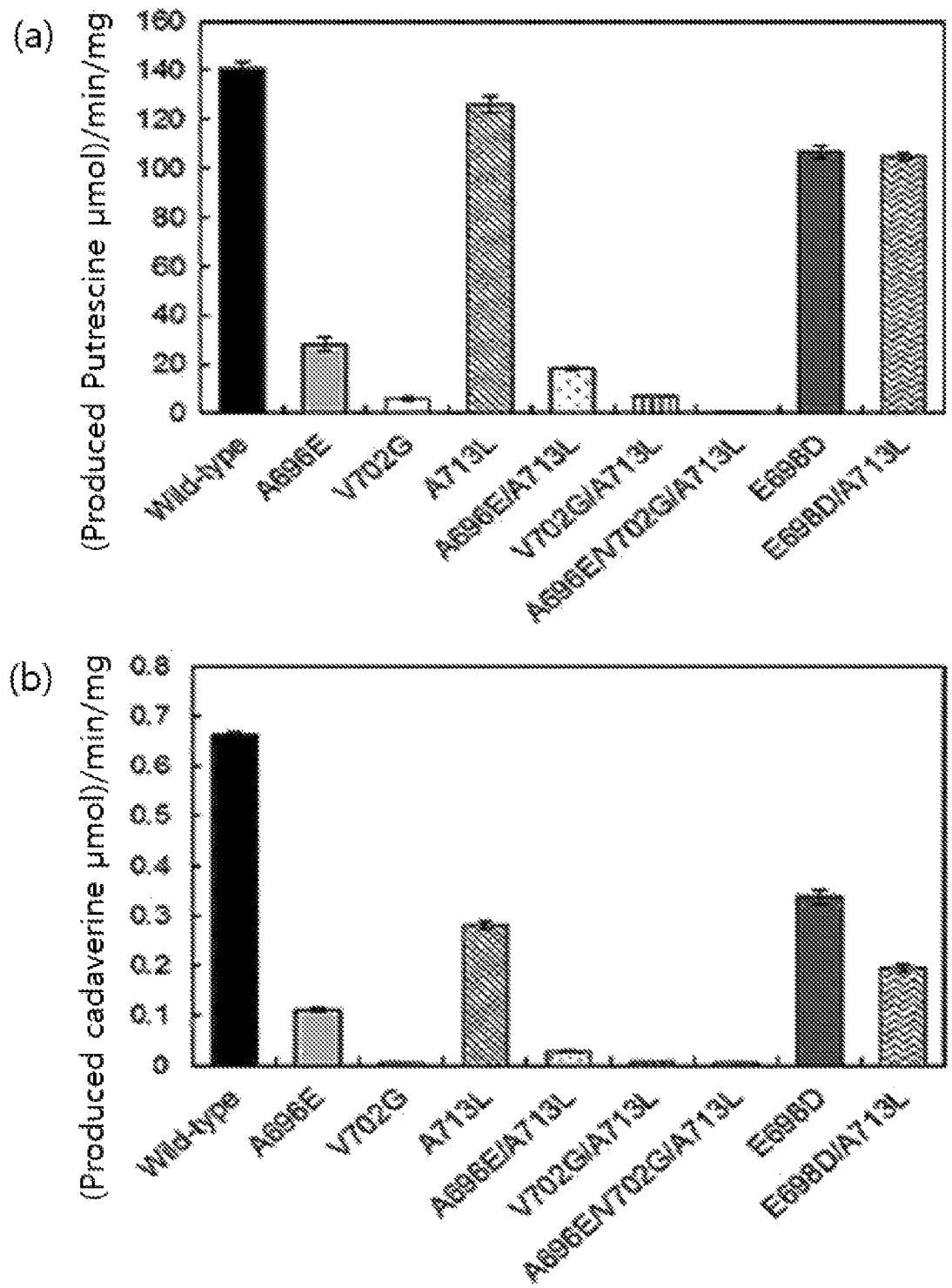
FIG. 3 is graphs comparing (a) a specific activity of ornithine and (b) a specific activity of lysine after quantifying each of them, using a purified Lactobacillus-derived wild type ornithine decarboxylase, the variant (A696E) that substituted 696th alanine of wild type ornithine decarboxylase with glutamic acid, the variant (V702G) that substituted 702th valine of wild type ornithine decarboxylase with glycine, a variant (A713L) that substituted 713th alanine with leucine, variants (A696E/A713L) that substituted 696th alanine with glutamic acid and the 713th alanine with leucine, variants (V702G/A713L) that substituted the 702th valine with glycine and the 713th with leucine, variants (A696E/V702G/A713L) that substituted the 696th alanine with glutamic acid, the 702th valine with glycine and the 713th alanine with leucine, a variant (E698D) that substituted the 698th glutamic acid with aspartic acid and variants (E698D/A713L) that substituted the 698th glutamic acid with aspartic acid and the 713th alanine with leucine.

As shown in FIGS. 3(*a*) and 3(*b*), as a result of confirming the specific activities of the wild type enzyme and the variant enzyme (A696E, V702G, A713L, A696E/A713L, V702G/A713L, A696E/V702G/A713L, E698D, and E698D/A713L), it was verified that the functional residues (A696, V702, A713, E698) were all located in an active site or a substrate access tunnel.

Specifically, in case ornithine was used as the substrate, the specific activities of the variants (A696E, V702G, A713L, A696E/A713L, V702G/A713L, A696E/V702G/A713L, E698D, E698D/A713L) were confirmed to be 19.9%, 4.3%, 89.4%, 12.8%, 4.9%, 0.1%, 75.6%, and 74.4%, respectively, compared to the specific activities of the wild types (FIG. 3(*a*)).

In case lysine was used as the substrate, the specific activities of the variant enzymes (A696E, V702G, A713L, A696E/A713L, V702G/A713L, A696E/V702G/A713L, E698D, E698D/A713L) were confirmed to be 16.9%, 0.6%, 42.4%, 4.4%, 0.9%, 0.7%, 50.8%, and 29.2%, respectively, compared to the specific activities of the wild type enzymes, which confirm suppression of the side reaction (FIG. 3(*b*)).

Example 4. Confirmation of Kinetic Parameters for Functional Residues of Ornithine Decarboxylases Among the variants of ornithine decarboxylases used in Example 3, the properties of A713L, E698D, and E698D/A713L, which are the variants having the specific activity of 70% or more, were intended to be more closely identified. Lysine having various concentration conditions was used to compare kinetic parameters of the variants and the wild types. The kinetic parameter represents a substrate affinity and a substrate conversion capacity value of enzymes using substrate solutions with different concentrations.

Specifically, lysine concentration of 0.45 mM to 140 mM was used to confirm the kinetic parameter for lysine of the wild type and variant ornithine decarboxylases after protein purification. A buffer solution of pH was a citric-sodium citrate buffer of pH 5.0, and a reaction volume was performed at 200 μl. The analysis was conducted through the HPLC analysis method specified above, and was obtained as an average value of the experiments three times. The kinetic parameters of the wild type and variant lysine decarboxylases were shown in FIG. 4.

As shown in FIG. 4, it was confirmed that a $k_{cat}$ value of the variant (A713L) for lysine was 2.16 times lower than that of the wild type. It was confirmed that a $k_{cat}/K_M$ value for lysine of the variant (A713L) was decreased by 1.93 times compared to the wild type due to decrease in the $k_{cat}$ value. In conclusion, it was confirmed that the variant (A713L) can reduce the activity of lysine decarboxylase. The variants E698D and E698D/A713L also confirmed that the $k_{cat}$ values for lysine were reduced to 2.08 and 2.59 times, respectively, compared to the wild type, and it was confirmed that the $k_{cat}/K_M$ values for lysine were reduced by 1.28 times and 1.67 times. That is, it was confirmed that the variants can reduce the side reactions.

Example 5. Characteristic Analysis of Variant Ornithine Decarboxylase

This Example was intended to investigate, among the variants, the effect of the variant (A713L) of ornithine decarboxylase having the highest the specific activity of ornithine on the production of putrescine or cadaverine. A case where ornithine having a high concentration of 51.5 g/L (0.39 M) was used as a substrate and a case where lysine having a concentration of 2.57 g/L (17.6 mM) was used as the substrate were performed, respectively. In order to obtain suitable reaction conditions for the two substrates, a buffer concentration for titrating the pH under the two conditions was 0.1 M or 0.37 M.

Figure 5:
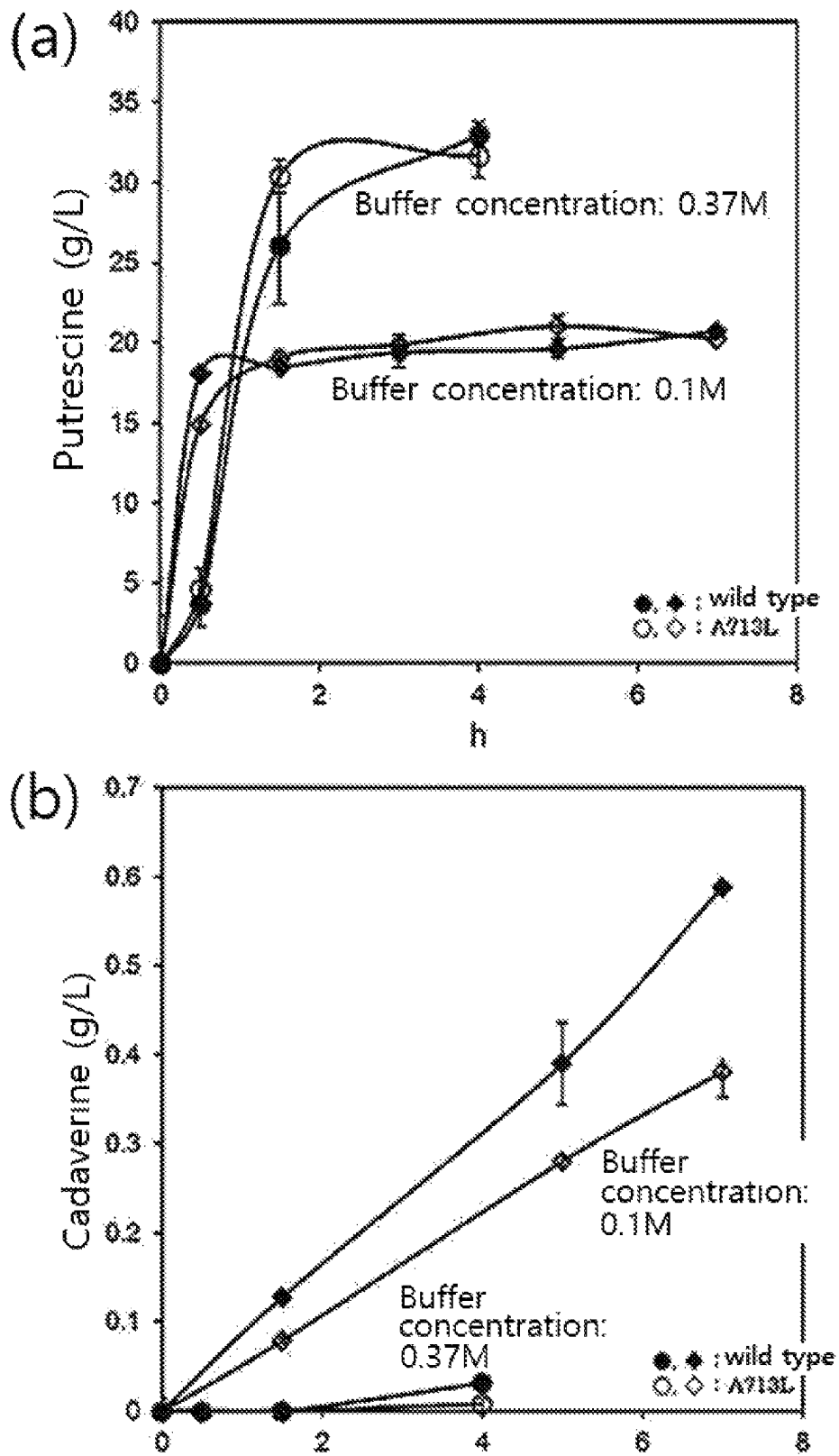
FIG. 5 is views comparing bioconversion reactions under various conditions.

Specifically, 0.1 mg of the wild type enzyme and the variant enzyme after purification of the proteins was finished were used for the reaction. 0.39 M ornithine or 17.6 mM lysine was used as the substrate, and 0.1 or 0.37 M citric-sodium citrate buffer (pH 5.0) was used as a buffer. 0.1 mM PLP coenzyme was used, and the reaction proceeded in the reaction volume of 2 mL at 50° C. The results thereon were shown in FIG. 5.

FIG. 5(a) shows that ornithine of 51.5 g/L (0.39 M) is used as the substrate. When ornithine was converted to putrescine, the putrescines of 33.0 g/L and 31.6 g/L were produced from the wild type and the variant (A713L), respectively, after 4 hours, using 0.37 M buffer (see ● and ○ in FIG. 5(a)). In addition, the putrescines of 20.2 g/L and 20.7 g/L was produced from the wild type and the variant (A713L), respectively, after 7 hours, using the buffer of a low concentration (0.1 M) (see ◆ and ◇ in FIG. 5(a)).

It was confirmed that the wild type and the variant (A713L) had a similar capability in producing the putrescine, and that using the buffer of a high concentration (0.37 M) was beneficial for the reactivity.

FIG. 5(b) shows that lysine of 2.57 g/L (17.6 mM) as the substrate. When lysine was converted to cadaverine, the cadaverines of 0.03 g/L and 0.007 g/L were produced from the wild type and the variant (A713L), respectively, after 4 hours, using 0.37 M buffer (see ● and ○ in FIG. 5(b)). In addition, when 0.1 M buffer was used, side reactions were increased to produce the cadaverines of 0.59 g/L and 0.38 g/L from the wild type and the variant (A713L), respectively, after 7 hours (see ◆ and ◇ in FIG. 5(b)). As a result, it was confirmed that the side reactions that produced the cadaverine were suppressed in the variant (A713L), and that the effect suppressing such side reactions was more noticeable in case of using the buffer of a high concentration (0.37 M).

Example 6. Comparing and Measuring Expression of Recombinant ODC Genes in Corvine Strain A method of producing a recombinant gene for expressing ODC_Lb, ODC_Sc, ODC_Ec, and ODC_Ef, which are the ornithine decarboxylases derived from the four microorganisms mentioned in Example 1, is as follows.

Specifically, using *Lactobacillus saerimneri* (ACCESSION No. P43099), *Saccharomyces cerevisiae* (ACCESSION No. J02777.1), and *Escherichia coli* str. K-12 (ACCESSION no. BAA35349) genomic information, the ornithine decarboxylase genes were amplified in the gene coding region by PCR with the gene sequence listed in Table 1 below, and then the PCR products were treated with restriction enzymes and inserted into plasmids.

TABLE 1

| Primer | Primer sequence |
|---|---|
| odc_Lb_F (SEQ ID NO. 32) | 5' -ATATCATATGAGTTCTTCTCTTAAAATTGCT-3' |
| odc_Lb_R (SEQ ID NO. 33) | 5' - ATATCTCGAGGTTGTTGTAACGATCATCGTT-3' |
| odc_Sc_F (SEQ ID NO. 34) | 5' -TAAACCATGGGCATGTCTAGTACTCAAGTAGGA-3' |
| odc_Sc_R (SEQ ID NO. 35) | 5' -ATATCTCGAGATCGAGTTCAGAGTCTATGTA-3' |
| Odc_Ec_F (SEQ ID NO. 36) | 5' - ATATCATATGAAATCAATGAATATTGCCGCC-3' |
| Odc_Ec_R (SEQ ID NO. 37) | 5' -ATATCTCGAGCTTCAACACATAACCGTACAACCG-3' |
| Odc_Ef_F (SEQ ID NO. 38) | 5' -ATATCATATGTCAAAATTAAAAATTGCGGTT-3' |
| Odc_Ef_R (SEQ ID NO. 39) | 5' -ATATCTCGAGTAATTTTTCCCCTTTCAACAG-3' |

Figure 6:
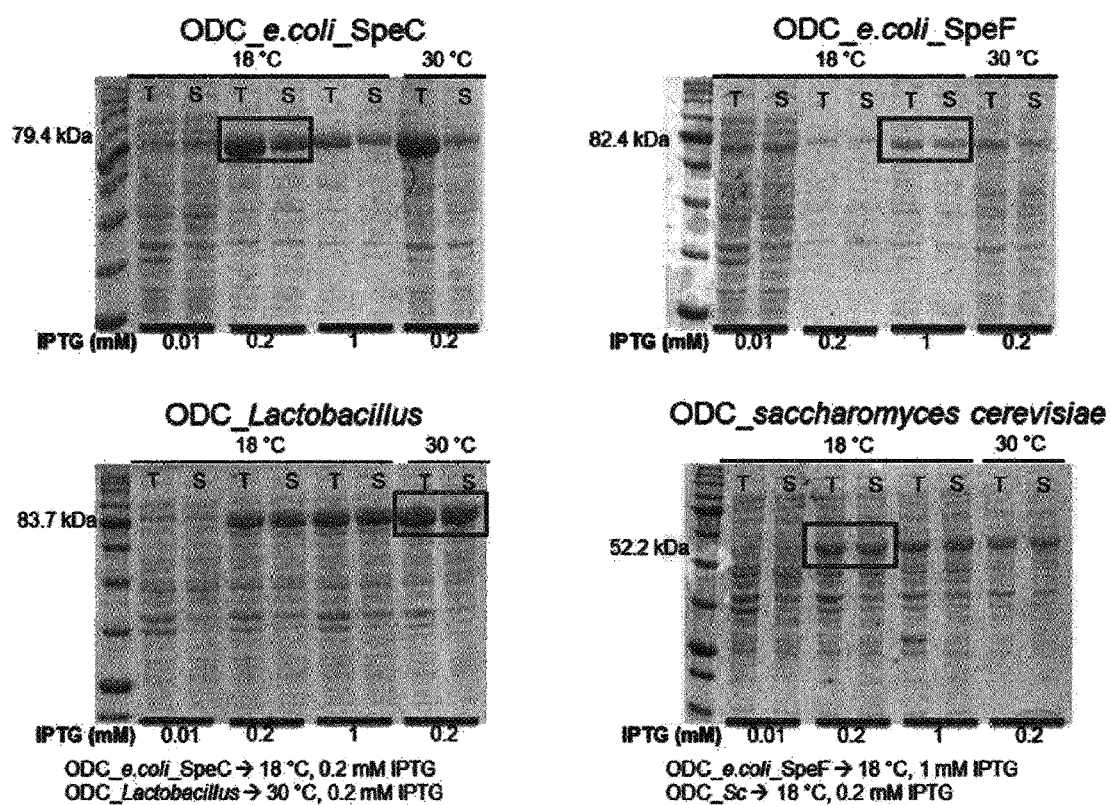
FIG. 6 shows expression levels of recombinant ornithine decarboxylase genes derived from four strains. ODC_e.coli_SpeC is derived from E. coli (constitutive), ODC_e.coli_SpeF is derived from E. coli (inducible), ODC_Lactobacillus is derived from Lactobacillus saerimneri (inducible), and ODC_Saccharomyces cerevisiae is derived from Saccharomyces cerevisiae (inducible).

The recombined genes were designed to allow additional translation of His-tag into protein C-terminal. *E. coli* DH5 alpha was used as a host strain for DNA manipulation, and E. coli BL21 (DE3) was used as the host strain for expression of C-terminal His6-tagged ODC gene. The recombinant E. coli BL21 was grown at 37° C. in a LB medium of 50 mL containing kanamycin of 50 mg/mL. When the culture solution reached 0.8 under OD600 condition, IPTG of 0.2 mM was added to the culture solution. After inducing expression of the protein at 18 to 30° C., cells were harvested. The cells were resuspended in a lysis buffer and sonicated to crush the cells. The obtained recombinant ODCs were purified at 4° C. with a Ni-NTA agarose resin from Quiagen in Hilden, Germany. Recombinant proteins were obtained using Centriplus YM-30 (Millipore, Bedford, MA) with a molecular mass cut off of 100 kDa. Expression results were shown in FIG. 6

When analyzing the results under the 30° C. expression induction condition on a SDS-PAGE gel, it can be confirmed that the expression levels of the recombinant ODC_Lb and ODC_Ec were higher than those of the ODC_Sc and ODC_Ef. However, in case of the ODC_Ec, it was confirmed that an amount of a soluble protein was significantly decreased when it was expressed under the medium temperature condition. Additionally, when the expression at 37° C. was performed, the amount of the soluble protein of ODC_Ec was further reduced.

It was intended to compare and evaluate an amount expressed as the soluble protein by expressing the ODC_Lb and ODC_Ec genes in Coryne strains. A CJ7 promoter (KCCM10617, Korean Patent Registration No. 10-0620092) was introduced in front of initiation codons of the ODC_Lb gene and the ODC_Ec gene. First, in order to obtain a gene containing the CJ7 promoter sequence, PCR was performed with the genomic DNA of Corynebacterium glutamicum ATCC13032 as a template, using the primer pair listed in Table 2 below. The PCR reaction was carried out by repeating, 30 times, processes consisting of denaturation at 95° C. for 30 seconds, annealing at 55° C. for 30 seconds and elongation at 72° C. for 30 seconds.

TABLE 2

| Primer | Primer sequence |
|---|---|
| Co-CJ7_5 (SEQ ID NO. 40) | 5'-GAAGGATCCATAGCCTACCGATGTAGAT-3' |
| Co-CJ7_3 (SEQ ID NO. 41) | 5'-AATTCTAGAAGTGTTTCCTTTCGTTGGGTAC-3' |

After electrophoresis was performed using 1.5% agarose gel, a product of the PCR nucleic acid having a size of 400 basepair (bp) was obtained. The obtained PCR product was purified using a PCR prep kit (GeneAll, Seoul). BamHI and XbaI were added to the purified PCR product and a pSCEC vector solution sample, and reacted with a restriction enzyme at 37° C. for 4 hours, and then subjected to the electrophoresis using 1.5% agarose gel. Thereafter, a band of the PCR nucleic acid product having a size of 400 bp and a band of the vector size were cut to obtain nucleic acid fragments using the Gel prep kit (GeneAll, Seoul). The purified CJ7 promoter fragments and vector of each 1 mg was ligated using a T4 ligase, and then electrophoresed to E. coli DH5 alpha strains at 2500 V. The recovered strains were plated on a LB plate medium containing 50 µg/L spectinomycin, and cultured at 37° C. for 1 day to select strains showing resistance. After selecting 18 strains and performing colony PCR with SEQ ID NOS. 9 and 10, PCR products having a size of 400 bp were identified. The production of pSCEC_cj7 having the CJ7 promoter was confirmed from the results of the colony PCR.

Based on the obtained pSCEC_cj7 vector, two genes of ODC_Lb and ODC_Ec, were amplified through the PCR using the primers listed in Table 3 below.

TABLE 3

| Primer | Primer sequence |
|---|---|
| Co-ODC_Lb_5 (SEQ ID NO. 42) | 5'-TTATATTCTAGAAGTTCTTCTCTTAAAATTGCT-3' |
| Co-ODC_Lb_3 (SEQ ID NO. 43) | 5'-TTATATGTCGACGTTGTTGTAACGATCATCGTT-3' |
| Co-ODC_Ec_5 (SEQ ID NO. 44) | 5'-TTATATTCTAGAAAATCAATGAATATTGCCGCC-3' |
| Co-ODC_Ec_3 (SEQ ID NO. 45) | 5'-TTATATGTCGACCTTCAACACATAACCGTACAACCG-3' |

The obtained PCR product and the pSCEC_cj7 vector were treated with the restriction enzyme XbaI and SalI. The restriction enzyme-treated nucleic acids were gel prep to ligate ODC_Lb, ODC_Ec and pSCEC_cj7 nucleic acid fragments and inserted into E. coli DH5 alpha strain. PSCEC_cj7_ODC_Lb and pSCEC_cj7_ODC_Ec were obtained from the selected strains that the insertion was identified, respectively, and the electrophoresis was performed at 2500 V for microorganisms KCCM11240P, which are Corynebacterium sp. producing putrescine.

Colonies were formed by plating and culturing the strains on a BHIS plate medium (Braine heart infusion 37 g/l, sorbitol 91 g/l, agar 2%) containing 50 µg/L spectinomycin. It was confirmed that the selected strains can be cultured by shaking them in a CM medium (glucose 10 g/L, polypeptone 10 g/L, yeast extract 5 g/L, beef extract 5 g/L, NaCl 2.5 g/L, Urea 2 g/L, pH 6.8) containing 50 µg/L spectinomycin. 3 mL of the produced two Corynebacterium glutamicum variants were cultured, and then centrifugated to secure fungus bodies. The obtained fungus bodies were centrifuged after crushing the cells by an ultrasonic treatment method to obtain a solution containing soluble proteins.

The ODC_Lb and ODC_Ec proteins containing His-tag were purified, respectively, using a Ni-NTA Spin Column (Hilden, Germany). A concentration of the obtained proteins was measured using a nano drop. The concentration of the recombinant proteins calculated based on the measured values were 1.282 g/L ODC_Lb and 0.039 g/L ODC_Ec, respectively, which confirms that ODC_Lb secured the soluble proteins of 30 times or more compared to ODC_Ec in the Coryne strain.

When ODC_Lb was expressed using E. coli and Coryne strain as hosts under a medium temperature condition, it could be confirmed that high soluble proteins were produced with high expression level and normal protein folding.

Example 7. Preparation of Ornithine Decarboxylase Variant-Incorporated Putrescine Production Coryne Strain and Measurement of Putrescine Production Capacity In order to investigate the effect of the ornithine decarboxylase variant of the present application on putrescine production, a strain incorporating the variant of ornithine decarboxylase into a microorganism of *Corynebacterium* sp. having improved putrescin production capacity was prepared.

Specifically, as the microorganism of *Corynebacterium* sp. having improved putrescin production capacity, the microorganism of *Corynebacterium* sp. (KCCM11240P) having putrescine production capacity disclosed in Korean Patent Laid-open Publication No. 2013-0082478 was used. The microorganism of *Corynebacterium* (KCCM11240P) is a microorganism in which NCgl1469 is defective in a microorganism prepared from *Corynebacterium glutamicum* ATCC13032 (ATCC 13032 ΔargF ΔNCgl1221 P (CJ7)-argCJBD bioAD::P (CJ7)-speC (Ec): KCCM11138P (Korean Patent Laid-open Publication No. 2012-0064046)).

A vector was prepared to substitute the ornithine decarboxylase in the putrescine-producing microorganism with a variant of ornithine decarboxylase derived from *Lactobacillus*. More specifically, DNAs of the ornithine decarboxylase variant derived from *Lactobacillus* prepared in Examples 1 and 3 were amplified using ODC_Lb_start (EcoRV)_5 and ODC_Lb_stop (MfeI)_3 primers disclosed in Table 4 below. Specifically, wild type and variant (E698D, A713L) of *Lactobacillus* ornithine decarboxylases were inserted into the prepared pET24ma vector to make each of them as a template, and PCR was performed using two primers of L-odc_start (EcoRV)_5 and L-odc_stop (MfeI)_3 shown in Table 4 below.

TABLE 4

| Primer | Primer sequence |
|---|---|
| ODC_Lb_start (EcoRV)_5 (SEQ ID NO. 46) | 5'-gcgatatcatgaaatcaatgaatattgccg-3' |
| ODC_Lb_stop (MfeI)_3 (SEQ ID NO. 47) | 5'-gccaattggttgttgtaacgatcatc-3' |

The gene fragments obtained through PCR amplification were treated with EcoRV and MfeI restriction enzymes (37° C., 3 hours), and the gene fragments of wild type and variant (E698D, A713L) of ornithine decarboxylases derived from *Lactobacillus* were inserted into pDZ-bioAD-P (CJ7) vector produced by the method disclosed in Korean Patent Laid-open Publication No. 2012-0064046. EcoRV and MfeI restriction enzymes were used in the above method. The recombinant vectors (pDZ-ODC_Lb, pDZ-ODC_Lb_E698D, pDZ-ODC_Lb_A713L) for chromosomal insertion prepared by the above method were identified by sequence analysis.

To obtain Coryne strains in which the wild type and variant ornithine decarboxylases derived from *Lactobacillus* were inserted into the chromosome, each of the pDZ-ODC_Lb, pDZ-ODC_Lb_E698D, pDZ-ODC_Lb_A713L recombinant vectors prepared above was transfected to the KCCM11240P strain using electrophoresis, and then plated on a BHIS plate medium (37 g/l of brainheart infusion, 91 g/l of sorbitol, 2% of agar, 25 µg/ml of 1 L basis+kanamycin).

A successful insertion of the vector into the chromosome was determined by presence of a blue color in a solid medium containing X-gal (5-bromo-4-chloro-3-indolyl-β-D-galactoside). After the primary chromosome-inserted strains were cultured by shaking in a nutrient medium (30° C., 8 hours), serially diluted, respectively, and plated on the solid medium containing X-gal. While most colonies indicated the blue color, they were able to select white colonies at a low rate, and the selected colonies were secondly crossed over to be able to obtain strains that the final *Lactobacillus* ornithine decarboxylase variants were introduced into the chromosome. Finally, the strains was identified by sequence analysis of the variants. The identified strains were named as KCCM11240P::ODC_Lb, KCCM11240P::ODC_Lb_E698D, KCCM11240P::ODC_Lb_A713L.

In order to confirm the effect of putrescine production capacity of the putrescine-producing strains due to introduction of the wild type and variant ornithine decarboxylases derived from *Lactobacillus*, the putrescine production capacity was evaluated.

Specifically, after the strains produced above were cultured in a CM plate medium (1% glucose, 1% polypeptone, 0.5% yeast extract, 0.5% beef extract, 0.25% NaCl, 0.2% urea, 100% NaOH 100 µl, 2% agar, pH 6.8, 1 L basis) containing 1 mM arginine at 30° C. for 16 hours, the strains were inoculated with about one Inoculation loop (platinum) in a 25 ml titer medium having the composition of Table 5 below, and then cultured by shaking with 200 rpm at 30° C. for 24 hours. Arginine of 1 mM was added to all the produced strains in the medium and cultured for fermentation.

TABLE 5

| Composition ingredient | Concentration/Content (1 L basis) |
|---|---|
| Glucose | 8% |
| Soy protein | 0.25% |
| Corn steep solid | 0.50% |
| (NH4)2SO4 | 4% |
| Urea | 0.15% |
| KH2PO4 | 0.10% |
| MgSO4—7H2O | 0.05% |
| Biotin | 100 ug |
| Thiamine hydrochloride | 3000 ug |
| Calcium-pantothenic acid | 3000 ug |
| Nicotinamide | 3000 ug |
| CaCO$_3$ | 5% |

As a result, as shown in Table 6 below, after 12 hours of the culture, an amount of putrescine production from the strains into which the variant (A713L) of ornithine decarboxylase derived from *Lactobacillus* was introduced was increased by about 115% P compared to the strains having *E. coli* ornithine decarboxylase (KCCM11240P). In addition, the strains into which the variant (A713L) of ornithine decarboxylase was introduce showed increase of about 40% P compared to the strains having a wild type ornithine decarboxylase derived from *Lactobacillus* (KCCM11240P::ODC_Lb).

Further, an amount of cadaverine production from the strains (KCCM11240P::ODC_Lb_A713L) in which the variant (A713L) of ornithine decarboxylase was introduced was decreased by about 48% P compared to KCCM11240P due to the side reactions upon production of putrescine. Judging from the concentration of the residual glucose in the culture solution, it can be seen that the consumption of sugar increases for the same time, thereby increasing productivity.

TABLE 6

| | 12 hrs | | | | |
|---|---|---|---|---|---|
| Strain | Put (g/L) | fold (%) | Cad (ppm) | fold (%) | Residual glucose (g/L) |
| KCCM11240P | 1.3 | 100 | 39.427 | 100 | 41.7 |
| KCCM11240P::ODC_Lb | 2 | 154 | 26.196 | 66 | 37.3 |
| KCCM11240P::ODC_Lb_A713L | 2.8 | 215 | 20.367 | 52 | 29 |
| KCCM11240P::ODC_Lb_E698D | 2.7 | 208 | 23.243 | 59 | 29.8 |

The above result indicates that, in virtue of the introduction of the variant ornithine decarboxylase derived from *Lactobacillus*, it is possible to not only produce putrescine of a higher concentration than before, judging from the sugar consumptions in the putrescine producing strains, but also has the effect of reducing cadaverine and improving productivity.

Example 8. Prediction of the Effect of Saturation Variation on the 713th Amino Acid Residue of *Lactobacillus* Ornithine Decarboxylase Among the selected variants, the functional residue (A713L) in which the 713th alanine of *Lactobacillus* ornithine decarboxylase was substituted with leucine was substituted with other amino acids except alanine and leucine, and then introduced into putrescine-producing strain KCCM11240P. This Example was intended to investigate the effect of the functional residue (A713L) on putrescine production.

Specifically, a mutant strain substituted by a variant in which the 713th amino acid from the N-terminal in the amino acid sequence of SEQ ID NO. 1 is substituted with other amino acid, including a hydrophobic amino acid, was prepared. The variant was substituted instead of a wild type ornithine decarboxylase derived from *E. coli* in a chromosome of the microorganism of *Corynebacterium* sp. (KCCM11240P) having an enhanced putrescine production capacity. More specifically, in order to prepare vectors substituted with valine, one of the hydrophobic amino acids, arginine, one of the basic amino acids, aspartic acid, one of the acidic amino acids, glutamine, one of the neutral amino acids, and tryptophan, one of the aromatic amino acids, respectively, PCR was carried out using the pDZ-ODC_Lb vector prepared in Example 7 as a template and using the primers disclosed in Table 4 above and Table 7 below. Firstly, the PCR was performed on the front portion (5') and the rear portion (3'), respectively, in the center of the site where the variation was to be caused, and then, secondly, the PCR was performed to combine the two PCR fragments. For example, in case of a variant (A713V) in which the 713th amino acid is replaced with valine from alanine, the front portion was amplified by PCR using ODC_Lb_start (EcoRV)_5 and ODC_Lb_A713V_3 primers, and the rear portion was amplified by PCR using ODC_Lb_A713V_5 and ODC_Lb_stop (MfeI)_3 primers. The two PCR fragments obtained through the primary PCR were used as a template for the secondary PCR, and the PCR was performed using ODC_Lb_start (EcoRV)_5 and ODC_Lb_stop (MfeI)_3 primers. The finally obtained variant A713V gene fragment of *Lactobacillus* ornithine decarboxylase was inserted into pDZ-bioAD-P (CJ7) vector in the same manner as in Example 7. The remaining variants A713R, A713D, A713W, and A713Q were also subjected to PCR in the same manner as above using the primers described in Table 7 below and inserted into the pDZ-bioAD-P (CJ7) vector. The prepared recombinant vectors for chromosome insertion (pDZ-ODC_Lb_A713V, pDZ-ODC_Lb_A713R, pDZ-ODC_Lb_A713D, pDZ-ODC_Lb_A713W, pDZ-ODC_Lb_A713Q) were identified by sequence analysis.

TABLE 7

| Primer | Primer sequence |
|---|---|
| ODC_Lb_A713V_3 (SEQ ID NO. 48) | 5'-aagaaggcgacaaggttgttgtgtacggtgaagtttacgatg-3' |
| ODC_Lb_A713V_5 (SEQ ID NO. 49) | 5'-catcgtaaacttcaccgtacacaacaaccttgtcgccttctt-3' |
| ODC_Lb_A713R_9 (SEQ ID NO. 50) | 5'-aagaaggcgacaaggttgttaggtacggtgaagtttacgatg-3' |
| ODC_Lb_A713R_5 (SEQ ID NO. 51) | 5'-catcgtaaacttcaccgtacctaacaaccttgtcgccttctt-3' |
| ODC_Lb_A713D_3 (SEQ ID NO. 52) | 5'-aagaaggcgacaaggttgttgactacggtgaagtttacgatg-3' |
| ODC_Lb_A713D_5 (SEQ ID NO. 53) | 5'-catcgtaaacttcaccgtagtcaacaaccttgtcgccttctt-3' |
| ODC_Lb_A713Q_3 (SEQ ID NO. 54) | 5'-aagaaggcgacaaggttgttcaatacggtgaagtttacgatg-3' |
| ODC_Lb_A713Q_5 (SEQ ID NO. 55) | 5'-catcgtaaacttcaccgtattgaacaaccttgtcgccttctt-3' |
| ODC_Lb_A713W_3 (SEQ ID NO. 56) | 5'-aagaaggcgacaaggttgtttggtacggtgaagtttacgatg-3' |
| ODC_Lb_A713W_5 (SEQ ID NO. 57) | 5'-catcgtaaacttcaccgtaccaaacaaccttgtcgccttctt-3' |

In order to obtain strains in which variants in which the 713th alanine of *Lactobacillus* ornithine decarboxylase was substituted with other amino acid including a hydrophobic amino acid were inserted into the chromosome, each of pDZ-ODC_Lb_A713V, pDZ-ODC_Lb_A713R, pDZ-ODC_Lb_A713D, pDZ-ODC_Lb_A713W, and pDZ-ODC_Lb_A713Q recombinant vectors prepared above was transfected into KCCM11240P strain and selected in the same method as in Example 7 to obtain strains in which final variants of *Lactobacillus* ornithine decarboxylase were introduced into the chromosome. Finally, the strains were identified by sequence analysis of the variants. The identified strains were named as KCCM11240P::ODC_Lb_A713V, KCCM11240P::ODC_Lb_A713R, KCCM11240P::ODC_Lb_A713D, KCCM11240P::ODC_Lb_A713Q, KCCM11240P::ODC_Lb_A713W.

In order to confirm the effect of putrescine production capacity of the putrescine producing strain due to the introduction of the variant in which the 713th alanine of *Lactobacillus* ornithine decarboxylase is substituted with other amino acid including a hydrophobic amino acid, the putrescine production capacity was evaluated in the same method as in Example 7.

TABLE 8

| | 12 hrs | | | | |
|---|---|---|---|---|---|
| Strain | Put (g/L) | fold (%) | Cad (ppm) | fold (%) | Residual glucose (g/L) |
| KCCM11240P | 1.3 | 100 | 39.024 | 100 | 40.9 |
| KCCM11240P::ODC_Lb | 2 | 154 | 27.283 | 70 | 37.6 |
| KCCM11240P::ODC_Lb_A713L | 2.8 | 215 | 20.069 | 51 | 29.8 |
| KCCM11240P::ODC_Lb_A713V | 2.2 | 169 | 24.123 | 62 | 31.6 |
| KCCM11240P::ODC_Lb_A713R | 2.5 | 192 | 22.961 | 59 | 25.9 |
| KCCM11240P::ODC_Lb_A713D | 2.3 | 177 | 23.615 | 61 | 33.4 |
| KCCM11240P::ODC_Lb_A713Q | 2.6 | 200 | 21.845 | 56 | 27.8 |
| KCCM11240P::ODC_Lb_A713W | 2.1 | 162 | 26.074 | 67 | 30 |

As a result, as shown in Table 8 above, the strains, into which the variant of *Lactobacillus* ornithine decarboxylase substituted with other amino acid including hydrophobic amino acid was introduced, indicated an increase in putrescine production of about 86% P in average after the culture of 12 hours, compared to the strain (KCCM11240P) having the wild type ornithine decarboxylase derived from *E. coli*. In addition, they showed an increase in putrescine production of about 21% P in average compared to the strain having the wild type ornithine decarboxylase derived from *Lactobacillus*.

Further, it can be seen that the cadaverine production caused by the side reactions upon producing the putrescine was decreased by about 41% P, and that the consumption of sugar was increased for the same time, thereby further increasing productivity, judging from a concentration of the residual glucose in the culture medium.

The above result indicates that, due to the variants substituted with valine, one of the hydrophobic amino acids, arginine, one of the basic amino acids, aspartic acid, one of the acidic amino acids, glutamine, one of the neutral amino acids, and tryptophan, one of the aromatic amino acids, in addition to the variant in which the 713th alanine of *Lactobacillus* ornithine decarboxylase is substituted with leucine, it is possible to not only produce putrescine of a higher concentration than before, judging from the sugar consumptions in the putrescine producing strains, but also has the effect of reducing cadaverine and improving productivity.

From the above descriptions, those skilled in the art to which the present application pertains will understand that the present application may be implemented in other specific form without changing the technical spirit or essential characteristics thereof. In this regard, it should be understood that Examples described above are illustrative in all respects and not restrictive. The scope of the present application should be construed to include the meaning and scope of the claims described below rather than the detailed description of the specification, and any modifications or modified forms derived from equivalent concepts thereof.

[Microbial Deposit]

BUDAPEST TREATY ON THE INTERNATIONAL RECOGNITION OF THE DEPOSIT
OF MICROORGANISMS FOR THE PURPOSE OF PATENT PROCEDURE

INTERNATIONAL FORM

RECEIPT IN THE CASE OF AN ORIGINAL DEPOSIT issued pursuant to Rule 7.1

TO: CJ Cheiljedang Co., Ltd.

Smartplex (CJ Center)

292, Ssangrim-dong, Jung-gu, Seoul, Republic of Korea

| I. IDENTIFICATION OF THE MICROORGANISM ||
|---|---|
| Identification reference given by the DEPOSITOR: | Accession number given by the INTERNATIONAL DEPOSITARY AUTHORITY: |
| Corynebacterium glutamicum CC01-0163 | KCCM11240P |
| II. SCIENTIFIC DESCRIPTION AND/OR PROPOSED TAXONOMIC DESIGNATION ||
| The microorganism identified under I above was accompanied by:<br><br>[ ] a scientific description<br><br>[ ] a proposed taxonomic designation<br><br>(Mark with a cross where applicable) ||
| III. RECEIPT AND ACCEPTANCE ||
| This International Depositary Authority accepts the microorganism identified under I above, which was received by it on December 26, 2011 (original deposit date)[1]. ||
| IV. INTERNATIONAL DEPOSITARY AUTHORITY ||
| Name: Korean Culture Center of Microorganisms<br><br>Address: Yurim Building 361-221<br>Hongje 1-dong, Seodaemun-gu, Republic of Korea | Signature(s) of person(s) having the power to represent the International Depositary Authority:<br><br><br>Date: December 26, 2011 |

[1] In Rule 6.4 (d), the above date is the date at which the status of the International Depository Authority was acquired: If a deposit deposited outside the Budapest Treaty is converted into a deposit deposited under the Budapest Treaty after obtaining the status of the International Depository Authority, the date is the date the microorganism was received by the International Depositary Authority.

What is claimed is:

1. An ornithine decarboxylase variant, comprising an amino acid substitution at a position corresponding to position a) 713, b) 698, or c) 713 and 698 of SEQ ID NO: 1, and having at least 80% but less than 100% sequence identity to the polypeptide of SEQ ID NO: 1, wherein the substitution of the amino acid at the 713th position is A713L, A713I, A713V, A713R, A713D, A713W, or A713Q, and/or wherein the substitution of the amino acid at the 698th position is E698D.

2. The ornithine decarboxylase variant according to claim 1, wherein the substitution of the amino acid is at the 713th position and is A713L, A713I, A713V, A713R, A713D, A713W, or A713Q.

3. The ornithine decarboxylase variant according to claim 1, wherein the variant comprises a polypeptide selected from the group consisting of SEQ ID NO. 4, SEQ ID NO. 8, SEQ ID NO. 9, and SEQ ID NOS. 19 to 23.

4. A polynucleotide encoding the ornithine decarboxylase variant according to claim 1.

5. A microorganism containing an ornithine decarboxylase variant, wherein the ornithine decarboxylase variant comprises a polypeptide of SEQ ID NO: 1 or a polypeptide comprising an amino acid substitution at a position corresponding to position a) 713, b) 698, or c) 713 and 698 of SEQ ID NO: 1 and having at least 80% but less than 100% sequence identity to the polypeptide of SEQ ID NO: 1, wherein the substitution of the amino acid at the 713th position is A713L, A713I, A713V, A713R, A713D, A713W, or A713Q, and/or wherein the substitution of the amino acid at the 698th position is E698D.

6. The microorganism according to claim 5, wherein the microorganism is *Escherichia* sp. or *Corynebacterium* sp.

7. A method for producing putrescine, comprising culturing a microorganism, wherein the microorganism comprises an ornithine decarboxylase variant, wherein the ornithine decarboxylase variant comprises a polypeptide of SEQ ID NO: 1, or a polypeptide comprising an amino acid substitution at a position corresponding to position a) 713, b) 698, or c) 713 and 698 of SEQ ID NO: 1 and having at least 80% but less than 100% sequence identity to the polypeptide of SEQ ID NO: 1, wherein the substitution of the amino acid at the 713th position is A713L, A713I, A713V, A713R, A713D, A713W, or A713Q, and/or wherein the substitution of the amino acid at the 698th position is E698D.

8. The method for producing putrescine according to claim 7, comprising accumulating the putrescine in a medium.

9. The method for producing putrescine according to claim 7, comprising recovering the putrescine from the cultured microorganism or the medium.

10. A method for increasing a purity of putrescine, comprising culturing a microorganism, wherein the microorganism comprises an ornithine decarboxylase variant, wherein the ornithine decarboxylase variant comprises a polypeptide of SEQ ID NO: 1, or a polypeptide comprising an amino acid substitution at a position corresponding to position a) 713, b) 698, or c) 713 and 698 of SEQ ID NO: 1 and having at least 80% but less than 100% sequence identity to the polypeptide of SEQ ID NO: 1, wherein the substitution of the amino acid at the 713th position is A713L, A713I, A713V, A713R, A713D, A713W, or A713Q, and/or wherein the substitution of the amino acid at the 698th position is E698D.

11. A method for increasing a ratio of putrescine to cadaverine (Put/Cad), comprising culturing a microorganism, wherein the microorganism comprises an ornithine decarboxylase variant, wherein the ornithine decarboxylase variant comprises a polypeptide of SEQ ID NO: 1, or a polypeptide comprising an amino acid substitution at a position corresponding to position a) 713, b) 698, or c) 713 and 698 of SEQ ID NO: 1 and having at least 80% but less than 100% sequence identity to the polypeptide of SEQ ID NO: 1, wherein the substitution of the amino acid at the 713th position is A713L, A713I, A713V, A713R, A713D, A713W, or A713Q, and/or wherein the substitution of the amino acid at the 698th position is E698D.

12. A method for producing polyamide with putrescine, wherein the putrescine is produced by culturing a microorganism comprising an ornithine decarboxylase variant, wherein the ornithine decarboxylase variant comprises a polypeptide comprising an amino acid substitution at a position corresponding to position a) 713, b) 698, or c) 713 and 698 of SEQ ID NO: 1 and having at least 80% but less than 100% sequence identity to the polypeptide of SEQ ID NO: 1, wherein the substitution of the amino acid at the 713th position is A713L, A713I, A713V, A713R, A713D, A713W, or A713Q and/or wherein the substitution of the amino acid at the 698th position is E698D.

13. A method for producing polyamide with putrescine, wherein the putrescine is produced by culturing a microorganism comprising an ornithine decarboxylase variant, wherein the ornithine decarboxylase variant comprises a polypeptide of SEQ ID NO: 1, or a polypeptide comprising an amino acid substitution at a position corresponding to position a) 713, b) 698, or c) 713 and 698 of SEQ ID NO: 1 and having at least 80% but less than 100% sequence identity to the polypeptide of SEQ ID NO: 1, wherein the substitution of the amino acid at the 713th position is A713L, A713I, A713V, A713R, A713D, A713W, or A713Q, and/or wherein the substitution of the amino acid at the 698th position is E698D.

14. The ornithine decarboxylase variant according to claim 1, wherein the substitution of the amino acid at the 713th position is A713R, A713D, or A713Q.

15. The method according to claim 11, wherein an amount of putrescine production is increased as compared to a wild type ornithine decarboxylase and/or wherein an amount of cadaverine production is decreased as compared to a wild type ornithine decarboxylase.

16. The method according to claim 11, wherein an amount of putrescine production is increased as compared to a wild type ornithine decarboxylase by at least about 20% and/or wherein and amount of cadaverine production is decreased as compared to a wild type ornithine decarboxylase by at least about 40%.

17. The method according to claim 8, wherein the medium comprises a buffer concentration of more than about 0.1M.

* * * * *

SEQUENCE LISTING

<160> NUMBER OF SEQ ID NOS: 28

<210> SEQ ID NO 1
<211> LENGTH: 731
<212> TYPE: PRT
<213> ORGANISM: Artificial Sequence
<220> FEATURE:
<223> OTHER INFORMATION: ORNITHINE DECARBOXYLASE

<400> SEQUENCE: 1

Met Ser Ser Ser Leu Lys Ile Ala Ser Thr Gln Glu Ala Arg Gln Tyr
1               5                   10                  15

Phe Asp Thr Asp Arg Val Val Val Asp Ala Val Gly Ser Asp Phe Thr
            20                  25                  30

Asp Val Gly Ala Val Ile Ala Met Asp Tyr Glu Thr Asp Val Ile Asp
        35                  40                  45

Ala Ala Asp Ala Thr Lys Phe Gly Ile Pro Val Phe Ala Val Thr Lys
    50                  55                  60

Asp Ala Gln Ala Ile Ser Ala Asp Glu Leu Lys Lys Ile Phe His Ile
65                  70                  75                  80

Ile Asp Leu Glu Asn Lys Phe Asp Ala Thr Val Asn Ala Arg Glu Ile
                85                  90                  95

Glu Thr Ala Val Asn Asn Tyr Glu Asp Ser Ile Leu Pro Pro Phe Phe
            100                 105                 110

Lys Ser Leu Lys Glu Tyr Val Ser Arg Gly Leu Ile Gln Phe Asp Cys
        115                 120                 125

Pro Gly His Gln Gly Gly Gln Tyr Tyr Arg Lys His Pro Ala Gly Arg
    130                 135                 140

Glu Phe Tyr Asp Phe Phe Gly Glu Thr Val Phe Arg Ala Asp Leu Cys
145                 150                 155                 160

Asn Ala Asp Val Ala Leu Gly Asp Leu Leu Ile His Glu Gly Pro Ala
                165                 170                 175

Val Ala Ala Glu Lys His Ala Ala Arg Val Tyr Asn Ala Asp Lys Thr
            180                 185                 190

Tyr Phe Val Leu Gly Gly Ser Ser Asn Ala Asn Asn Thr Val Thr Ser
        195                 200                 205

Ala Leu Val Ser Asn Gly Asp Leu Val Leu Phe Asp Arg Asn Asn His
    210                 215                 220

Lys Ser Val Tyr Asn Ser Ala Leu Ala Met Ala Gly Gly Arg Pro Val
225                 230                 235                 240

Tyr Leu Gln Thr Asn Arg Asn Pro Tyr Gly Phe Ile Gly Gly Ile Tyr
                245                 250                 255

Asp Ser Asp Phe Asp Glu Lys Lys Ile Arg Glu Leu Ala Ala Lys Val
            260                 265                 270

Asp Pro Glu Arg Ala Lys Trp Lys Arg Pro Phe Arg Leu Ala Val Ile
        275                 280                 285

Gln Leu Gly Thr Tyr Asp Gly Thr Ile Tyr Asn Ala His Glu Val Val
    290                 295                 300

Lys Arg Ile Gly His Leu Cys Asp Tyr Ile Glu Phe Asp Ser Ala Trp
305                 310                 315                 320

Val Gly Tyr Glu Gln Phe Ile Pro Met Met Arg Asn Ser Ser Pro Leu
                325                 330                 335

Leu Ile Asp Asp Leu Gly Pro Glu Asp Pro Gly Ile Ile Val Val Gln
            340                 345                 350

Ser Val His Lys Gln Gln Ala Gly Phe Ser Gln Thr Ser Gln Ile His

```
            355                 360                 365
Lys Lys Asp Ser His Ile Lys Gly Gln Leu Arg Tyr Cys Asp His Lys
        370                 375                 380

His Phe Asn Asn Ser Phe Asn Leu Phe Met Ser Thr Ser Pro Phe Tyr
385                 390                 395                 400

Pro Met Tyr Ala Ala Leu Asp Val Asn Ala Met Gln Glu Gly Glu
                405                 410                 415

Ala Gly Arg Lys Leu Trp His Asp Leu Leu Ile Thr Thr Ile Glu Ala
                420                 425                 430

Arg Lys Lys Leu Ile Lys Ala Gly Ser Met Phe Arg Pro Phe Val Pro
            435                 440                 445

Pro Val Val Asn Gly Lys Lys Trp Glu Asp Gly Asp Thr Glu Asp Met
        450                 455                 460

Ala Asn Asn Ile Asp Tyr Trp Arg Phe Glu Lys Gly Ala Lys Trp His
465                 470                 475                 480

Ala Tyr Glu Gly Tyr Gly Asp Asn Gln Tyr Tyr Val Asp Pro Asn Lys
                485                 490                 495

Phe Met Leu Thr Thr Pro Gly Ile Asn Pro Glu Thr Gly Asp Tyr Glu
                500                 505                 510

Asp Phe Gly Val Pro Ala Thr Ile Val Ala Asn Tyr Leu Arg Asp His
            515                 520                 525

Gly Ile Ile Pro Glu Lys Ser Asp Leu Asn Ser Ile Leu Phe Leu Met
        530                 535                 540

Thr Pro Ala Glu Thr Pro Ala Lys Met Asn Asn Leu Ile Thr Gln Leu
545                 550                 555                 560

Leu Gln Leu Gln Arg Leu Ile Glu Glu Asp Ala Pro Leu Lys Gln Val
                565                 570                 575

Leu Pro Ser Ile Tyr Ala Ala Asn Glu Glu Arg Tyr Asn Gly Tyr Thr
            580                 585                 590

Ile Arg Glu Leu Cys Gln Glu Leu His Asp Phe Tyr Lys Asn Asn
        595                 600                 605

Thr Phe Thr Tyr Gln Lys Arg Leu Phe Leu Arg Glu Phe Phe Pro Glu
610                 615                 620

Gln Gly Met Leu Pro Tyr Glu Ala Arg Gln Glu Phe Ile Arg Asn His
625                 630                 635                 640

Asn Lys Leu Val Pro Leu Asn Lys Ile Glu Gly Ile Ala Leu Glu
                645                 650                 655

Gly Ala Leu Pro Tyr Pro Pro Gly Val Phe Cys Val Ala Pro Gly Glu
                660                 665                 670

Lys Trp Ser Glu Thr Ala Val Lys Tyr Phe Thr Ile Leu Gln Asp Gly
            675                 680                 685

Ile Asn Asn Phe Pro Gly Phe Ala Pro Glu Ile Gln Val Tyr Phe
        690                 695                 700

Lys Gln Glu Gly Asp Lys Val Val Ala Tyr Gly Glu Val Tyr Asp Ala
705                 710                 715                 720

Glu Val Ala Lys Asn Asp Asp Arg Tyr Asn Asn
                725                 730

<210> SEQ ID NO 2
<211> LENGTH: 731
<212> TYPE: PRT
<213> ORGANISM: Artificial Sequence
<220> FEATURE:
<223> OTHER INFORMATION: ORNITHINE DECARBOXYLASE MUTANT
```

-continued

<400> SEQUENCE: 2

```
Met Ser Ser Ser Leu Lys Ile Ala Ser Thr Gln Glu Ala Arg Gln Tyr
1               5                   10                  15

Phe Asp Thr Asp Arg Val Val Asp Ala Val Gly Ser Asp Phe Thr
            20                  25                  30

Asp Val Gly Ala Val Ile Ala Met Asp Tyr Glu Thr Asp Val Ile Asp
                35                  40                  45

Ala Ala Asp Ala Thr Lys Phe Gly Ile Pro Val Phe Ala Val Thr Lys
50                  55                  60

Asp Ala Gln Ala Ile Ser Ala Asp Glu Leu Lys Lys Ile Phe His Ile
65                  70                  75                  80

Ile Asp Leu Glu Asn Lys Phe Asp Ala Thr Val Asn Ala Arg Glu Ile
                85                  90                  95

Glu Thr Ala Val Asn Asn Tyr Glu Asp Ser Ile Leu Pro Pro Phe Phe
                100                 105                 110

Lys Ser Leu Lys Glu Tyr Val Ser Arg Gly Leu Ile Gln Phe Asp Cys
            115                 120                 125

Pro Gly His Gln Gly Gly Gln Tyr Tyr Arg Lys His Pro Ala Gly Arg
        130                 135                 140

Glu Phe Tyr Asp Phe Phe Gly Glu Thr Val Phe Arg Ala Asp Leu Cys
145                 150                 155                 160

Asn Ala Asp Val Ala Leu Gly Asp Leu Leu Ile His Glu Gly Pro Ala
                165                 170                 175

Val Ala Ala Glu Lys His Ala Ala Arg Val Tyr Asn Ala Asp Lys Thr
            180                 185                 190

Tyr Phe Val Leu Gly Gly Ser Ser Asn Ala Asn Asn Thr Val Thr Ser
        195                 200                 205

Ala Leu Val Ser Asn Gly Asp Leu Val Leu Phe Asp Arg Asn Asn His
    210                 215                 220

Lys Ser Val Tyr Asn Ser Ala Leu Ala Met Ala Gly Gly Arg Pro Val
225                 230                 235                 240

Tyr Leu Gln Thr Asn Arg Asn Pro Tyr Gly Phe Ile Gly Gly Ile Tyr
                245                 250                 255

Asp Ser Asp Phe Asp Glu Lys Lys Ile Arg Glu Leu Ala Ala Lys Val
            260                 265                 270

Asp Pro Glu Arg Ala Lys Trp Lys Arg Pro Phe Arg Leu Ala Val Ile
        275                 280                 285

Gln Leu Gly Thr Tyr Asp Gly Thr Ile Tyr Asn Ala His Glu Val Val
290                 295                 300

Lys Arg Ile Gly His Leu Cys Asp Tyr Ile Glu Phe Asp Ser Ala Trp
305                 310                 315                 320

Val Gly Tyr Glu Gln Phe Ile Pro Met Met Arg Asn Ser Ser Pro Leu
                325                 330                 335

Leu Ile Asp Asp Leu Gly Pro Glu Asp Pro Gly Ile Ile Val Val Gln
            340                 345                 350

Ser Val His Lys Gln Gln Ala Gly Phe Ser Gln Thr Ser Gln Ile His
        355                 360                 365

Lys Lys Asp Ser His Ile Lys Gly Gln Leu Arg Tyr Cys Asp His Lys
370                 375                 380

His Phe Asn Asn Ser Phe Asn Leu Phe Met Ser Thr Ser Pro Phe Tyr
385                 390                 395                 400

Pro Met Tyr Ala Ala Leu Asp Val Asn Ala Ala Met Gln Glu Gly Glu
                405                 410                 415
```

Ala Gly Arg Lys Leu Trp His Asp Leu Leu Ile Thr Ile Glu Ala
            420                 425                 430

Arg Lys Lys Leu Ile Lys Ala Gly Ser Met Phe Arg Pro Phe Val Pro
                435                 440                 445

Pro Val Val Asn Gly Lys Lys Trp Glu Asp Gly Asp Thr Glu Asp Met
450                 455                 460

Ala Asn Asn Ile Asp Tyr Trp Arg Phe Glu Lys Gly Ala Lys Trp His
465                 470                 475                 480

Ala Tyr Glu Gly Tyr Gly Asp Asn Gln Tyr Tyr Val Asp Pro Asn Lys
                485                 490                 495

Phe Met Leu Thr Thr Pro Gly Ile Asn Pro Glu Thr Gly Asp Tyr Glu
                500                 505                 510

Asp Phe Gly Val Pro Ala Thr Ile Val Ala Asn Tyr Leu Arg Asp His
            515                 520                 525

Gly Ile Ile Pro Glu Lys Ser Asp Leu Asn Ser Ile Leu Phe Leu Met
        530                 535                 540

Thr Pro Ala Glu Thr Pro Ala Lys Met Asn Asn Leu Ile Thr Gln Leu
545                 550                 555                 560

Leu Gln Leu Gln Arg Leu Ile Glu Glu Asp Ala Pro Leu Lys Gln Val
                565                 570                 575

Leu Pro Ser Ile Tyr Ala Ala Asn Glu Glu Arg Tyr Asn Gly Tyr Thr
            580                 585                 590

Ile Arg Glu Leu Cys Gln Glu Leu His Asp Phe Tyr Lys Asn Asn Asn
        595                 600                 605

Thr Phe Thr Tyr Gln Lys Arg Leu Phe Leu Arg Glu Phe Phe Pro Glu
    610                 615                 620

Gln Gly Met Leu Pro Tyr Glu Ala Arg Gln Glu Phe Ile Arg Asn His
625                 630                 635                 640

Asn Lys Leu Val Pro Leu Asn Lys Ile Glu Gly Ile Ala Leu Glu
                645                 650                 655

Gly Ala Leu Pro Tyr Pro Pro Gly Val Phe Cys Val Ala Pro Gly Glu
                660                 665                 670

Lys Trp Ser Glu Thr Ala Val Lys Tyr Phe Thr Ile Leu Gln Asp Gly
            675                 680                 685

Ile Asn Asn Phe Pro Gly Phe Glu Pro Glu Ile Gln Gly Val Tyr Phe
        690                 695                 700

Lys Gln Glu Gly Asp Lys Val Val Ala Tyr Gly Glu Val Tyr Asp Ala
705                 710                 715                 720

Glu Val Ala Lys Asn Asp Asp Arg Tyr Asn Asn
                725                 730

<210> SEQ ID NO 3
<211> LENGTH: 731
<212> TYPE: PRT
<213> ORGANISM: Artificial Sequence
<220> FEATURE:
<223> OTHER INFORMATION: ORNITHINE DECARBOXYLASE MUTANT

<400> SEQUENCE: 3

Met Ser Ser Leu Lys Ile Ala Ser Thr Gln Glu Ala Arg Gln Tyr
1               5                   10                  15

Phe Asp Thr Asp Arg Val Val Val Asp Ala Val Gly Ser Asp Phe Thr
                20                  25                  30

Asp Val Gly Ala Val Ile Ala Met Asp Tyr Glu Thr Asp Val Ile Asp
            35                  40                  45

```
Ala Ala Asp Ala Thr Lys Phe Gly Ile Pro Val Phe Ala Val Thr Lys
        50                  55                  60

Asp Ala Gln Ala Ile Ser Ala Asp Glu Leu Lys Lys Ile Phe His Ile
65                  70                  75                  80

Ile Asp Leu Glu Asn Lys Phe Asp Ala Thr Val Asn Ala Arg Glu Ile
                85                  90                  95

Glu Thr Ala Val Asn Asn Tyr Glu Asp Ser Ile Leu Pro Pro Phe Phe
                100                 105                 110

Lys Ser Leu Lys Glu Tyr Val Ser Arg Gly Leu Ile Gln Phe Asp Cys
            115                 120                 125

Pro Gly His Gln Gly Gly Gln Tyr Tyr Arg Lys His Pro Ala Gly Arg
        130                 135                 140

Glu Phe Tyr Asp Phe Phe Gly Glu Thr Val Phe Arg Ala Asp Leu Cys
145                 150                 155                 160

Asn Ala Asp Val Ala Leu Gly Asp Leu Leu Ile His Glu Gly Pro Ala
                165                 170                 175

Val Ala Ala Glu Lys His Ala Ala Arg Val Tyr Asn Ala Asp Lys Thr
            180                 185                 190

Tyr Phe Val Leu Gly Gly Ser Ser Asn Ala Asn Asn Thr Val Thr Ser
        195                 200                 205

Ala Leu Val Ser Asn Gly Asp Leu Val Leu Phe Asp Arg Asn Asn His
    210                 215                 220

Lys Ser Val Tyr Asn Ser Ala Leu Ala Met Ala Gly Gly Arg Pro Val
225                 230                 235                 240

Tyr Leu Gln Thr Asn Arg Asn Pro Tyr Gly Phe Ile Gly Ile Tyr
            245                 250                 255

Asp Ser Asp Phe Asp Glu Lys Lys Ile Arg Glu Leu Ala Ala Lys Val
                260                 265                 270

Asp Pro Glu Arg Ala Lys Trp Lys Arg Pro Phe Arg Leu Ala Val Ile
            275                 280                 285

Gln Leu Gly Thr Tyr Asp Gly Thr Ile Tyr Asn Ala His Glu Val Val
        290                 295                 300

Lys Arg Ile Gly His Leu Cys Asp Tyr Ile Glu Phe Asp Ser Ala Trp
305                 310                 315                 320

Val Gly Tyr Glu Gln Phe Ile Pro Met Met Arg Asn Ser Ser Pro Leu
                325                 330                 335

Leu Ile Asp Asp Leu Gly Pro Glu Asp Pro Gly Ile Ile Val Val Gln
            340                 345                 350

Ser Val His Lys Gln Gln Ala Gly Phe Ser Gln Thr Ser Gln Ile His
        355                 360                 365

Lys Lys Asp Ser His Ile Lys Gly Gln Leu Arg Tyr Cys Asp His Lys
370                 375                 380

His Phe Asn Asn Ser Phe Asn Leu Phe Met Ser Thr Ser Pro Phe Tyr
385                 390                 395                 400

Pro Met Tyr Ala Ala Leu Asp Val Asn Ala Ala Met Gln Glu Gly Glu
            405                 410                 415

Ala Gly Arg Lys Leu Trp His Asp Leu Leu Ile Thr Thr Ile Glu Ala
        420                 425                 430

Arg Lys Lys Leu Ile Lys Ala Gly Ser Met Phe Arg Pro Phe Val Pro
    435                 440                 445

Pro Val Val Asn Gly Lys Lys Trp Glu Asp Gly Asp Thr Glu Asp Met
450                 455                 460
```

```
Ala Asn Asn Ile Asp Tyr Trp Arg Phe Glu Lys Gly Ala Lys Trp His
465                 470                 475                 480

Ala Tyr Glu Gly Tyr Gly Asp Asn Gln Tyr Tyr Val Asp Pro Asn Lys
                485                 490                 495

Phe Met Leu Thr Thr Pro Gly Ile Asn Pro Glu Thr Gly Asp Tyr Glu
            500                 505                 510

Asp Phe Gly Val Pro Ala Thr Ile Val Ala Asn Tyr Leu Arg Asp His
        515                 520                 525

Gly Ile Ile Pro Glu Lys Ser Asp Leu Asn Ser Ile Leu Phe Leu Met
    530                 535                 540

Thr Pro Ala Glu Thr Pro Ala Lys Met Asn Asn Leu Ile Thr Gln Leu
545                 550                 555                 560

Leu Gln Leu Gln Arg Leu Ile Glu Glu Asp Ala Pro Leu Lys Gln Val
                565                 570                 575

Leu Pro Ser Ile Tyr Ala Ala Asn Glu Glu Arg Tyr Asn Gly Tyr Thr
            580                 585                 590

Ile Arg Glu Leu Cys Gln Glu Leu His Asp Phe Tyr Lys Asn Asn Asn
        595                 600                 605

Thr Phe Thr Tyr Gln Lys Arg Leu Phe Leu Arg Glu Phe Phe Pro Glu
    610                 615                 620

Gln Gly Met Leu Pro Tyr Glu Ala Arg Gln Glu Phe Ile Arg Asn His
625                 630                 635                 640

Asn Lys Leu Val Pro Leu Asn Lys Ile Glu Gly Ile Ala Leu Glu
                645                 650                 655

Gly Ala Leu Pro Tyr Pro Pro Gly Val Phe Cys Val Ala Pro Gly Glu
            660                 665                 670

Lys Trp Ser Glu Thr Ala Val Lys Tyr Phe Thr Ile Leu Gln Asp Gly
        675                 680                 685

Ile Asn Asn Phe Pro Gly Phe Ala Pro Glu Ile Gln Gly Gly Tyr Phe
    690                 695                 700

Lys Gln Glu Gly Asp Lys Val Val Ala Tyr Gly Glu Val Tyr Asp Ala
705                 710                 715                 720

Glu Val Ala Lys Asn Asp Asp Arg Tyr Asn Asn
                725                 730

<210> SEQ ID NO 4
<211> LENGTH: 731
<212> TYPE: PRT
<213> ORGANISM: Artificial Sequence
<220> FEATURE:
<223> OTHER INFORMATION: ORNITHINE DECARBOXYLASE MUTANT

<400> SEQUENCE: 4

Met Ser Ser Leu Lys Ile Ala Ser Thr Gln Glu Ala Arg Gln Tyr
1               5                   10                  15

Phe Asp Thr Asp Arg Val Val Val Asp Ala Val Gly Ser Asp Phe Thr
                20                  25                  30

Asp Val Gly Ala Val Ile Ala Met Asp Tyr Glu Thr Asp Val Ile Asp
            35                  40                  45

Ala Ala Asp Ala Thr Lys Phe Gly Ile Pro Val Phe Ala Val Thr Lys
        50                  55                  60

Asp Ala Gln Ala Ile Ser Ala Asp Glu Leu Lys Lys Ile Phe His Ile
65                  70                  75                  80

Ile Asp Leu Glu Asn Lys Phe Asp Ala Thr Val Asn Ala Arg Glu Ile
                85                  90                  95
```

```
Glu Thr Ala Val Asn Asn Tyr Glu Asp Ser Ile Leu Pro Pro Phe Phe
            100                 105                 110

Lys Ser Leu Lys Glu Tyr Val Ser Arg Gly Leu Ile Gln Phe Asp Cys
        115                 120                 125

Pro Gly His Gln Gly Gln Tyr Tyr Arg Lys His Pro Ala Gly Arg
    130                 135                 140

Glu Phe Tyr Asp Phe Phe Gly Glu Thr Val Phe Arg Ala Asp Leu Cys
145                 150                 155                 160

Asn Ala Asp Val Ala Leu Gly Asp Leu Leu Ile His Glu Gly Pro Ala
                165                 170                 175

Val Ala Ala Glu Lys His Ala Ala Arg Val Tyr Asn Ala Asp Lys Thr
            180                 185                 190

Tyr Phe Val Leu Gly Gly Ser Ser Asn Ala Asn Asn Thr Val Thr Ser
        195                 200                 205

Ala Leu Val Ser Asn Gly Asp Leu Val Leu Phe Asp Arg Asn Asn His
    210                 215                 220

Lys Ser Val Tyr Asn Ser Ala Leu Ala Met Ala Gly Gly Arg Pro Val
225                 230                 235                 240

Tyr Leu Gln Thr Asn Arg Asn Pro Tyr Gly Phe Ile Gly Gly Ile Tyr
                245                 250                 255

Asp Ser Asp Phe Asp Glu Lys Lys Ile Arg Glu Leu Ala Ala Lys Val
            260                 265                 270

Asp Pro Glu Arg Ala Lys Trp Lys Arg Pro Phe Arg Leu Ala Val Ile
        275                 280                 285

Gln Leu Gly Thr Tyr Asp Gly Thr Ile Tyr Asn Ala His Glu Val Val
    290                 295                 300

Lys Arg Ile Gly His Leu Cys Asp Tyr Ile Glu Phe Asp Ser Ala Trp
305                 310                 315                 320

Val Gly Tyr Glu Gln Phe Ile Pro Met Met Arg Asn Ser Ser Pro Leu
                325                 330                 335

Leu Ile Asp Asp Leu Gly Pro Glu Asp Pro Gly Ile Ile Val Val Gln
            340                 345                 350

Ser Val His Lys Gln Gln Ala Gly Phe Ser Gln Thr Ser Gln Ile His
        355                 360                 365

Lys Lys Asp Ser His Ile Lys Gly Gln Leu Arg Tyr Cys Asp His Lys
    370                 375                 380

His Phe Asn Asn Ser Phe Asn Leu Phe Met Ser Thr Ser Pro Phe Tyr
385                 390                 395                 400

Pro Met Tyr Ala Ala Leu Asp Val Asn Ala Ala Met Gln Glu Gly Glu
                405                 410                 415

Ala Gly Arg Lys Leu Trp His Asp Leu Leu Ile Thr Thr Ile Glu Ala
            420                 425                 430

Arg Lys Lys Leu Ile Lys Ala Gly Ser Met Phe Arg Pro Phe Val Pro
        435                 440                 445

Pro Val Val Asn Gly Lys Lys Trp Glu Asp Gly Asp Thr Glu Asp Met
    450                 455                 460

Ala Asn Asn Ile Asp Tyr Trp Arg Phe Glu Lys Gly Ala Lys Trp His
465                 470                 475                 480

Ala Tyr Glu Gly Tyr Gly Asp Asn Gln Tyr Tyr Val Asp Pro Asn Lys
                485                 490                 495

Phe Met Leu Thr Thr Pro Gly Ile Asn Pro Glu Thr Gly Asp Tyr Glu
            500                 505                 510

Asp Phe Gly Val Pro Ala Thr Ile Val Ala Asn Tyr Leu Arg Asp His
```

```
            515                 520                 525
Gly Ile Ile Pro Glu Lys Ser Asp Leu Asn Ser Ile Leu Phe Leu Met
            530                 535                 540

Thr Pro Ala Glu Thr Pro Ala Lys Met Asn Asn Leu Ile Thr Gln Leu
545                 550                 555                 560

Leu Gln Leu Gln Arg Leu Ile Glu Glu Asp Ala Pro Leu Lys Gln Val
                565                 570                 575

Leu Pro Ser Ile Tyr Ala Ala Asn Glu Glu Arg Tyr Asn Gly Tyr Thr
            580                 585                 590

Ile Arg Glu Leu Cys Gln Glu Leu His Asp Phe Tyr Lys Asn Asn Asn
        595                 600                 605

Thr Phe Thr Tyr Gln Lys Arg Leu Phe Leu Arg Glu Phe Phe Pro Glu
    610                 615                 620

Gln Gly Met Leu Pro Tyr Glu Ala Arg Gln Glu Phe Ile Arg Asn His
625                 630                 635                 640

Asn Lys Leu Val Pro Leu Asn Lys Ile Glu Gly Glu Ile Ala Leu Glu
                645                 650                 655

Gly Ala Leu Pro Tyr Pro Pro Gly Val Phe Cys Val Ala Pro Gly Glu
            660                 665                 670

Lys Trp Ser Glu Thr Ala Val Lys Tyr Phe Thr Ile Leu Gln Asp Gly
        675                 680                 685

Ile Asn Asn Phe Pro Gly Phe Ala Pro Glu Ile Gln Gly Val Tyr Phe
    690                 695                 700

Lys Gln Glu Gly Asp Lys Val Val Leu Tyr Gly Glu Val Tyr Asp Ala
705                 710                 715                 720

Glu Val Ala Lys Asn Asp Asp Arg Tyr Asn Asn
                725                 730

<210> SEQ ID NO 5
<211> LENGTH: 731
<212> TYPE: PRT
<213> ORGANISM: Artificial Sequence
<220> FEATURE:
<223> OTHER INFORMATION: ORNITHINE DECARBOXYLASE MUTANT

<400> SEQUENCE: 5

Met Ser Ser Ser Leu Lys Ile Ala Ser Thr Gln Glu Ala Arg Gln Tyr
1               5                   10                  15

Phe Asp Thr Asp Arg Val Val Asp Ala Val Gly Ser Asp Phe Thr
            20                  25                  30

Asp Val Gly Ala Val Ile Ala Met Asp Tyr Glu Thr Asp Val Ile Asp
        35                  40                  45

Ala Ala Asp Ala Thr Lys Phe Gly Ile Pro Val Phe Ala Val Thr Lys
    50                  55                  60

Asp Ala Gln Ala Ile Ser Ala Asp Glu Leu Lys Lys Ile Phe His Ile
65                  70                  75                  80

Ile Asp Leu Glu Asn Lys Phe Asp Ala Thr Val Asn Ala Arg Glu Ile
                85                  90                  95

Glu Thr Ala Val Asn Asn Tyr Glu Asp Ser Ile Leu Pro Pro Phe Phe
            100                 105                 110

Lys Ser Leu Lys Glu Tyr Val Ser Arg Gly Leu Ile Gln Phe Asp Cys
        115                 120                 125

Pro Gly His Gln Gly Gly Gln Tyr Tyr Arg Lys His Pro Ala Gly Arg
    130                 135                 140

Glu Phe Tyr Asp Phe Phe Gly Glu Thr Val Phe Arg Ala Asp Leu Cys
```

-continued

```
               145                 150                 155                 160
        Asn Ala Asp Val Ala Leu Gly Asp Leu Leu Ile His Glu Gly Pro Ala
                        165                 170                 175
        Val Ala Ala Glu Lys His Ala Ala Arg Val Tyr Asn Ala Asp Lys Thr
                        180                 185                 190
        Tyr Phe Val Leu Gly Gly Ser Ser Asn Ala Asn Asn Thr Val Thr Ser
                        195                 200                 205
        Ala Leu Val Ser Asn Gly Asp Leu Val Leu Phe Asp Arg Asn Asn His
                        210                 215                 220
        Lys Ser Val Tyr Asn Ser Ala Leu Ala Met Ala Gly Arg Pro Val
        225                 230                 235                 240
        Tyr Leu Gln Thr Asn Arg Asn Pro Tyr Gly Phe Ile Gly Gly Ile Tyr
                        245                 250                 255
        Asp Ser Asp Phe Asp Glu Lys Lys Ile Arg Glu Leu Ala Ala Lys Val
                        260                 265                 270
        Asp Pro Glu Arg Ala Lys Trp Lys Arg Pro Phe Arg Leu Ala Val Ile
                        275                 280                 285
        Gln Leu Gly Thr Tyr Asp Gly Thr Ile Tyr Asn Ala His Glu Val Val
                        290                 295                 300
        Lys Arg Ile Gly His Leu Cys Asp Tyr Ile Glu Phe Asp Ser Ala Trp
        305                 310                 315                 320
        Val Gly Tyr Glu Gln Phe Ile Pro Met Met Arg Asn Ser Ser Pro Leu
                        325                 330                 335
        Leu Ile Asp Asp Leu Gly Pro Glu Asp Pro Gly Ile Ile Val Val Gln
                        340                 345                 350
        Ser Val His Lys Gln Gln Ala Gly Phe Ser Gln Thr Ser Gln Ile His
                        355                 360                 365
        Lys Lys Asp Ser His Ile Lys Gly Gln Leu Arg Tyr Cys Asp His Lys
                        370                 375                 380
        His Phe Asn Asn Ser Phe Asn Leu Phe Met Ser Thr Ser Pro Phe Tyr
        385                 390                 395                 400
        Pro Met Tyr Ala Ala Leu Asp Val Asn Ala Ala Met Gln Glu Gly Glu
                        405                 410                 415
        Ala Gly Arg Lys Leu Trp His Asp Leu Leu Ile Thr Thr Ile Glu Ala
                        420                 425                 430
        Arg Lys Lys Leu Ile Lys Ala Gly Ser Met Phe Arg Pro Phe Val Pro
                        435                 440                 445
        Pro Val Val Asn Gly Lys Lys Trp Glu Asp Gly Asp Thr Glu Asp Met
        450                 455                 460
        Ala Asn Asn Ile Asp Tyr Trp Arg Phe Glu Lys Gly Ala Lys Trp His
        465                 470                 475                 480
        Ala Tyr Glu Gly Tyr Gly Asp Asn Gln Tyr Tyr Val Asp Pro Asn Lys
                        485                 490                 495
        Phe Met Leu Thr Thr Pro Gly Ile Asn Pro Glu Thr Gly Asp Tyr Glu
                        500                 505                 510
        Asp Phe Gly Val Pro Ala Thr Ile Val Ala Asn Tyr Leu Arg Asp His
                        515                 520                 525
        Gly Ile Ile Pro Glu Lys Ser Asp Leu Asn Ser Ile Leu Phe Leu Met
                        530                 535                 540
        Thr Pro Ala Glu Thr Pro Ala Lys Met Asn Asn Leu Ile Thr Gln Leu
        545                 550                 555                 560
        Leu Gln Leu Gln Arg Leu Ile Glu Glu Asp Ala Pro Leu Lys Gln Val
                        565                 570                 575
```

```
Leu Pro Ser Ile Tyr Ala Ala Asn Glu Glu Arg Tyr Asn Gly Tyr Thr
            580                 585                 590

Ile Arg Glu Leu Cys Gln Glu Leu His Asp Phe Tyr Lys Asn Asn Asn
        595                 600                 605

Thr Phe Thr Tyr Gln Lys Arg Leu Phe Leu Arg Glu Phe Phe Pro Glu
    610                 615                 620

Gln Gly Met Leu Pro Tyr Glu Ala Arg Gln Glu Phe Ile Arg Asn His
625                 630                 635                 640

Asn Lys Leu Val Pro Leu Asn Lys Ile Glu Gly Ile Ala Leu Glu
                645                 650                 655

Gly Ala Leu Pro Tyr Pro Pro Gly Val Phe Cys Val Ala Pro Gly Glu
                660                 665                 670

Lys Trp Ser Glu Thr Ala Val Lys Tyr Phe Thr Ile Leu Gln Asp Gly
                675                 680                 685

Ile Asn Asn Phe Pro Gly Phe Glu Pro Glu Ile Gln Gly Val Tyr Phe
                690                 695                 700

Lys Gln Glu Gly Asp Lys Val Val Leu Tyr Gly Glu Val Tyr Asp Ala
705                 710                 715                 720

Glu Val Ala Lys Asn Asp Asp Arg Tyr Asn Asn
                725                 730

<210> SEQ ID NO 6
<211> LENGTH: 731
<212> TYPE: PRT
<213> ORGANISM: Artificial Sequence
<220> FEATURE:
<223> OTHER INFORMATION: ORNITHINE DECARBOXYLASE MUTANT

<400> SEQUENCE: 6

Met Ser Ser Ser Leu Lys Ile Ala Ser Thr Gln Glu Ala Arg Gln Tyr
1               5                   10                  15

Phe Asp Thr Asp Arg Val Val Val Asp Ala Val Gly Ser Asp Phe Thr
                20                  25                  30

Asp Val Gly Ala Val Ile Ala Met Asp Tyr Glu Thr Asp Val Ile Asp
            35                  40                  45

Ala Ala Asp Ala Thr Lys Phe Gly Ile Pro Val Phe Ala Val Thr Lys
        50                  55                  60

Asp Ala Gln Ala Ile Ser Ala Asp Glu Leu Lys Lys Ile Phe His Ile
65                  70                  75                  80

Ile Asp Leu Glu Asn Lys Phe Asp Ala Thr Val Asn Ala Arg Glu Ile
                85                  90                  95

Glu Thr Ala Val Asn Asn Tyr Glu Asp Ser Ile Leu Pro Pro Phe Phe
                100                 105                 110

Lys Ser Leu Lys Glu Tyr Val Ser Arg Gly Leu Ile Gln Phe Asp Cys
            115                 120                 125

Pro Gly His Gln Gly Gly Gln Tyr Tyr Arg Lys His Pro Ala Gly Arg
        130                 135                 140

Glu Phe Tyr Asp Phe Phe Gly Glu Thr Val Phe Arg Ala Asp Leu Cys
145                 150                 155                 160

Asn Ala Asp Val Ala Leu Gly Asp Leu Leu Ile His Glu Gly Pro Ala
                165                 170                 175

Val Ala Ala Glu Lys His Ala Ala Arg Val Tyr Asn Ala Asp Lys Thr
                180                 185                 190

Tyr Phe Val Leu Gly Gly Ser Ser Asn Ala Asn Asn Thr Val Thr Ser
            195                 200                 205
```

```
Ala Leu Val Ser Asn Gly Asp Leu Val Leu Phe Asp Arg Asn Asn His
    210                 215                 220

Lys Ser Val Tyr Asn Ser Ala Leu Ala Met Ala Gly Gly Arg Pro Val
225                 230                 235                 240

Tyr Leu Gln Thr Asn Arg Asn Pro Tyr Gly Phe Ile Gly Gly Ile Tyr
                245                 250                 255

Asp Ser Asp Phe Asp Glu Lys Lys Ile Arg Glu Leu Ala Ala Lys Val
                260                 265                 270

Asp Pro Glu Arg Ala Lys Trp Lys Arg Pro Phe Arg Leu Ala Val Ile
            275                 280                 285

Gln Leu Gly Thr Tyr Asp Gly Thr Ile Tyr Asn Ala His Glu Val Val
    290                 295                 300

Lys Arg Ile Gly His Leu Cys Asp Tyr Ile Glu Phe Asp Ser Ala Trp
305                 310                 315                 320

Val Gly Tyr Glu Gln Phe Ile Pro Met Met Arg Asn Ser Ser Pro Leu
                325                 330                 335

Leu Ile Asp Asp Leu Gly Pro Glu Asp Pro Gly Ile Ile Val Val Gln
                340                 345                 350

Ser Val His Lys Gln Gln Ala Gly Phe Ser Gln Thr Ser Gln Ile His
            355                 360                 365

Lys Lys Asp Ser His Ile Lys Gly Gln Leu Arg Tyr Cys Asp His Lys
370                 375                 380

His Phe Asn Asn Ser Phe Asn Leu Phe Met Ser Thr Ser Pro Phe Tyr
385                 390                 395                 400

Pro Met Tyr Ala Ala Leu Asp Val Asn Ala Ala Met Gln Glu Gly Glu
                405                 410                 415

Ala Gly Arg Lys Leu Trp His Asp Leu Leu Ile Thr Thr Ile Glu Ala
            420                 425                 430

Arg Lys Lys Leu Ile Lys Ala Gly Ser Met Phe Arg Pro Phe Val Pro
            435                 440                 445

Pro Val Val Asn Gly Lys Lys Trp Glu Asp Gly Asp Thr Glu Asp Met
    450                 455                 460

Ala Asn Asn Ile Asp Tyr Trp Arg Phe Glu Lys Gly Ala Lys Trp His
465                 470                 475                 480

Ala Tyr Glu Gly Tyr Gly Asp Asn Gln Tyr Tyr Val Asp Pro Asn Lys
                485                 490                 495

Phe Met Leu Thr Thr Pro Gly Ile Asn Pro Glu Thr Gly Asp Tyr Glu
                500                 505                 510

Asp Phe Gly Val Pro Ala Thr Ile Val Ala Asn Tyr Leu Arg Asp His
            515                 520                 525

Gly Ile Ile Pro Glu Lys Ser Asp Leu Asn Ser Ile Leu Phe Leu Met
    530                 535                 540

Thr Pro Ala Glu Thr Pro Ala Lys Met Asn Asn Leu Ile Thr Gln Leu
545                 550                 555                 560

Leu Gln Leu Gln Arg Leu Ile Glu Glu Asp Ala Pro Leu Lys Gln Val
                565                 570                 575

Leu Pro Ser Ile Tyr Ala Ala Asn Glu Glu Arg Tyr Asn Gly Tyr Thr
            580                 585                 590

Ile Arg Glu Leu Cys Gln Glu Leu His Asp Phe Tyr Lys Asn Asn Asn
            595                 600                 605

Thr Phe Thr Tyr Gln Lys Arg Leu Phe Leu Arg Glu Phe Phe Pro Glu
610                 615                 620
```

```
Gln Gly Met Leu Pro Tyr Glu Ala Arg Gln Glu Phe Ile Arg Asn His
625                 630                 635                 640

Asn Lys Leu Val Pro Leu Asn Lys Ile Glu Gly Glu Ile Ala Leu Glu
            645                 650                 655

Gly Ala Leu Pro Tyr Pro Pro Gly Val Phe Cys Val Ala Pro Gly Glu
            660                 665                 670

Lys Trp Ser Glu Thr Ala Val Lys Tyr Phe Thr Ile Leu Gln Asp Gly
        675                 680                 685

Ile Asn Asn Phe Pro Gly Phe Ala Pro Glu Ile Gln Gly Gly Tyr Phe
        690                 695                 700

Lys Gln Glu Gly Asp Lys Val Val Leu Tyr Gly Glu Val Tyr Asp Ala
705                 710                 715                 720

Glu Val Ala Lys Asn Asp Asp Arg Tyr Asn Asn
            725                 730

<210> SEQ ID NO 7
<211> LENGTH: 731
<212> TYPE: PRT
<213> ORGANISM: Artificial Sequence
<220> FEATURE:
<223> OTHER INFORMATION: ORNITHINE DECARBOXYLASE MUTANT

<400> SEQUENCE: 7

Met Ser Ser Ser Leu Lys Ile Ala Ser Thr Gln Glu Ala Arg Gln Tyr
1               5                   10                  15

Phe Asp Thr Asp Arg Val Val Asp Ala Val Gly Ser Asp Phe Thr
            20                  25                  30

Asp Val Gly Ala Val Ile Ala Met Asp Tyr Glu Thr Asp Val Ile Asp
            35                  40                  45

Ala Ala Asp Ala Thr Lys Phe Gly Ile Pro Val Phe Ala Val Thr Lys
50                  55                  60

Asp Ala Gln Ala Ile Ser Ala Asp Glu Leu Lys Lys Ile Phe His Ile
65                  70                  75                  80

Ile Asp Leu Glu Asn Lys Phe Asp Ala Thr Val Asn Ala Arg Glu Ile
                85                  90                  95

Glu Thr Ala Val Asn Asn Tyr Glu Asp Ser Ile Leu Pro Pro Phe Phe
            100                 105                 110

Lys Ser Leu Lys Glu Tyr Val Ser Arg Gly Leu Ile Gln Phe Asp Cys
        115                 120                 125

Pro Gly His Gln Gly Gly Gln Tyr Tyr Arg Lys His Pro Ala Gly Arg
    130                 135                 140

Glu Phe Tyr Asp Phe Gly Glu Thr Val Phe Arg Ala Asp Leu Cys
145                 150                 155                 160

Asn Ala Asp Val Ala Leu Gly Asp Leu Leu Ile His Glu Gly Pro Ala
                165                 170                 175

Val Ala Ala Glu Lys His Ala Ala Arg Val Tyr Asn Ala Asp Lys Thr
            180                 185                 190

Tyr Phe Val Leu Gly Gly Ser Ser Asn Ala Asn Thr Val Thr Ser
        195                 200                 205

Ala Leu Val Ser Asn Gly Asp Leu Val Leu Phe Asp Arg Asn Asn His
    210                 215                 220

Lys Ser Val Tyr Asn Ser Ala Leu Ala Met Ala Gly Gly Arg Pro Val
225                 230                 235                 240

Tyr Leu Gln Thr Asn Arg Asn Pro Tyr Gly Phe Ile Gly Gly Ile Tyr
                245                 250                 255
```

-continued

```
Asp Ser Asp Phe Asp Glu Lys Lys Ile Arg Glu Leu Ala Ala Lys Val
            260                 265                 270

Asp Pro Glu Arg Ala Lys Trp Lys Arg Pro Phe Arg Leu Ala Val Ile
        275                 280                 285

Gln Leu Gly Thr Tyr Asp Gly Thr Ile Tyr Asn Ala His Glu Val Val
            290                 295                 300

Lys Arg Ile Gly His Leu Cys Asp Tyr Ile Glu Phe Asp Ser Ala Trp
305                 310                 315                 320

Val Gly Tyr Glu Gln Phe Ile Pro Met Met Arg Asn Ser Ser Pro Leu
                325                 330                 335

Leu Ile Asp Asp Leu Gly Pro Glu Asp Pro Gly Ile Ile Val Val Gln
            340                 345                 350

Ser Val His Lys Gln Gln Ala Gly Phe Ser Gln Thr Ser Gln Ile His
            355                 360                 365

Lys Lys Asp Ser His Ile Lys Gly Gln Leu Arg Tyr Cys Asp His Lys
        370                 375                 380

His Phe Asn Asn Ser Phe Asn Leu Phe Met Ser Thr Ser Pro Phe Tyr
385                 390                 395                 400

Pro Met Tyr Ala Ala Leu Asp Val Asn Ala Ala Met Gln Glu Gly Glu
                405                 410                 415

Ala Gly Arg Lys Leu Trp His Asp Leu Leu Ile Thr Thr Ile Glu Ala
            420                 425                 430

Arg Lys Lys Leu Ile Lys Ala Gly Ser Met Phe Arg Pro Phe Val Pro
        435                 440                 445

Pro Val Val Asn Gly Lys Lys Trp Glu Asp Gly Asp Thr Glu Asp Met
    450                 455                 460

Ala Asn Asn Ile Asp Tyr Trp Arg Phe Glu Lys Gly Ala Lys Trp His
465                 470                 475                 480

Ala Tyr Glu Gly Tyr Gly Asp Asn Gln Tyr Tyr Val Asp Pro Asn Lys
                485                 490                 495

Phe Met Leu Thr Thr Pro Gly Ile Asn Pro Glu Thr Gly Asp Tyr Glu
            500                 505                 510

Asp Phe Gly Val Pro Ala Thr Ile Val Ala Asn Tyr Leu Arg Asp His
        515                 520                 525

Gly Ile Ile Pro Glu Lys Ser Asp Leu Asn Ser Ile Leu Phe Leu Met
    530                 535                 540

Thr Pro Ala Glu Thr Pro Ala Lys Met Asn Asn Leu Ile Thr Gln Leu
545                 550                 555                 560

Leu Gln Leu Gln Arg Leu Ile Glu Glu Asp Ala Pro Leu Lys Gln Val
            565                 570                 575

Leu Pro Ser Ile Tyr Ala Ala Asn Glu Glu Arg Tyr Asn Gly Tyr Thr
            580                 585                 590

Ile Arg Glu Leu Cys Gln Glu Leu His Asp Phe Tyr Lys Asn Asn Asn
        595                 600                 605

Thr Phe Thr Tyr Gln Lys Arg Leu Phe Leu Arg Glu Phe Phe Pro Glu
    610                 615                 620

Gln Gly Met Leu Pro Tyr Glu Ala Arg Gln Glu Phe Ile Arg Asn His
625                 630                 635                 640

Asn Lys Leu Val Pro Leu Asn Lys Ile Glu Gly Ile Ala Leu Glu
                645                 650                 655

Gly Ala Leu Pro Tyr Pro Pro Gly Val Phe Cys Val Ala Pro Gly Glu
            660                 665                 670

Lys Trp Ser Glu Thr Ala Val Lys Tyr Phe Thr Ile Leu Gln Asp Gly
```

```
                    675                 680                 685
Ile Asn Asn Phe Pro Gly Phe Glu Pro Glu Ile Gln Gly Gly Tyr Phe
            690                 695                 700
Lys Gln Glu Gly Asp Lys Val Val Leu Tyr Gly Val Tyr Asp Ala
705                 710                 715                 720
Glu Val Ala Lys Asn Asp Asp Arg Tyr Asn Asn
                725                 730
```

<210> SEQ ID NO 8
<211> LENGTH: 731
<212> TYPE: PRT
<213> ORGANISM: Artificial Sequence
<220> FEATURE:
<223> OTHER INFORMATION: ORNITHINE DECARBOXYLASE MUTANT

<400> SEQUENCE: 8

```
Met Ser Ser Ser Leu Lys Ile Ala Ser Thr Gln Glu Ala Arg Gln Tyr
1               5                   10                  15
Phe Asp Thr Asp Arg Val Val Val Asp Ala Val Gly Ser Asp Phe Thr
                20                  25                  30
Asp Val Gly Ala Val Ile Ala Met Asp Tyr Glu Thr Asp Val Ile Asp
            35                  40                  45
Ala Ala Asp Ala Thr Lys Phe Gly Ile Pro Val Phe Ala Val Thr Lys
    50                  55                  60
Asp Ala Gln Ala Ile Ser Ala Asp Glu Leu Lys Lys Ile Phe His Ile
65                  70                  75                  80
Ile Asp Leu Glu Asn Lys Phe Asp Ala Thr Val Asn Ala Arg Glu Ile
                85                  90                  95
Glu Thr Ala Val Asn Asn Tyr Glu Asp Ser Ile Leu Pro Pro Phe Phe
            100                 105                 110
Lys Ser Leu Lys Glu Tyr Val Ser Arg Gly Leu Ile Gln Phe Asp Cys
        115                 120                 125
Pro Gly His Gln Gly Gly Gln Tyr Tyr Arg Lys His Pro Ala Gly Arg
    130                 135                 140
Glu Phe Tyr Asp Phe Phe Gly Glu Thr Val Phe Arg Ala Asp Leu Cys
145                 150                 155                 160
Asn Ala Asp Val Ala Leu Gly Asp Leu Leu Ile His Glu Gly Pro Ala
                165                 170                 175
Val Ala Ala Glu Lys His Ala Ala Arg Val Tyr Asn Ala Asp Lys Thr
            180                 185                 190
Tyr Phe Val Leu Gly Gly Ser Ser Asn Ala Asn Asn Thr Val Thr Ser
        195                 200                 205
Ala Leu Val Ser Asn Gly Asp Leu Val Leu Phe Asp Arg Asn Asn His
    210                 215                 220
Lys Ser Val Tyr Asn Ser Ala Leu Ala Met Ala Gly Gly Arg Pro Val
225                 230                 235                 240
Tyr Leu Gln Thr Asn Arg Asn Pro Tyr Gly Phe Ile Gly Gly Ile Tyr
                245                 250                 255
Asp Ser Asp Phe Asp Glu Lys Lys Ile Arg Glu Leu Ala Ala Lys Val
            260                 265                 270
Asp Pro Glu Arg Ala Lys Trp Lys Arg Pro Phe Arg Leu Ala Val Ile
        275                 280                 285
Gln Leu Gly Thr Tyr Asp Gly Thr Ile Tyr Asn Ala His Glu Val Val
    290                 295                 300
Lys Arg Ile Gly His Leu Cys Asp Tyr Ile Glu Phe Asp Ser Ala Trp
```

```
            305                 310                 315                 320
Val Gly Tyr Glu Gln Phe Ile Pro Met Met Arg Asn Ser Ser Pro Leu
                    325                 330                 335

Leu Ile Asp Asp Leu Gly Pro Glu Asp Pro Gly Ile Ile Val Val Gln
                340                 345                 350

Ser Val His Lys Gln Gln Ala Gly Phe Ser Gln Thr Ser Gln Ile His
            355                 360                 365

Lys Lys Asp Ser His Ile Lys Gly Gln Leu Arg Tyr Cys Asp His Lys
        370                 375                 380

His Phe Asn Asn Ser Phe Asn Leu Phe Met Ser Thr Ser Pro Phe Tyr
385                 390                 395                 400

Pro Met Tyr Ala Ala Leu Asp Val Asn Ala Ala Met Gln Glu Gly Glu
                405                 410                 415

Ala Gly Arg Lys Leu Trp His Asp Leu Leu Ile Thr Thr Ile Glu Ala
                420                 425                 430

Arg Lys Lys Leu Ile Lys Ala Gly Ser Met Phe Arg Pro Phe Val Pro
                435                 440                 445

Pro Val Val Asn Gly Lys Lys Trp Glu Asp Gly Asp Thr Glu Asp Met
            450                 455                 460

Ala Asn Asn Ile Asp Tyr Trp Arg Phe Glu Lys Gly Ala Lys Trp His
465                 470                 475                 480

Ala Tyr Glu Gly Tyr Gly Asp Asn Gln Tyr Tyr Val Asp Pro Asn Lys
                485                 490                 495

Phe Met Leu Thr Thr Pro Gly Ile Asn Pro Glu Thr Gly Asp Tyr Glu
                500                 505                 510

Asp Phe Gly Val Pro Ala Thr Ile Val Ala Asn Tyr Leu Arg Asp His
            515                 520                 525

Gly Ile Ile Pro Glu Lys Ser Asp Leu Asn Ser Ile Leu Phe Leu Met
        530                 535                 540

Thr Pro Ala Glu Thr Pro Ala Lys Met Asn Asn Leu Ile Thr Gln Leu
545                 550                 555                 560

Leu Gln Leu Gln Arg Leu Ile Glu Glu Asp Ala Pro Leu Lys Gln Val
                565                 570                 575

Leu Pro Ser Ile Tyr Ala Ala Asn Glu Glu Arg Tyr Asn Gly Tyr Thr
                580                 585                 590

Ile Arg Glu Leu Cys Gln Glu Leu His Asp Phe Tyr Lys Asn Asn Asn
            595                 600                 605

Thr Phe Thr Tyr Gln Lys Arg Leu Phe Leu Arg Glu Phe Phe Pro Glu
        610                 615                 620

Gln Gly Met Leu Pro Tyr Glu Ala Arg Gln Glu Phe Ile Arg Asn His
625                 630                 635                 640

Asn Lys Leu Val Pro Leu Asn Lys Ile Glu Gly Ile Ala Leu Glu
                645                 650                 655

Gly Ala Leu Pro Tyr Pro Pro Gly Val Phe Cys Val Ala Pro Gly Glu
                660                 665                 670

Lys Trp Ser Glu Thr Ala Val Lys Tyr Phe Thr Ile Leu Gln Asp Gly
            675                 680                 685

Ile Asn Asn Phe Pro Gly Phe Ala Pro Asp Ile Gln Gly Val Tyr Phe
        690                 695                 700

Lys Gln Glu Gly Asp Lys Val Val Ala Tyr Gly Glu Val Tyr Asp Ala
705                 710                 715                 720

Glu Val Ala Lys Asn Asp Asp Arg Tyr Asn Asn
                725                 730
```

<210> SEQ ID NO 9
<211> LENGTH: 731
<212> TYPE: PRT
<213> ORGANISM: Artificial Sequence
<220> FEATURE:
<223> OTHER INFORMATION: ORNITHINE DECARBOXYLASE MUTANT

<400> SEQUENCE: 9

```
Met Ser Ser Ser Leu Lys Ile Ala Ser Thr Gln Glu Ala Arg Gln Tyr
1               5                   10                  15

Phe Asp Thr Asp Arg Val Val Val Asp Ala Val Gly Ser Asp Phe Thr
            20                  25                  30

Asp Val Gly Ala Val Ile Ala Met Asp Tyr Glu Thr Asp Val Ile Asp
        35                  40                  45

Ala Ala Asp Ala Thr Lys Phe Gly Ile Pro Val Phe Ala Val Thr Lys
50                  55                  60

Asp Ala Gln Ala Ile Ser Ala Asp Glu Leu Lys Lys Ile Phe His Ile
65                  70                  75                  80

Ile Asp Leu Glu Asn Lys Phe Asp Ala Thr Val Asn Ala Arg Glu Ile
                85                  90                  95

Glu Thr Ala Val Asn Asn Tyr Glu Asp Ser Ile Leu Pro Pro Phe Phe
            100                 105                 110

Lys Ser Leu Lys Glu Tyr Val Ser Arg Gly Leu Ile Gln Phe Asp Cys
        115                 120                 125

Pro Gly His Gln Gly Gly Gln Tyr Tyr Arg Lys His Pro Ala Gly Arg
    130                 135                 140

Glu Phe Tyr Asp Phe Phe Gly Glu Thr Val Phe Arg Ala Asp Leu Cys
145                 150                 155                 160

Asn Ala Asp Val Ala Leu Gly Asp Leu Leu Ile His Glu Gly Pro Ala
                165                 170                 175

Val Ala Ala Glu Lys His Ala Ala Arg Val Tyr Asn Ala Asp Lys Thr
            180                 185                 190

Tyr Phe Val Leu Gly Gly Ser Ser Asn Ala Asn Asn Thr Val Thr Ser
        195                 200                 205

Ala Leu Val Ser Asn Gly Asp Leu Val Leu Phe Asp Arg Asn Asn His
210                 215                 220

Lys Ser Val Tyr Asn Ser Ala Leu Ala Met Ala Gly Gly Arg Pro Val
225                 230                 235                 240

Tyr Leu Gln Thr Asn Arg Asn Pro Tyr Gly Phe Ile Gly Gly Ile Tyr
                245                 250                 255

Asp Ser Asp Phe Asp Glu Lys Lys Ile Arg Glu Leu Ala Ala Lys Val
            260                 265                 270

Asp Pro Glu Arg Ala Lys Trp Lys Arg Pro Phe Arg Leu Ala Val Ile
        275                 280                 285

Gln Leu Gly Thr Tyr Asp Gly Thr Ile Tyr Asn Ala His Glu Val Val
    290                 295                 300

Lys Arg Ile Gly His Leu Cys Asp Tyr Ile Glu Phe Asp Ser Ala Trp
305                 310                 315                 320

Val Gly Tyr Glu Gln Phe Ile Pro Met Met Arg Asn Ser Ser Pro Leu
                325                 330                 335

Leu Ile Asp Asp Leu Gly Pro Glu Asp Pro Gly Ile Ile Val Val Gln
            340                 345                 350

Ser Val His Lys Gln Gln Ala Gly Phe Ser Gln Thr Ser Gln Ile His
        355                 360                 365
```

Lys Lys Asp Ser His Ile Lys Gly Gln Leu Arg Tyr Cys Asp His Lys
370                 375                 380

His Phe Asn Asn Ser Phe Asn Leu Phe Met Ser Thr Ser Pro Phe Tyr
385                 390                 395                 400

Pro Met Tyr Ala Ala Leu Asp Val Asn Ala Ala Met Gln Glu Gly Glu
            405                 410                 415

Ala Gly Arg Lys Leu Trp His Asp Leu Leu Ile Thr Thr Ile Glu Ala
            420                 425                 430

Arg Lys Lys Leu Ile Lys Ala Gly Ser Met Phe Arg Pro Phe Val Pro
        435                 440                 445

Pro Val Val Asn Gly Lys Lys Trp Glu Asp Gly Asp Thr Glu Asp Met
450                 455                 460

Ala Asn Asn Ile Asp Tyr Trp Arg Phe Glu Lys Gly Ala Lys Trp His
465                 470                 475                 480

Ala Tyr Glu Gly Tyr Gly Asp Asn Gln Tyr Tyr Val Asp Pro Asn Lys
                485                 490                 495

Phe Met Leu Thr Thr Pro Gly Ile Asn Pro Glu Thr Gly Asp Tyr Glu
            500                 505                 510

Asp Phe Gly Val Pro Ala Thr Ile Val Ala Asn Tyr Leu Arg Asp His
            515                 520                 525

Gly Ile Ile Pro Glu Lys Ser Asp Leu Asn Ser Ile Leu Phe Leu Met
530                 535                 540

Thr Pro Ala Glu Thr Pro Ala Lys Met Asn Asn Leu Ile Thr Gln Leu
545                 550                 555                 560

Leu Gln Leu Gln Arg Leu Ile Glu Glu Asp Ala Pro Leu Lys Gln Val
                565                 570                 575

Leu Pro Ser Ile Tyr Ala Ala Asn Glu Glu Arg Tyr Asn Gly Tyr Thr
            580                 585                 590

Ile Arg Glu Leu Cys Gln Glu Leu His Asp Phe Tyr Lys Asn Asn Asn
        595                 600                 605

Thr Phe Thr Tyr Gln Lys Arg Leu Phe Leu Arg Glu Phe Phe Pro Glu
610                 615                 620

Gln Gly Met Leu Pro Tyr Glu Ala Arg Gln Glu Phe Ile Arg Asn His
625                 630                 635                 640

Asn Lys Leu Val Pro Leu Asn Lys Ile Glu Gly Ile Ala Leu Glu
                645                 650                 655

Gly Ala Leu Pro Tyr Pro Pro Gly Val Phe Cys Val Ala Pro Gly Glu
            660                 665                 670

Lys Trp Ser Glu Thr Ala Val Lys Tyr Phe Thr Ile Leu Gln Asp Gly
        675                 680                 685

Ile Asn Asn Phe Pro Gly Phe Ala Pro Asp Ile Gln Gly Val Tyr Phe
690                 695                 700

Lys Gln Glu Gly Asp Lys Val Val Leu Tyr Gly Glu Val Tyr Asp Ala
705                 710                 715                 720

Glu Val Ala Lys Asn Asp Asp Arg Tyr Asn Asn
                725                 730

<210> SEQ ID NO 10
<211> LENGTH: 2196
<212> TYPE: DNA
<213> ORGANISM: Artificial Sequence
<220> FEATURE:
<223> OTHER INFORMATION: A DNA encoding a amino acid sequences of SEQ ID NO.1

<400> SEQUENCE: 10

```
atgagttctt ctcttaaaat tgcttcgact caagaagcgc gtcaatattt cgatactgac      60
cgcgttgttg tcgatgctgt aggctctgat tttactgatg tcggtgctgt tatcgcaatg     120
gattacgaaa cagatgtcat cgacgctgct gatgcaacta gtttggtat tcctgttttt     180
gccgtaacta aggatgccca agctatcagt gctgatgagc tgaagaagat tttccacatc     240
attgatttgg aaaacaaatt tgatgctact gttaacgctc gtgaaatcga aactgctgtt     300
aacaactacg aagacagcat tttaccacca ttcttcaagt cattgaaaga atacgttagc     360
cgtggtttaa tccaattcga ctgcccaggt caccaaggtg tcaatacta cagaaagcac     420
ccagctggtc gtgaattcta cgacttcttc ggcgaaactg tcttccgtgc agacttatgt     480
aacgctgacg ttgccttggg tgacttgctg atccacgaag tcctgctgt tgctgctgaa     540
aagcatgctg cacgtgttta caacgctgac aagacttact tcgttttagg tggttcttcc     600
aacgctaaca acactgtaac atctgcttta gtttctaacg gcgacttggt attgttcgac     660
cggaacaacc acaagtccgt ttacaactca gctttagcta tggctggtgg ccgtcctgtt     720
tacctccaaa caaaccgtaa cccatacggc ttcatcggtg gtatctacga cagcgacttc     780
gatgaaaaga agatccgtga actggcagct aaggttgacc cagaacgtgc taagtggaag     840
cgtccattcc gtctggctgt tatccaatta ggtacttacg atggtactat ctacaacgca     900
cacgaagttg taaagcgtat cggtcacctt tgtgattaca tcgaattcga ctctgcttgg     960
gtaggttacg aacaattcat tcctatgatg cgtaactctt caccattatt gattgatgac    1020
cttggtccag aagatcctgg tatcattgtt gttcaatcag ttcacaagca acaagccggc    1080
ttctcacaaa cttcacaaat ccacaagaag gatagccaca tcaagggtca attacgttac    1140
tgtgaccaca agcactttaa caactccttc aacttgttca tgtctacttc accattctac    1200
ccaatgtatg cagcattaga cgttaacgct gctatgcaag aaggcgaagc aggtcgcaag    1260
ttatggcatg accttctgat tactaccatt gaagctcgta agaagttgat caaggctggc    1320
tcaatgttcc gtccattcgt tccacctgtt gttaacggca agaagtggga agatggcgac    1380
actgaagata tggctaacaa cattgactac tggcgctttg aaaagggtgc taagtggcat    1440
gcttacgaag gctacggcga caaccaatac tacgttgatc caaacaagtt catgttaact    1500
acacctggta tcaacccaga aactggtgac tacgaagact tcggtgttcc agctactatc    1560
gttgctaact acttacgtga ccacggtatc atccctgaaa agtctgactt gaactctatc    1620
ttgttcttga tgactccagc tgaaactcca gctaagatga caacctgat cactcaactt    1680
cttcaattac aacgcttgat cgaagaagat gctccattga agcaagttct tccttcaatc    1740
tacgctgcta acgaagaacg ttacaatggc tacactatcc gtgaactttg ccaagaattg    1800
cacgacttct acaagaacaa caacacgttc acataccaga agcgtctctt cttacgtgaa    1860
ttcttcccag aacaaggtat gcttccatac gaagctcgtc aagaattcat ccgcaaccac    1920
aacaagcttg ttccattgaa caagatcgaa ggcgaaatcg ccctcgaagg tgctcttcca    1980
taccctccag gagtattctg tgtagcacca ggtgaaaagt ggtcagaaac tgctgttaag    2040
tacttcacta tcttacaaga tggtatcaac aacttccctg gattcgctcc agaaatccaa    2100
ggtgtatact tcaagcaaga aggcgacaag gttgttgctt acggtgaagt ttacgatgca    2160
gaagttgcta agaacgatga tcgttacaac aactaa                              2196
```

<210> SEQ ID NO 11
<211> LENGTH: 2196

<212> TYPE: DNA
<213> ORGANISM: Artificial Sequence
<220> FEATURE:
<223> OTHER INFORMATION: A DNA encoding a amino acid sequences of SEQ ID
      NO.2

<400> SEQUENCE: 11

| | | | | | |
|---|---|---|---|---|---|
| atgagttctt | ctcttaaaat | tgcttcgact | caagaagcgc | gtcaatattt | cgatactgac | 60 |
| cgcgttgttg | tcgatgctgt | aggctctgat | tttactgatg | tcggtgctgt | tatcgcaatg | 120 |
| gattacgaaa | cagatgtcat | cgacgctgct | gatgcaacta | agtttggtat | tcctgttttt | 180 |
| gccgtaacta | aggatgccca | agctatcagt | gctgatgagc | tgaagaagat | tttccacatc | 240 |
| attgatttgg | aaaacaaatt | tgatgctact | gttaacgctc | gtgaaatcga | aactgctgtt | 300 |
| aacaactacg | aagacagcat | tttaccacca | ttcttcaagt | cattgaaaga | atacgttagc | 360 |
| cgtggtttaa | tccaattcga | ctgcccaggt | caccaaggtg | tcaatacta | cagaaagcac | 420 |
| ccagctggtc | gtgaattcta | cgacttcttc | ggcgaaactg | tcttccgtgc | agacttatgt | 480 |
| aacgctgacg | ttgccttggg | tgacttgctg | atccacgaag | tcctgctgt | tgctgctgaa | 540 |
| aagcatgctg | cacgtgttta | caacgctgac | aagacttact | cgtttttagg | tggttcttcc | 600 |
| aacgctaaca | acactgtaac | atctgctta | gtttctaacg | cgacttggt | attgttcgac | 660 |
| cggaacaacc | acaagtccgt | ttacaactca | gctttagcta | tggctggtgg | ccgtcctgtt | 720 |
| tacctccaaa | caaccgtaa | cccatacggc | ttcatcggtg | tatctacga | cagcgacttc | 780 |
| gatgaaaaga | gatccgtga | actggcagct | aaggttgacc | cagaacgtgc | taagtggaag | 840 |
| cgtccattcc | gtctggctgt | tatccaatta | ggtacttacg | atggtactat | ctacaacgca | 900 |
| cacgaagttg | taaagcgtat | cggtcacctt | tgtgattaca | tcgaattcga | ctctgcttgg | 960 |
| gtaggttacg | aacaattcat | tcctatgatg | cgtaactctt | caccattatt | gattgatgac | 1020 |
| cttggtccag | aagatcctgg | tatcattgtt | gttcaatcag | ttcacaagca | acaagccggc | 1080 |
| ttctcacaaa | cttcacaaat | ccacaagaag | gatagccaca | tcaagggtca | attacgttac | 1140 |
| tgtgaccaca | agcactttaa | caactccttc | aacttgttca | tgtctacttc | accattctac | 1200 |
| ccaatgtatg | cagcattaga | cgttaacgct | gctatgcaag | aaggcgaagc | aggtcgcaag | 1260 |
| ttatggcatg | accttctgat | tactaccatt | gaagctcgta | agaagttgat | caaggctggc | 1320 |
| tcaatgttcc | gtccattcgt | tccacctgtt | gttaacggca | agaagtggga | agatggcgac | 1380 |
| actgaagata | tggctaacaa | cattgactac | tggcgctttg | aaaagggtgc | taagtggcat | 1440 |
| gcttacgaag | gctacggcga | caaccaatac | tacgttgatc | aaacaagtt | catgttaact | 1500 |
| acacctggta | tcaacccaga | aactggtgac | tacgaagact | tcggtgttcc | agctactatc | 1560 |
| gttgctaact | acttacgtga | ccacggtatc | atccctgaaa | agtctgactt | gaactctatc | 1620 |
| ttgttcttga | tgactccagc | tgaaactcca | gctaagatga | caacctgat | cactcaactt | 1680 |
| cttcaattac | aacgcttgat | cgaagaagat | gctccattga | agcaagttct | tccttcaatc | 1740 |
| tacgctgcta | acgaagaacg | ttacaatggc | tacactatcc | gtgaactttg | ccaagaattg | 1800 |
| cacgacttct | acaagaacaa | caacacgttc | acataccaga | agcgtctctt | cttacgtgaa | 1860 |
| ttcttcccag | aacaaggtat | gcttccatac | gaagctcgtc | aagaattcat | ccgcaaccac | 1920 |
| aacaagcttg | ttccattgaa | caagatcgaa | ggcgaaatcg | ccctcgaagg | tgctcttcca | 1980 |
| taccctccag | gagtattctg | tgtagcacca | ggtgaaaagt | ggtcagaaac | tgctgttaag | 2040 |
| tacttcacta | tcttacaaga | tggtatcaac | aacttccctg | gattcgaacc | agaaatccaa | 2100 |
| ggtgtatact | tcaagcaaga | aggcgacaag | gttgttgctt | acggtgaagt | ttacgatgca | 2160 |

-continued

| | |
|---|---|
| gaagttgcta agaacgatga tcgttacaac aactaa | 2196 |

<210> SEQ ID NO 12
<211> LENGTH: 2196
<212> TYPE: DNA
<213> ORGANISM: Artificial Sequence
<220> FEATURE:
<223> OTHER INFORMATION: A DNA encoding a amino acid sequences of SEQ ID NO.3

<400> SEQUENCE: 12

| | |
|---|---|
| atgagttctt ctcttaaaat tgcttcgact caagaagcgc gtcaatattt cgatactgac | 60 |
| cgcgttgttg tcgatgctgt aggctctgat tttactgatg tcggtgctgt tatcgcaatg | 120 |
| gattacgaaa cagatgtcat cgacgctgct gatgcaacta agtttggtat tcctgttttt | 180 |
| gccgtaacta aggatgccca agctatcagt gctgatgagc tgaagaagat tttccacatc | 240 |
| attgatttgg aaaacaaatt tgatgctact gttaacgctc gtgaaatcga aactgctgtt | 300 |
| aacaactacg aagacagcat tttaccacca ttcttcaagt cattgaaaga atacgttagc | 360 |
| cgtggtttaa tccaattcga ctgcccaggt caccaaggtg gtcaatacta cagaaagcac | 420 |
| ccagctggtc gtgaattcta cgacttcttc ggcgaaactg tcttccgtgc agacttatgt | 480 |
| aacgctgacg ttgccttggg tgacttgctg atccacgaag gtcctgctgt tgctgctgaa | 540 |
| aagcatgctg cacgtgttta aacgctgac aagacttact tcgttttagg tggttcttcc | 600 |
| aacgctaaca acactgtaac atctgctttta gtttctaacg gcgacttggt attgttcgac | 660 |
| cggaacaacc acaagtccgt ttacaactca gctttagcta tggctggtgg ccgtcctgtt | 720 |
| tacctccaaa caaaccgtaa cccatacggc ttcatcggtg gtatctacga cagcgacttc | 780 |
| gatgaaaaga gatccgtga actggcagct aaggttgacc cagaacgtgc taagtggaag | 840 |
| cgtccattcc gtctggctgt tatccaatta ggtacttacg atggtactat ctacaacgca | 900 |
| cacgaagttg taaagcgtat cggtcacctt tgtgattaca tcgaattcga ctctgcttgg | 960 |
| gtaggttacg aacaattcat tcctatgatg cgtaactctt caccattatt gattgatgac | 1020 |
| cttggtccag aagatcctgg tatcattgtt gttcaatcag ttcacaagca acaagccggc | 1080 |
| ttctcacaaa cttcacaaat ccacaagaag gatagccaca tcaagggtca attacgttac | 1140 |
| tgtgaccaca gcactttaa caactccttc aacttgttca tgtctacttc accattctac | 1200 |
| ccaatgtatg cagcattaga cgttaacgct gctatgcaag aaggcgaagc aggtcgcaag | 1260 |
| ttatggcatg accttctgat tactaccatt gaagctcgta agaagttgat caaggctggc | 1320 |
| tcaatgttcc gtccattcgt tccacctgtt gttaacggca agaagtggga agatggcgac | 1380 |
| actgaagata tggctaacaa cattgactac tggcgctttg aaaagggtgc taagtggcat | 1440 |
| gcttacgaag gctacggcga caaccaatac tacgttgatc caaacaagtt catgttaact | 1500 |
| acacctggta tcaacccaga aactggtgac tacgaagact tcggtgttcc agctactatc | 1560 |
| gttgctaact acttacgtga ccacggtatc atccctgaaa agtctgactt gaactctatc | 1620 |
| ttgttcttga tgactccagc tgaaactcca gctaagatga caacctgat cactcaactt | 1680 |
| cttcaattac aacgcttgat cgaagaagat gctccattga agcaagttct tccttcaatc | 1740 |
| tacgctgcta acgaagaacg ttacaatggc tacactatcc gtgaactttg ccaagaattg | 1800 |
| cacgacttct acaagaacaa caacacgttc acataccaga agcgtctctt cttacgtgaa | 1860 |
| ttcttcccag aacaaggtat gcttccatac gaagctcgtc aagaattcat ccgcaaccac | 1920 |
| aacaagcttg ttccattgaa caagatcgaa ggcgaaatcg ccctcgaagg tgctcttcca | 1980 |

| | |
|---|---|
| taccctccag gagtattctg tgtagcacca ggtgaaaagt ggtcagaaac tgctgttaag | 2040 |
| tacttcacta tcttacaaga tggtatcaac aacttccctg gattcgctcc agaaatccaa | 2100 |
| ggtgggtact tcaagcaaga aggcgacaag gttgttgctt acggtgaagt ttacgatgca | 2160 |
| gaagttgcta gaacgatga tcgttacaac aactaa | 2196 |

```
<210> SEQ ID NO 13
<211> LENGTH: 2196
<212> TYPE: DNA
<213> ORGANISM: Artificial Sequence
<220> FEATURE:
<223> OTHER INFORMATION: A DNA encoding a amino acid sequences of SEQ ID
      NO.4

<400> SEQUENCE: 13
```

| | |
|---|---|
| atgagttctt ctcttaaaat tgcttcgact caagaagcgc gtcaatattt cgatactgac | 60 |
| cgcgttgttg tcgatgctgt aggctctgat tttactgatg tcggtgctgt tatcgcaatg | 120 |
| gattacgaaa cagatgtcat cgacgctgct gatgcaacta agtttggtat tcctgttttt | 180 |
| gccgtaacta aggatgccca agctatcagt gctgatgagc tgaagaagat tttccacatc | 240 |
| attgatttgg aaaacaaatt tgatgctact gttaacgctc gtgaaatcga aactgctgtt | 300 |
| aacaactacg aagacagcat tttaccacca ttcttcaagt cattgaaaga atacgttagc | 360 |
| cgtggtttaa tccaattcga ctgcccaggt caccaaggtg gtcaatacta cagaaagcac | 420 |
| ccagctggtc gtgaattcta cgacttcttc ggcgaaactg tcttccgtgc agacttatgt | 480 |
| aacgctgacg ttgccttggg tgacttgctg atccacgaag gtcctgctgt tgctgctgaa | 540 |
| aagcatgctg cacgtgttta caacgctgac aagacttact tcgtttttagg tggttcttcc | 600 |
| aacgctaaca cactgtaac atctgcttta gtttctaacg cgacttggt attgttcgac | 660 |
| cggaacaacc acaagtccgt ttacaactca gctttagcta tggctggtgg ccgtcctgtt | 720 |
| tacctccaaa caaaccgtaa cccatacggc ttcatcggtg gtatctacga cagcgacttc | 780 |
| gatgaaaaga gatccgtga actggcagct aaggttgacc cagaacgtgc taagtggaag | 840 |
| cgtccattcc gtctggctgt tatccaatta ggtacttacg atggtactat ctacaacgca | 900 |
| cacgaagttg taaagcgtat cggtcacctt tgtgattaca tcgaattcga ctctgcttgg | 960 |
| gtaggttacg aacaattcat tcctatgatg cgtaactctt caccattatt gattgatgac | 1020 |
| cttggtccag aagatcctgg tatcattgtt gttcaatcag ttcacaagca acaagccggc | 1080 |
| ttctcacaaa cttcacaaat ccacaagaag gatagccaca tcaagggtca attacgttac | 1140 |
| tgtgaccaca agcactttaa caactccttc aacttgttca tgtctacttc accattctac | 1200 |
| ccaatgtatg cagcattaga cgttaacgct gctatgcaag aaggcgaagc aggtcgcaag | 1260 |
| ttatggcatg accttctgat tactaccatt gaagctcgta agaagttgat caaggctggc | 1320 |
| tcaatgttcc gtccattcgt tccacctgtt gttaacggca agaagtggga agatggcgac | 1380 |
| actgaagata tggctaacaa cattgactac tggcgctttg aaaagggtgc taagtggcat | 1440 |
| gcttacgaag gctacggcga caaccaatac tacgttgatc aaacaagtt catgttaact | 1500 |
| acacctggta tcaacccaga aactggtgac tacgaagact cggtgttcc agctactatc | 1560 |
| gttgctaact acttacgtga ccacggtatc atccctgaaa agtctgactt gaactctatc | 1620 |
| ttgttcttga tgactccagc tgaaactcca gctaagatga acaacctgat cactcaactt | 1680 |
| cttcaattac aacgcttgat cgaagaagat gctccattga agcaagttct tccttcaatc | 1740 |
| tacgctgcta acgaagaacg ttacaatggc tacactatcc gtgaactttg ccaagaattg | 1800 |

```
cacgacttct acaagaacaa caacacgttc ataccaga agcgtctctt cttacgtgaa    1860
ttcttcccag aacaaggtat gcttccatac gaagctcgtc aagaattcat ccgcaaccac    1920
aacaagcttg ttccattgaa caagatcgaa ggcgaaatcg ccctcgaagg tgctcttcca    1980
taccctccag gagtattctg tgtagcacca ggtgaaaagt ggtcagaaac tgctgttaag    2040
tacttcacta tcttacaaga tggtatcaac aacttccctg gattcgctcc agaaatccaa    2100
ggtgtatact tcaagcaaga aggcgacaag gttgttcttt acggtgaagt ttacgatgca    2160
gaagttgcta agaacgatga tcgttacaac aactaa                              2196
```

<210> SEQ ID NO 14
<211> LENGTH: 2196
<212> TYPE: DNA
<213> ORGANISM: Artificial Sequence
<220> FEATURE:
<223> OTHER INFORMATION: A DNA encoding a amino acid sequences of SEQ ID
NO.5

<400> SEQUENCE: 14

```
atgagttctt ctcttaaaat tgcttcgact caagaagcgc gtcaatattt cgatactgac    60
cgcgttgttg tcgatgctgt aggctctgat tttactgatg tcggtgctgt tatcgcaatg    120
gattacgaaa cagatgtcat cgacgctgct gatgcaacta gtttggtat tcctgttttt    180 gccgtaacta aggatgccca gctatcagt gctgatgagc tgaagaagat tttccacatc    240
attgatttgg aaaacaaatt tgatgctact gttaacgctc gtgaaatcga actgctgtt    300 aacaactacg aagacagcat tttaccacca ttcttcaagt cattgaaaga atacgttagc    360
cgtggtttaa tccaattcga ctgcccaggt caccaaggtg gtcaatacta cagaaagcac    420
ccagctggtc gtgaattcta cgacttcttc ggcgaaactg tcttccgtgc agacttatgt    480
aacgctgacg ttgccttggg tgacttgctg atccacgaag gtcctgctgt tgctgctgaa    540
aagcatgctg cacgtgttta caacgctgac aagacttact tcgttttagg tggttcttcc    600
aacgctaaca acactgtaac atctgcttta gtttctaacg gcgacttggt attgttcgac    660
cggaacaacc acaagtccgt ttacaactca gctttagcta tggctggtgg ccgtcctgtt    720
tacctccaaa caaaccgtaa cccatacggc ttcatcggtg gtatctacga cagcgacttc    780
gatgaaaaga gatccgtga actggcagct aaggttgacc cagaacgtgc taagtggaag    840
cgtccattcc gtctggctgt tatccaatta ggtacttacg atggtactat ctacaacgca    900
cacgaagttg taaagcgtat cggtcaccct tgtgattaca tcgaattcga ctctgcttgg    960
gtaggttacg aacaattcat tcctatgatg cgtaactctt caccattatt gattgatgac    1020
cttggtccag aagatcctgg tatcattgtt gttcaatcag ttcacaagca acaagccggc    1080
ttctcacaaa cttcacaaat ccacaagaag gatagccaca tcaagggtca attacgttac    1140
tgtgaccaca gcactttaa caactccttc aacttgttca tgtctacttc accattctac    1200
ccaatgtatg cagcattaga cgttaacgct gctatgcaag aaggcgaagc aggtcgcaag    1260
ttatggcatg accttctgat tactaccatt gaagctcgta agaagttgat caaggctggc    1320
tcaatgttcc gtccattcgt tccacctgtt gttaacggca agaagtggga agatggcgac    1380
actgaagata tggctaacaa cattgactac tggcgctttg aaaagggtgc taagtggcat    1440
gcttacgaag gctacggcga caaccaatac tacgttgatc aaacaagtt catgttaact    1500 acacctggta tcaacccaga aactggtgac tacgaagact tcggtgttcc agctactatc    1560
gttgctaact acttacgtga ccacggtatc atccctgaaa agtctgactt gaactctatc    1620
```

```
ttgttcttga tgactccagc tgaaactcca gctaagatga acaacctgat cactcaactt    1680
cttcaattac aacgcttgat cgaagaagat gctccattga agcaagttct tccttcaatc    1740
tacgctgcta acgaagaacg ttacaatggc tacactatcc gtgaactttg ccaagaattg    1800
cacgacttct acaagaacaa caacacgttc acataccaga agcgtctctt cttacgtgaa    1860
ttcttcccag aacaaggtat gcttccatac gaagctcgtc aagaattcat ccgcaaccac    1920
aacaagcttt tccattgaa caagatcgaa ggcgaaatcg ccctcgaagg tgctcttcca    1980
taccctccag gagtattctg tgtagcacca ggtgaaaagt ggtcagaaac tgctgttaag    2040
tacttcacta tcttcacaaga tggtatcaac aacttccctg gattcgaacc agaaatccaa    2100
ggtgtatact tcaagcaaga aggcgacaag gttgttcttt acggtgaagt ttacgatgca    2160
gaagttgcta agaacgatga tcgttacaac aactaa                              2196
```

<210> SEQ ID NO 15
<211> LENGTH: 2196
<212> TYPE: DNA
<213> ORGANISM: Artificial Sequence
<220> FEATURE:
<223> OTHER INFORMATION: A DNA encoding a amino acid sequences of SEQ ID NO.6

<400> SEQUENCE: 15

```
atgagttctt ctcttaaaat tgcttcgact caagaagcgc gtcaatattt cgatactgac     60
cgcgttgttg tcgatgctgt aggctctgat tttactgatg tcggtgctgt tatcgcaatg    120
gattacgaaa cagatgtcat cgacgctgct gatgcaacta agtttggtat tcctgttttt    180
gccgtaacta aggatgccca agctatcagt gctgatgagc tgaagaagat tttccacatc    240
attgatttgg aaaacaaatt tgatgctact gttaacgctc gtgaaatcga actgctgtt    300 aacaactacg aagacagcat tttaccacca ttcttcaagt cattgaaaga atacgttagc    360 cgtggttta tccaattcga ctgcccaggt caccaaggtg gtcaatacta cagaaagcac    420
ccagctggtc gtgaattcta cgacttcttc ggcgaaactg tcttcgtgc agacttatgt    480 aacgctgacg ttgccttggg tgacttgctg atccacgaag gtcctgctgt gctgctgaa    540 aagcatgctg cacgtgttta caacgctgac aagacttact tcgttttagg tggttcttcc    600
aacgctaaca acactgtaac atctgcttta gtttctaacg gcgacttggt attgttcgac    660
cggaacaacc acaagtccgt ttacaactca gctttagcta tggctggtgg ccgtcctgtt    720
tacctccaaa caaaccgtaa cccatacggc ttcatcggtg gtatctacga cagcgacttc    780
gatgaaaaga agatccgtga actggcagct aaggttgacc cagaacgtgc taagtggaag    840
cgtccattcc gtctggctgt tatccaatta ggtacttacg atggtactat ctacaacgca    900
cacgaagttg taaagcgtat cggtcacctt tgtgattaca tcgaattcga ctctgcttgg    960
gtaggttacg aacaattcat tcctatgatg cgtaactctt caccattatt gattgatgac   1020
cttggtccag aagatcctgg tatcattgtt gttcaatcag ttcacaagca acaagccggc   1080
ttctcacaaa cttcacaaat ccacaagaag gatagccaca tcaagggtca attacgttac   1140
tgtgaccaca agcactttaa caactccttc aacttgttca tgtctacttc accattctac   1200
ccaatgtatg cagcattaga cgttaacgct gctatgcaag aaggcgaagc aggtcgcaag   1260 ttatgggcatg accttctgat tactaccatt gaagctcgta agaagttgat caaggctggc   1320
tcaatgttcc gtccattcgt tccacctgtt gttaacggca agaagtggga agatggcgac   1380
actgaagata tggctaacaa cattgactac tggcgctttg aaaagggtgc taagtggcat   1440
```

```
gcttacgaag gctacggcga caaccaatac tacgttgatc caaacaagtt catgttaact    1500
acacctggta tcaacccaga aactggtgac tacgaagact tcggtgttcc agctactatc    1560
gttgctaact acttacgtga ccacggtatc atccctgaaa agtctgactt gaactctatc    1620
ttgttcttga tgactccagc tgaaactcca gctaagatga caacctgat cactcaactt     1680 cttcaattac aacgcttgat cgaagaagat gctccattga agcaagttct tccttcaatc    1740
tacgctgcta acgaagaacg ttacaatggc tacactatcc gtgaactttg ccaagaattg    1800
cacgacttct acaagaacaa caacacgttc ataccagaa gcgtctctt cttacgtgaa      1860 ttcttcccag aacaaggtat gcttccatac gaagctcgtc aagaattcat ccgcaaccac    1920
aacaagcttg ttccattgaa caagatcgaa ggcgaaatcg ccctcgaagg tgctcttcca    1980
taccctccag gagtattctg tgtagcacca ggtgaaaagt ggtcagaaac tgctgttaag    2040
tacttcacta tcttacaaga tggtatcaac aacttccctg gattcgctcc agaaatccaa    2100
ggtgggtact tcaagcaaga aggcgacaag gttgttcttt acggtgaagt ttacgatgca    2160
gaagttgcta agaacgatga tcgttacaac aactaa                              2196
```

<210> SEQ ID NO 16
<211> LENGTH: 2196
<212> TYPE: DNA
<213> ORGANISM: Artificial Sequence
<220> FEATURE:
<223> OTHER INFORMATION: A DNA encoding a amino acid sequences of SEQ ID NO.7

<400> SEQUENCE: 16

```
atgagttctt ctcttaaaat tgcttcgact caagaagcgc gtcaatattt cgatactgac     60
cgcgttgttg tcgatgctgt aggctctgat tttactgatg tcggtgctgt tatcgcaatg    120
gattacgaaa cagatgtcat cgacgctgct gatgcaacta agtttggtat tcctgttttt    180
gccgtaacta aggatgccca agctatcagt gctgatgagc tgaagaagat tttccacatc    240
attgatttgg aaaacaaatt tgatgctact gttaacgctc gtgaaatcga aactgctgtt    300
aacaactacg aagacagcat tttaccacca ttcttcaagt cattgaaaga atacgttagc    360
cgtggtttaa tccaattcga ctgcccaggt caccaaggtg gtcaatacta cagaaagcac    420
ccagctggtc gtgaattcta cgacttcttc ggcgaaactg tcttccgtgc agacttatgt    480
aacgctgacg ttgccttggg tgacttgctg atccacgaag gtcctgctgt tgctgctgaa    540
aagcatgctg cacgtgttta caacgctgac aagacttact tcgttttagg tggttcttcc    600
aacgctaaca cactgtaac atctgcttta gtttctaacg gcgacttggt attgttcgac    660
cggaacaacc acaagtccgt ttacaactca gctttagcta tggctggtgg ccgtcctgtt    720
tacctccaaa caaaccgtaa cccatacggc ttcatcggtg gtatctacga cagcgacttc    780
gatgaaaaga gatccgtga actggcagct aaggttgacc cagaacgtgc taagtggaag    840
cgtccattcc gtctggctgt tatccaatta ggtacttacg atggtactat ctacaacgca    900
cacgaagttg taaagcgtat cggtcacctt tgtgattaca tcgaattcga ctctgcttgg    960
gtaggttacg aacaattcat tcctatgatg cgtaactctt caccattatt gattgatgac    1020
cttggtccag aagatcctgg tatcattgtt gttcaatcag ttcacaagca acaagccggc    1080
ttctcacaaa cttcacaaat ccacaagaag gatagccaca tcaagggtca attacgttac    1140
tgtgaccaca agcactttaa caactccttc aacttgttca tgtctacttc accattctac    1200
ccaatgtatg cagcattaga cgttaacgct gctatgcaag aaggcgaagc aggtcgcaag    1260
```

```
ttatggcatg accttctgat tactaccatt gaagctcgta agaagttgat caaggctggc    1320
tcaatgttcc gtccattcgt tccacctgtt gttaacggca agaagtggga agatggcgac    1380
actgaagata tggctaacaa cattgactac tggcgctttg aaaagggtgc taagtggcat    1440
gcttacgaag gctacggcga caaccaatac tacgttgatc aaacaagtt catgttaact     1500 acacctggta tcaacccaga aactggtgac tacgaagact tcggtgttcc agctactatc    1560
gttgctaact acttacgtga ccacggtatc atccctgaaa agtctgactt gaactctatc    1620
ttgttcttga tgactccagc tgaaactcca gctaagatga caacctgat cactcaactt     1680 cttcaattac aacgcttgat cgaagaagat gctccattga agcaagttct tccttcaatc    1740
tacgctgcta acgaagaacg ttacaatggc tacactatcc gtgaactttg ccaagaattg    1800
cacgacttct acaagaacaa caacacgttc ataccagag agcgtctctt cttacgtgaa     1860
ttcttcccag aacaaggtat gcttccatac gaagctcgtc aagaattcat ccgcaaccac    1920
aacaagcttt tccattgaa caagatcgaa ggcgaaatcg ccctcgaagg tgctcttcca     1980
taccctccag gagtattctg tgtagcacca ggtgaaaagt ggtcagaaac tgctgttaag    2040
tacttcacta tcttacaaga tggtatcaac aacttccctg gattcgaacc agaaatccaa    2100
ggtgggtact tcaagcaaga aggcgacaag gttgttcttt acggtgaagt ttacgatgca    2160
gaagttgcta agaacgatga tcgttacaac aactaa                              2196

<210> SEQ ID NO 17
<211> LENGTH: 2196
<212> TYPE: DNA
<213> ORGANISM: Artificial Sequence
<220> FEATURE:
<223> OTHER INFORMATION: A DNA encoding a amino acid sequences of SEQ ID
      NO.8

<400> SEQUENCE: 17
atgagttctt ctcttaaaat tgcttcgact caagaagcgc gtcaatattt cgatactgac      60
cgcgttgttg tcgatgctgt aggctctgat tttactgatg tcggtgctgt tatcgcaatg     120
gattacgaaa cagatgtcat cgacgctgct gatgcaacta agtttggtat tcctgttttt     180
gccgtaacta aggatgccca agctatcagt gctgatgagc tgaagaagat tttccacatc     240
attgatttgg aaaacaaatt tgatgctact gttaacgctc gtgaaatcga aactgctgtt     300
aacaactacg aagacagcat tttaccacca ttcttcaagt cattgaaaga atacgttagc     360
cgtggtttaa tccaattcga ctgcccaggt caccaaggtg gtcaatacta cagaaagcac    420
ccagctggtc gtgaattcta cgacttcttc ggcgaaactg tcttccgtgc agacttatgt    480
aacgctgacg ttgccttggg tgacttgctg atccacgaag gtcctgctgt tgctgctgaa    540
aagcatgctg cacgtgttta caacgctgac aagacttact tcgttttagg tggttcttcc    600
aacgctaaca cactgtaac atctgcttta gtttctaacg gcgacttggt attgttcgac    660
cggaacaacc acaagtccgt ttacaactca gctttagcta tggctggtgg ccgtcctgtt    720
tacctccaaa caaaccgtaa cccatacggc ttcatcggtg gtatctacga cagcgacttc    780
gatgaaaaga gatccgtga actggcagct aaggttgacc cagaacgtgc taagtggaag     840
cgtccattcc gtctggctgt tatccaatta ggtacttacg atggtactat ctacaacgca    900
cacgaagttg taaagcgtat cggtcacctt tgtgattaca tcgaattcga ctctgcttgg    960
gtaggttacg aacaattcat tcctatgatg cgtaactctt caccattatt gattgatgac    1020
cttggtccag aagatcctgg tatcattgtt gttcaatcag ttcacaagca acaagccggc    1080
```

```
ttctcacaaa cttcacaaat ccacaagaag gatagccaca tcaagggtca attacgttac   1140
tgtgaccaca agcactttaa caactccttc aacttgttca tgtctacttc accattctac   1200
ccaatgtatg cagcattaga cgttaacgct gctatgcaag aaggcgaagc aggtcgcaag   1260
ttatggcatg accttctgat tactaccatt gaagctcgta agaagttgat caaggctggc   1320
tcaatgttcc gtccattcgt tccacctgtt gttaacggca agaagtggga agatggcgac   1380
actgaagata tggctaacaa cattgactac tggcgctttg aaaagggtgc taagtggcat   1440
gcttacgaag gctacggcga caaccaatac tacgttgatc caaacaagtt catgttaact   1500
acacctggta tcaacccaga aactggtgac tacgaagact tcggtgttcc agctactatc   1560
gttgctaact acttacgtga ccacggtatc atccctgaaa agtctgactt gaactctatc   1620
ttgttcttga tgactccagc tgaaactcca gctaagatga caacctgat cactcaactt    1680 cttcaattac aacgcttgat cgaagaagat gctccattga agcaagttct tccttcaatc   1740
tacgctgcta acgaagaacg ttacaatggc tacactatcc gtgaactttg ccaagaattg   1800
cacgacttct acaagaacaa caacacgttc acataccaga agcgtctctt cttacgtgaa   1860
ttcttcccag aacaaggtat gcttccatac gaagctcgtc aagaattcat ccgcaaccac   1920
aacaagcttg ttccattgaa caagatcgaa ggcgaaatcg ccctcgaagg tgctcttcca   1980
taccctccag gagtattctg tgtagcacca ggtgaaaagt ggtcagaaac tgctgttaag   2040
tacttcacta tcttacaaga tggtatcaac aacttccctg gattcgctcc agatatccaa   2100
ggtgtatact tcaagcaaga aggcgacaag gttgttgctt acggtgaagt ttacgatgca   2160
gaagttgcta agaacgatga tcgttacaac aactaa                             2196
```

<210> SEQ ID NO 18
<211> LENGTH: 2196
<212> TYPE: DNA
<213> ORGANISM: Artificial Sequence
<220> FEATURE:
<223> OTHER INFORMATION: A DNA encoding a amino acid sequences of SEQ ID
      NO.9

<400> SEQUENCE: 18

```
atgagttctt ctcttaaaat tgcttcgact caagaagcgc gtcaatattt cgatactgac    60
cgcgttgttg tcgatgctgt aggctctgat tttactgatg tcggtgctgt tatcgcaatg   120
gattacgaaa cagatgtcat cgacgctgct gatgcaacta agtttggtat tcctgttttt   180
gccgtaacta aggatgccca agctatcagt gctgatgagc tgaagaagat tttccacatc   240
attgatttgg aaaacaaatt tgatgctact gttaacgctc gtgaaatcga aactgctgtt   300
aacaactacg aagacagcat tttaccacca ttcttcaagt cattgaaaga atacgttagc   360
cgtggtttaa tccaattcga ctgcccaggt caccaaggtg gtcaatacta cagaaagcac   420
ccagctggtc gtgaattcta cgacttcttc ggcgaaactg tcttccgtgc agacttatgt   480
aacgctgacg ttgccttggg tgacttgctg atccacgaag gtcctgctgt tgctgctgaa   540
aagcatgctg cacgtgttta caacgctgac aagacttact tcgttttagg tggttcttcc   600
aacgctaaca cactgtaac atctgcttta gtttctaacg cgacttggt attgttcgac   660 cggaacaacc acaagtccgt ttacaactca gctttagcta tggctggtgg ccgtcctgtt   720
tacctccaaa caaaccgtaa cccatacggc ttcatcggtg gtatctacga cagcgacttc   780
gatgaaaaga gatccgtga actggcagct aaggttgacc cagaacgtgc taagtggaag   840
cgtccattcc gtctggctgt tatccaatta ggtacttacg atggtactat ctacaacgca   900
```

```
cacgaagttg taaagcgtat cggtcacctt tgtgattaca tcgaattcga ctctgcttgg    960
gtaggttacg aacaattcat tcctatgatg cgtaactctt caccattatt gattgatgac   1020
cttggtccag aagatcctgg tatcattgtt gttcaatcag ttcacaagca acaagccggc   1080
ttctcacaaa cttcacaaat ccacaagaag gatagccaca tcaagggtca attacgttac   1140
tgtgaccaca agcactttaa caactccttc aacttgttca tgtctacttc accattctac   1200
ccaatgtatg cagcattaga cgttaacgct gctatgcaag aaggcgaagc aggtcgcaag   1260
ttatggcatg accttctgat tactaccatt gaagctcgta agaagttgat caaggctggc   1320
tcaatgttcc gtccattcgt tccacctgtt gttaacggca agaagtggga agatggcgac   1380
actgaagata tggctaacaa cattgactac tggcgctttg aaaagggtgc taagtggcat   1440
gcttacgaag gctacggcga caaccaatac tacgttgatc aaacaagtt catgttaact   1500
acacctggta tcaacccaga aactggtgac tacgaagact tcggtgttcc agctactatc   1560
gttgctaact acttacgtga ccacggtatc atccctgaaa agtctgactt gaactctatc   1620
ttgttcttga tgactccagc tgaaactcca gctaagatga caacctgat cactcaactt   1680
cttcaattac aacgcttgat cgaagaagat gctccattga agcaagttct tccttcaatc   1740
tacgctgcta acgaagaacg ttacaatggc tacactatcc gtgaactttg ccaagaattg   1800
cacgacttct acaagaacaa caacacgttc atacaccaga agcgtctctt cttacgtgaa   1860
ttcttcccag aacaaggtat gcttccatac gaagctcgtc aagaattcat ccgcaaccac   1920
aacaagcttg ttccattgaa caagatcgaa ggcgaaatcg ccctcgaagg tgctcttcca   1980
tacccctccag gagtattctg tgtagcacca ggtgaaaagt ggtcagaaac tgctgttaag   2040
tacttcacta tcttacaaga tggtatcaac aacttccctg gattcgctcc agatatccaa   2100
ggtgtatact tcaagcaaga aggcgacaag gttgttcttt acggtgaagt ttacgatgca   2160
gaagttgcta agaacgatga tcgttacaac aactaa                             2196
```

<210> SEQ ID NO 19
<211> LENGTH: 731
<212> TYPE: PRT
<213> ORGANISM: Artificial Sequence
<220> FEATURE:
<223> OTHER INFORMATION: ORNITHINE DECARBOXYLASE MUTANT

<400> SEQUENCE: 19

```
Met Ser Ser Ser Leu Lys Ile Ala Ser Thr Gln Glu Ala Arg Gln Tyr
1               5                   10                  15

Phe Asp Thr Asp Arg Val Val Val Asp Ala Val Gly Ser Asp Phe Thr
                20                  25                  30

Asp Val Gly Ala Val Ile Ala Met Asp Tyr Glu Thr Asp Val Ile Asp
            35                  40                  45

Ala Ala Asp Ala Thr Lys Phe Gly Ile Pro Val Phe Ala Val Thr Lys
        50                  55                  60

Asp Ala Gln Ala Ile Ser Ala Asp Glu Leu Lys Lys Ile Phe His Ile
65                  70                  75                  80

Ile Asp Leu Glu Asn Lys Phe Asp Ala Thr Val Asn Ala Arg Glu Ile
                85                  90                  95

Glu Thr Ala Val Asn Asn Tyr Glu Asp Ser Ile Leu Pro Pro Phe Phe
                100                 105                 110

Lys Ser Leu Lys Glu Tyr Val Ser Arg Gly Leu Ile Gln Phe Asp Cys
            115                 120                 125
```

Pro Gly His Gln Gly Gly Gln Tyr Tyr Arg Lys His Pro Ala Gly Arg
130                 135                 140

Glu Phe Tyr Asp Phe Phe Gly Glu Thr Val Phe Arg Ala Asp Leu Cys
145                 150                 155                 160

Asn Ala Asp Val Ala Leu Gly Asp Leu Leu Ile His Glu Gly Pro Ala
                165                 170                 175

Val Ala Ala Glu Lys His Ala Ala Arg Val Tyr Asn Ala Asp Lys Thr
            180                 185                 190

Tyr Phe Val Leu Gly Gly Ser Ser Asn Ala Asn Asn Thr Val Thr Ser
        195                 200                 205

Ala Leu Val Ser Asn Gly Asp Leu Val Leu Phe Asp Arg Asn Asn His
    210                 215                 220

Lys Ser Val Tyr Asn Ser Ala Leu Ala Met Ala Gly Arg Pro Val
225                 230                 235                 240

Tyr Leu Gln Thr Asn Arg Asn Pro Tyr Gly Phe Ile Gly Ile Tyr
                245                 250                 255

Asp Ser Asp Phe Asp Glu Lys Lys Ile Arg Glu Leu Ala Ala Lys Val
            260                 265                 270

Asp Pro Glu Arg Ala Lys Trp Lys Arg Pro Phe Arg Leu Ala Val Ile
    275                 280                 285

Gln Leu Gly Thr Tyr Asp Gly Thr Ile Tyr Asn Ala His Glu Val Val
    290                 295                 300

Lys Arg Ile Gly His Leu Cys Asp Tyr Ile Glu Phe Asp Ser Ala Trp
305                 310                 315                 320

Val Gly Tyr Glu Gln Phe Ile Pro Met Met Arg Asn Ser Ser Pro Leu
                325                 330                 335

Leu Ile Asp Asp Leu Gly Pro Glu Asp Pro Gly Ile Ile Val Val Gln
            340                 345                 350

Ser Val His Lys Gln Gln Ala Gly Phe Ser Gln Thr Ser Gln Ile His
    355                 360                 365

Lys Lys Asp Ser His Ile Lys Gly Gln Leu Arg Tyr Cys Asp His Lys
370                 375                 380

His Phe Asn Asn Ser Phe Asn Leu Phe Met Ser Thr Ser Pro Phe Tyr
385                 390                 395                 400

Pro Met Tyr Ala Ala Leu Asp Val Asn Ala Ala Met Gln Glu Gly Glu
                405                 410                 415

Ala Gly Arg Lys Leu Trp His Asp Leu Leu Ile Thr Thr Ile Glu Ala
            420                 425                 430

Arg Lys Lys Leu Ile Lys Ala Gly Ser Met Phe Arg Pro Phe Val Pro
    435                 440                 445

Pro Val Val Asn Gly Lys Lys Trp Glu Asp Gly Asp Thr Glu Asp Met
    450                 455                 460

Ala Asn Asn Ile Asp Tyr Trp Arg Phe Glu Lys Gly Ala Lys Trp His
465                 470                 475                 480

Ala Tyr Glu Gly Tyr Gly Asp Asn Gln Tyr Tyr Val Asp Pro Asn Lys
                485                 490                 495

Phe Met Leu Thr Thr Pro Gly Ile Asn Pro Glu Thr Gly Asp Tyr Glu
            500                 505                 510

Asp Phe Gly Val Pro Ala Thr Ile Val Ala Asn Tyr Leu Arg Asp His
    515                 520                 525

Gly Ile Ile Pro Glu Lys Ser Asp Leu Asn Ser Ile Leu Phe Leu Met
530                 535                 540

Thr Pro Ala Glu Thr Pro Ala Lys Met Asn Asn Leu Ile Thr Gln Leu

```
             545                 550                 555                 560
Leu Gln Leu Gln Arg Leu Ile Glu Glu Asp Ala Pro Leu Lys Gln Val
                 565                 570                 575
Leu Pro Ser Ile Tyr Ala Ala Asn Glu Glu Arg Tyr Asn Gly Tyr Thr
                 580                 585                 590
Ile Arg Glu Leu Cys Gln Glu Leu His Asp Phe Tyr Lys Asn Asn Asn
                 595                 600                 605
Thr Phe Thr Tyr Gln Lys Arg Leu Phe Leu Arg Glu Phe Phe Pro Glu
                 610                 615                 620
Gln Gly Met Leu Pro Tyr Glu Ala Arg Gln Glu Phe Ile Arg Asn His
625                 630                 635                 640
Asn Lys Leu Val Pro Leu Asn Lys Ile Glu Gly Ile Ala Leu Glu
                 645                 650                 655
Gly Ala Leu Pro Tyr Pro Pro Gly Val Phe Cys Val Ala Pro Gly Glu
                 660                 665                 670
Lys Trp Ser Glu Thr Ala Val Lys Tyr Phe Thr Ile Leu Gln Asp Gly
                 675                 680                 685
Ile Asn Asn Phe Pro Gly Phe Ala Pro Glu Ile Gln Gly Val Tyr Phe
                 690                 695                 700
Lys Gln Glu Gly Asp Lys Val Val Val Tyr Gly Glu Val Tyr Asp Ala
705                 710                 715                 720
Glu Val Ala Lys Asn Asp Asp Arg Tyr Asn Asn
                 725                 730

<210> SEQ ID NO 20
<211> LENGTH: 731
<212> TYPE: PRT
<213> ORGANISM: Artificial Sequence
<220> FEATURE:
<223> OTHER INFORMATION: ORNITHINE DECARBOXYLASE MUTANT

<400> SEQUENCE: 20

Met Ser Ser Ser Leu Lys Ile Ala Ser Thr Gln Glu Ala Arg Gln Tyr
1               5                   10                  15
Phe Asp Thr Asp Arg Val Val Val Asp Ala Val Gly Ser Asp Phe Thr
                 20                  25                  30
Asp Val Gly Ala Val Ile Ala Met Asp Tyr Glu Thr Asp Val Ile Asp
                 35                  40                  45
Ala Ala Asp Ala Thr Lys Phe Gly Ile Pro Val Phe Ala Val Thr Lys
             50                  55                  60
Asp Ala Gln Ala Ile Ser Ala Asp Glu Leu Lys Lys Ile Phe His Ile
65              70                  75                  80
Ile Asp Leu Glu Asn Lys Phe Asp Ala Thr Val Asn Ala Arg Glu Ile
                 85                  90                  95
Glu Thr Ala Val Asn Asn Tyr Glu Asp Ser Ile Leu Pro Pro Phe Phe
                 100                 105                 110
Lys Ser Leu Lys Glu Tyr Val Ser Arg Gly Leu Ile Gln Phe Asp Cys
             115                 120                 125
Pro Gly His Gln Gly Gly Gln Tyr Tyr Arg Lys His Pro Ala Gly Arg
             130                 135                 140
Glu Phe Tyr Asp Phe Phe Gly Glu Thr Val Phe Arg Ala Asp Leu Cys
145                 150                 155                 160
Asn Ala Asp Val Ala Leu Gly Asp Leu Leu Ile His Glu Gly Pro Ala
                 165                 170                 175
Val Ala Ala Glu Lys His Ala Ala Arg Val Tyr Asn Ala Asp Lys Thr
```

```
            180                 185                 190
Tyr Phe Val Leu Gly Gly Ser Ser Asn Ala Asn Asn Thr Val Thr Ser
            195                 200                 205
Ala Leu Val Ser Asn Gly Asp Leu Val Leu Phe Asp Arg Asn Asn His
            210                 215                 220
Lys Ser Val Tyr Asn Ser Ala Leu Ala Met Ala Gly Gly Arg Pro Val
225                 230                 235                 240
Tyr Leu Gln Thr Asn Arg Asn Pro Tyr Gly Phe Ile Gly Gly Ile Tyr
            245                 250                 255
Asp Ser Asp Phe Asp Glu Lys Lys Ile Arg Glu Leu Ala Ala Lys Val
            260                 265                 270
Asp Pro Glu Arg Ala Lys Trp Lys Arg Pro Phe Arg Leu Ala Val Ile
            275                 280                 285
Gln Leu Gly Thr Tyr Asp Gly Thr Ile Tyr Asn Ala His Glu Val Val
            290                 295                 300
Lys Arg Ile Gly His Leu Cys Asp Tyr Ile Glu Phe Asp Ser Ala Trp
305                 310                 315                 320
Val Gly Tyr Glu Gln Phe Ile Pro Met Met Arg Asn Ser Ser Pro Leu
            325                 330                 335
Leu Ile Asp Asp Leu Gly Pro Glu Asp Pro Gly Ile Ile Val Val Gln
            340                 345                 350
Ser Val His Lys Gln Gln Ala Gly Phe Ser Gln Thr Ser Gln Ile His
            355                 360                 365
Lys Lys Asp Ser His Ile Lys Gly Gln Leu Arg Tyr Cys Asp His Lys
            370                 375                 380
His Phe Asn Asn Ser Phe Asn Leu Phe Met Ser Thr Ser Pro Phe Tyr
385                 390                 395                 400
Pro Met Tyr Ala Ala Leu Asp Val Asn Ala Ala Met Gln Glu Gly Glu
            405                 410                 415
Ala Gly Arg Lys Leu Trp His Asp Leu Leu Ile Thr Thr Ile Glu Ala
            420                 425                 430
Arg Lys Lys Leu Ile Lys Ala Gly Ser Met Phe Arg Pro Phe Val Pro
            435                 440                 445
Pro Val Val Asn Gly Lys Lys Trp Glu Asp Gly Asp Thr Glu Asp Met
            450                 455                 460
Ala Asn Asn Ile Asp Tyr Trp Arg Phe Glu Lys Gly Ala Lys Trp His
465                 470                 475                 480
Ala Tyr Glu Gly Tyr Gly Asp Asn Gln Tyr Tyr Val Asp Pro Asn Lys
            485                 490                 495
Phe Met Leu Thr Thr Pro Gly Ile Asn Pro Glu Thr Gly Asp Tyr Glu
            500                 505                 510
Asp Phe Gly Val Pro Ala Thr Ile Val Ala Asn Tyr Leu Arg Asp His
            515                 520                 525
Gly Ile Ile Pro Glu Lys Ser Asp Leu Asn Ser Ile Leu Phe Leu Met
            530                 535                 540
Thr Pro Ala Glu Thr Pro Ala Lys Met Asn Asn Leu Ile Thr Gln Leu
545                 550                 555                 560
Leu Gln Leu Gln Arg Leu Ile Glu Glu Asp Ala Pro Leu Lys Gln Val
            565                 570                 575
Leu Pro Ser Ile Tyr Ala Ala Asn Glu Arg Tyr Asn Gly Tyr Thr
            580                 585                 590
Ile Arg Glu Leu Cys Gln Glu Leu His Asp Phe Tyr Lys Asn Asn Asn
            595                 600                 605
```

Thr Phe Thr Tyr Gln Lys Arg Leu Phe Leu Arg Glu Phe Pro Glu
    610                 615                 620

Gln Gly Met Leu Pro Tyr Glu Ala Arg Gln Glu Phe Ile Arg Asn His
625                 630                 635                 640

Asn Lys Leu Val Pro Leu Asn Lys Ile Glu Gly Glu Ile Ala Leu Glu
                645                 650                 655

Gly Ala Leu Pro Tyr Pro Pro Gly Val Phe Cys Val Ala Pro Gly Glu
                660                 665                 670

Lys Trp Ser Glu Thr Ala Val Lys Tyr Phe Thr Ile Leu Gln Asp Gly
                675                 680                 685

Ile Asn Asn Phe Pro Gly Phe Ala Pro Glu Ile Gln Gly Val Tyr Phe
    690                 695                 700

Lys Gln Glu Gly Asp Lys Val Val Arg Tyr Gly Glu Val Tyr Asp Ala
705                 710                 715                 720

Glu Val Ala Lys Asn Asp Asp Arg Tyr Asn Asn
                725                 730

<210> SEQ ID NO 21
<211> LENGTH: 731
<212> TYPE: PRT
<213> ORGANISM: Artificial Sequence
<220> FEATURE:
<223> OTHER INFORMATION: ORNITHINE DECARBOXYLASE MUTANT

<400> SEQUENCE: 21

Met Ser Ser Ser Leu Lys Ile Ala Ser Thr Gln Glu Ala Arg Gln Tyr
1               5                   10                  15

Phe Asp Thr Asp Arg Val Val Asp Ala Val Gly Ser Asp Phe Thr
                20                  25                  30

Asp Val Gly Ala Val Ile Ala Met Asp Tyr Glu Thr Asp Val Ile Asp
            35                  40                  45

Ala Ala Asp Ala Thr Lys Phe Gly Ile Pro Val Phe Ala Val Thr Lys
        50                  55                  60

Asp Ala Gln Ala Ile Ser Ala Asp Glu Leu Lys Lys Ile Phe His Ile
65                  70                  75                  80

Ile Asp Leu Glu Asn Lys Phe Asp Ala Thr Val Asn Ala Arg Glu Ile
                85                  90                  95

Glu Thr Ala Val Asn Asn Tyr Glu Asp Ser Ile Leu Pro Pro Phe Phe
            100                 105                 110

Lys Ser Leu Lys Glu Tyr Val Ser Arg Gly Leu Ile Gln Phe Asp Cys
        115                 120                 125

Pro Gly His Gln Gly Gly Gln Tyr Tyr Arg Lys His Pro Ala Gly Arg
    130                 135                 140

Glu Phe Tyr Asp Phe Phe Gly Glu Thr Val Phe Arg Ala Asp Leu Cys
145                 150                 155                 160

Asn Ala Asp Val Ala Leu Gly Asp Leu Leu Ile His Glu Gly Pro Ala
                165                 170                 175

Val Ala Ala Glu Lys His Ala Ala Arg Val Tyr Asn Ala Asp Lys Thr
            180                 185                 190

Tyr Phe Val Leu Gly Gly Ser Ser Asn Ala Asn Thr Val Thr Ser
        195                 200                 205

Ala Leu Val Ser Asn Gly Asp Leu Val Leu Phe Asp Arg Asn Asn His
    210                 215                 220

Lys Ser Val Tyr Asn Ser Ala Leu Ala Met Ala Gly Gly Arg Pro Val
225                 230                 235                 240

```
Tyr Leu Gln Thr Asn Arg Asn Pro Tyr Gly Phe Ile Gly Ile Tyr
                245                 250                 255

Asp Ser Asp Phe Asp Glu Lys Lys Ile Arg Glu Leu Ala Ala Lys Val
            260                 265                 270

Asp Pro Glu Arg Ala Lys Trp Lys Arg Pro Phe Arg Leu Ala Val Ile
        275                 280                 285

Gln Leu Gly Thr Tyr Asp Gly Thr Ile Tyr Asn Ala His Glu Val Val
    290                 295                 300

Lys Arg Ile Gly His Leu Cys Asp Tyr Ile Glu Phe Asp Ser Ala Trp
305                 310                 315                 320

Val Gly Tyr Glu Gln Phe Ile Pro Met Met Arg Asn Ser Ser Pro Leu
                325                 330                 335

Leu Ile Asp Asp Leu Gly Pro Glu Asp Pro Gly Ile Ile Val Val Gln
            340                 345                 350

Ser Val His Lys Gln Gln Ala Gly Phe Ser Gln Thr Ser Gln Ile His
        355                 360                 365

Lys Lys Asp Ser His Ile Lys Gly Gln Leu Arg Tyr Cys Asp His Lys
    370                 375                 380

His Phe Asn Asn Ser Phe Asn Leu Phe Met Ser Thr Ser Pro Phe Tyr
385                 390                 395                 400

Pro Met Tyr Ala Ala Leu Asp Val Asn Ala Ala Met Gln Glu Gly Glu
                405                 410                 415

Ala Gly Arg Lys Leu Trp His Asp Leu Leu Ile Thr Thr Ile Glu Ala
            420                 425                 430

Arg Lys Lys Leu Ile Lys Ala Gly Ser Met Phe Arg Pro Phe Val Pro
        435                 440                 445

Pro Val Val Asn Gly Lys Lys Trp Glu Asp Gly Asp Thr Glu Asp Met
    450                 455                 460

Ala Asn Asn Ile Asp Tyr Trp Arg Phe Glu Lys Gly Ala Lys Trp His
465                 470                 475                 480

Ala Tyr Glu Gly Tyr Gly Asp Asn Gln Tyr Tyr Val Asp Pro Asn Lys
                485                 490                 495

Phe Met Leu Thr Thr Pro Gly Ile Asn Pro Glu Thr Gly Asp Tyr Glu
            500                 505                 510

Asp Phe Gly Val Pro Ala Thr Ile Val Ala Asn Tyr Leu Arg Asp His
        515                 520                 525

Gly Ile Ile Pro Glu Lys Ser Asp Leu Asn Ser Ile Leu Phe Leu Met
    530                 535                 540

Thr Pro Ala Glu Thr Pro Ala Lys Met Asn Asn Leu Ile Thr Gln Leu
545                 550                 555                 560

Leu Gln Leu Gln Arg Leu Ile Glu Glu Asp Ala Pro Leu Lys Gln Val
                565                 570                 575

Leu Pro Ser Ile Tyr Ala Ala Asn Glu Glu Arg Tyr Asn Gly Tyr Thr
            580                 585                 590

Ile Arg Glu Leu Cys Gln Glu Leu His Asp Phe Tyr Lys Asn Asn Asn
        595                 600                 605

Thr Phe Thr Tyr Gln Lys Arg Leu Phe Leu Arg Glu Phe Phe Pro Glu
    610                 615                 620

Gln Gly Met Leu Pro Tyr Glu Ala Arg Gln Glu Phe Ile Arg Asn His
625                 630                 635                 640

Asn Lys Leu Val Pro Leu Asn Lys Ile Glu Gly Glu Ile Ala Leu Glu
                645                 650                 655
```

```
Gly Ala Leu Pro Tyr Pro Pro Gly Val Phe Cys Val Ala Pro Gly Glu
                660                 665                 670

Lys Trp Ser Glu Thr Ala Val Lys Tyr Phe Thr Ile Leu Gln Asp Gly
675                 680                 685

Ile Asn Asn Phe Pro Gly Phe Ala Pro Glu Ile Gln Gly Val Tyr Phe
        690                 695                 700

Lys Gln Glu Gly Asp Lys Val Asp Tyr Gly Val Tyr Asp Ala
705                 710                 715                 720

Glu Val Ala Lys Asn Asp Asp Arg Tyr Asn Asn
                725                 730
```

<210> SEQ ID NO 22
<211> LENGTH: 731
<212> TYPE: PRT
<213> ORGANISM: Artificial Sequence
<220> FEATURE:
<223> OTHER INFORMATION: ORNITHINE DECARBOXYLASE MUTANT

<400> SEQUENCE: 22

```
Met Ser Ser Ser Leu Lys Ile Ala Ser Thr Gln Glu Ala Arg Gln Tyr
1               5                   10                  15

Phe Asp Thr Asp Arg Val Val Val Asp Ala Val Gly Ser Asp Phe Thr
                20                  25                  30

Asp Val Gly Ala Val Ile Ala Met Asp Tyr Glu Thr Asp Val Ile Asp
            35                  40                  45

Ala Ala Asp Ala Thr Lys Phe Gly Ile Pro Val Phe Ala Val Thr Lys
        50                  55                  60

Asp Ala Gln Ala Ile Ser Ala Asp Glu Leu Lys Lys Ile Phe His Ile
65                  70                  75                  80

Ile Asp Leu Glu Asn Lys Phe Asp Ala Thr Val Asn Ala Arg Glu Ile
                85                  90                  95

Glu Thr Ala Val Asn Asn Tyr Glu Asp Ser Ile Leu Pro Pro Phe Phe
            100                 105                 110

Lys Ser Leu Lys Glu Tyr Val Ser Arg Gly Leu Ile Gln Phe Asp Cys
        115                 120                 125

Pro Gly His Gln Gly Gly Gln Tyr Tyr Arg Lys His Pro Ala Gly Arg
130                 135                 140

Glu Phe Tyr Asp Phe Phe Gly Glu Thr Val Phe Arg Ala Asp Leu Cys
145                 150                 155                 160

Asn Ala Asp Val Ala Leu Gly Asp Leu Leu Ile His Glu Gly Pro Ala
                165                 170                 175

Val Ala Ala Glu Lys His Ala Ala Arg Val Tyr Asn Ala Asp Lys Thr
            180                 185                 190

Tyr Phe Val Leu Gly Gly Ser Ser Asn Ala Asn Asn Thr Val Thr Ser
        195                 200                 205

Ala Leu Val Ser Asn Gly Asp Leu Val Leu Phe Asp Arg Asn Asn His
    210                 215                 220

Lys Ser Val Tyr Asn Ser Ala Leu Ala Met Ala Gly Gly Arg Pro Val
225                 230                 235                 240

Tyr Leu Gln Thr Asn Arg Asn Pro Tyr Gly Phe Ile Gly Gly Ile Tyr
                245                 250                 255

Asp Ser Asp Phe Asp Glu Lys Lys Ile Arg Glu Leu Ala Ala Lys Val
            260                 265                 270

Asp Pro Glu Arg Ala Lys Trp Lys Arg Pro Phe Arg Leu Ala Val Ile
        275                 280                 285
```

```
Gln Leu Gly Thr Tyr Asp Gly Thr Ile Tyr Asn Ala His Glu Val Val
    290                 295                 300

Lys Arg Ile Gly His Leu Cys Asp Tyr Ile Glu Phe Asp Ser Ala Trp
305                 310                 315                 320

Val Gly Tyr Glu Gln Phe Ile Pro Met Met Arg Asn Ser Ser Pro Leu
                325                 330                 335

Leu Ile Asp Asp Leu Gly Pro Glu Asp Pro Gly Ile Ile Val Val Gln
                340                 345                 350

Ser Val His Lys Gln Gln Ala Gly Phe Ser Gln Thr Ser Gln Ile His
        355                 360                 365

Lys Lys Asp Ser His Ile Lys Gly Gln Leu Arg Tyr Cys Asp His Lys
370                 375                 380

His Phe Asn Asn Ser Phe Asn Leu Phe Met Ser Thr Ser Pro Phe Tyr
385                 390                 395                 400

Pro Met Tyr Ala Ala Leu Asp Val Asn Ala Ala Met Gln Glu Gly Glu
                405                 410                 415

Ala Gly Arg Lys Leu Trp His Asp Leu Leu Ile Thr Thr Ile Glu Ala
            420                 425                 430

Arg Lys Lys Leu Ile Lys Ala Gly Ser Met Phe Arg Pro Phe Val Pro
            435                 440                 445

Pro Val Val Asn Gly Lys Lys Trp Glu Asp Gly Asp Thr Glu Asp Met
450                 455                 460

Ala Asn Asn Ile Asp Tyr Trp Arg Phe Glu Lys Gly Ala Lys Trp His
465                 470                 475                 480

Ala Tyr Glu Gly Tyr Gly Asp Asn Gln Tyr Tyr Val Asp Pro Asn Lys
                485                 490                 495

Phe Met Leu Thr Thr Pro Gly Ile Asn Pro Glu Thr Gly Asp Tyr Glu
                500                 505                 510

Asp Phe Gly Val Pro Ala Thr Ile Val Ala Asn Tyr Leu Arg Asp His
            515                 520                 525

Gly Ile Ile Pro Glu Lys Ser Asp Leu Asn Ser Ile Leu Phe Leu Met
530                 535                 540

Thr Pro Ala Glu Thr Pro Ala Lys Met Asn Asn Leu Ile Thr Gln Leu
545                 550                 555                 560

Leu Gln Leu Gln Arg Leu Ile Glu Glu Asp Ala Pro Leu Lys Gln Val
                565                 570                 575

Leu Pro Ser Ile Tyr Ala Ala Asn Glu Glu Arg Tyr Asn Gly Tyr Thr
                580                 585                 590

Ile Arg Glu Leu Cys Gln Glu Leu His Asp Phe Tyr Lys Asn Asn Asn
            595                 600                 605

Thr Phe Thr Tyr Gln Lys Arg Leu Phe Leu Arg Glu Phe Phe Pro Glu
            610                 615                 620

Gln Gly Met Leu Pro Tyr Glu Ala Arg Gln Glu Phe Ile Arg Asn His
625                 630                 635                 640

Asn Lys Leu Val Pro Leu Asn Lys Ile Glu Gly Glu Ile Ala Leu Glu
                645                 650                 655

Gly Ala Leu Pro Tyr Pro Pro Gly Val Phe Cys Val Ala Pro Gly Glu
                660                 665                 670

Lys Trp Ser Glu Thr Ala Val Lys Tyr Phe Thr Ile Leu Gln Asp Gly
            675                 680                 685

Ile Asn Asn Phe Pro Gly Phe Ala Pro Glu Ile Gln Gly Val Tyr Phe
690                 695                 700

Lys Gln Glu Gly Asp Lys Val Val Trp Tyr Gly Glu Val Tyr Asp Ala
```

```
                705                 710                 715                 720
            Glu Val Ala Lys Asn Asp Asp Arg Tyr Asn Asn
                                725                 730

<210> SEQ ID NO 23
<211> LENGTH: 731
<212> TYPE: PRT
<213> ORGANISM: Artificial Sequence
<220> FEATURE:
<223> OTHER INFORMATION: ORNITHINE DECARBOXYLASE MUTANT

<400> SEQUENCE: 23

Met Ser Ser Ser Leu Lys Ile Ala Ser Thr Gln Glu Ala Arg Gln Tyr
1               5                   10                  15

Phe Asp Thr Asp Arg Val Val Asp Ala Val Gly Ser Asp Phe Thr
            20                  25                  30

Asp Val Gly Ala Val Ile Ala Met Asp Tyr Glu Thr Asp Val Ile Asp
        35                  40                  45

Ala Ala Asp Ala Thr Lys Phe Gly Ile Pro Val Phe Ala Val Thr Lys
    50                  55                  60

Asp Ala Gln Ala Ile Ser Ala Asp Glu Leu Lys Lys Ile Phe His Ile
65                  70                  75                  80

Ile Asp Leu Glu Asn Lys Phe Asp Ala Thr Val Asn Ala Arg Glu Ile
                85                  90                  95

Glu Thr Ala Val Asn Asn Tyr Glu Asp Ser Ile Leu Pro Pro Phe Phe
            100                 105                 110

Lys Ser Leu Lys Glu Tyr Val Ser Arg Gly Leu Ile Gln Phe Asp Cys
        115                 120                 125

Pro Gly His Gln Gly Gln Tyr Tyr Arg Lys His Pro Ala Gly Arg
    130                 135                 140

Glu Phe Tyr Asp Phe Phe Gly Glu Thr Val Phe Arg Ala Asp Leu Cys
145                 150                 155                 160

Asn Ala Asp Val Ala Leu Gly Asp Leu Leu Ile His Glu Gly Pro Ala
                165                 170                 175

Val Ala Ala Glu Lys His Ala Ala Arg Val Tyr Asn Ala Asp Lys Thr
            180                 185                 190

Tyr Phe Val Leu Gly Gly Ser Ser Asn Ala Asn Asn Thr Val Thr Ser
        195                 200                 205

Ala Leu Val Ser Asn Gly Asp Leu Val Leu Phe Asp Arg Asn Asn His
    210                 215                 220

Lys Ser Val Tyr Asn Ser Ala Leu Ala Met Ala Gly Gly Arg Pro Val
225                 230                 235                 240

Tyr Leu Gln Thr Asn Arg Asn Pro Tyr Gly Phe Ile Gly Gly Ile Tyr
                245                 250                 255

Asp Ser Asp Phe Asp Glu Lys Lys Ile Arg Glu Leu Ala Ala Lys Val
            260                 265                 270

Asp Pro Glu Arg Ala Lys Trp Lys Arg Pro Phe Arg Leu Ala Val Ile
        275                 280                 285

Gln Leu Gly Thr Tyr Asp Gly Thr Ile Tyr Asn Ala His Glu Val Val
    290                 295                 300

Lys Arg Ile Gly His Leu Cys Asp Tyr Ile Glu Phe Asp Ser Ala Trp
305                 310                 315                 320

Val Gly Tyr Glu Gln Phe Ile Pro Met Met Arg Asn Ser Ser Pro Leu
                325                 330                 335

Leu Ile Asp Asp Leu Gly Pro Glu Asp Pro Gly Ile Ile Val Val Gln
```

-continued

```
            340                 345                 350
Ser Val His Lys Gln Ala Gly Phe Ser Gln Thr Ser Gln Ile His
            355                 360                 365
Lys Lys Asp Ser His Ile Lys Gly Gln Leu Arg Tyr Cys Asp His Lys
    370                 375                 380
His Phe Asn Asn Ser Phe Asn Leu Phe Met Ser Thr Ser Pro Phe Tyr
385                 390                 395                 400
Pro Met Tyr Ala Ala Leu Asp Val Asn Ala Ala Met Gln Glu Gly Glu
                405                 410                 415
Ala Gly Arg Lys Leu Trp His Asp Leu Leu Ile Thr Thr Ile Glu Ala
            420                 425                 430
Arg Lys Lys Leu Ile Lys Ala Gly Ser Met Phe Arg Pro Phe Val Pro
        435                 440                 445
Pro Val Val Asn Gly Lys Lys Trp Glu Asp Gly Asp Thr Glu Asp Met
    450                 455                 460
Ala Asn Asn Ile Asp Tyr Trp Arg Phe Glu Lys Gly Ala Lys Trp His
465                 470                 475                 480
Ala Tyr Glu Gly Tyr Gly Asp Asn Gln Tyr Tyr Val Asp Pro Asn Lys
                485                 490                 495
Phe Met Leu Thr Thr Pro Gly Ile Asn Pro Glu Thr Gly Asp Tyr Glu
            500                 505                 510
Asp Phe Gly Val Pro Ala Thr Ile Val Ala Asn Tyr Leu Arg Asp His
        515                 520                 525
Gly Ile Ile Pro Glu Lys Ser Asp Leu Asn Ser Ile Leu Phe Leu Met
    530                 535                 540
Thr Pro Ala Glu Thr Pro Ala Lys Met Asn Asn Leu Ile Thr Gln Leu
545                 550                 555                 560
Leu Gln Leu Gln Arg Leu Ile Glu Glu Asp Ala Pro Leu Lys Gln Val
                565                 570                 575
Leu Pro Ser Ile Tyr Ala Ala Asn Glu Glu Arg Tyr Asn Gly Tyr Thr
            580                 585                 590
Ile Arg Glu Leu Cys Gln Glu Leu His Asp Phe Tyr Lys Asn Asn Asn
        595                 600                 605
Thr Phe Thr Tyr Gln Lys Arg Leu Phe Leu Arg Glu Phe Phe Pro Glu
    610                 615                 620
Gln Gly Met Leu Pro Tyr Glu Ala Arg Gln Glu Phe Ile Arg Asn His
625                 630                 635                 640
Asn Lys Leu Val Pro Leu Asn Lys Ile Glu Gly Glu Ile Ala Leu Glu
                645                 650                 655
Gly Ala Leu Pro Tyr Pro Pro Gly Val Phe Cys Val Ala Pro Gly Glu
            660                 665                 670
Lys Trp Ser Glu Thr Ala Val Lys Tyr Phe Thr Ile Leu Gln Asp Gly
        675                 680                 685
Ile Asn Asn Phe Pro Gly Phe Ala Pro Glu Ile Gln Gly Val Tyr Phe
    690                 695                 700
Lys Gln Glu Gly Asp Lys Val Val Gln Tyr Gly Glu Val Tyr Asp Ala
705                 710                 715                 720
Glu Val Ala Lys Asn Asp Asp Arg Tyr Asn Asn
                725                 730

<210> SEQ ID NO 24
<211> LENGTH: 2196
<212> TYPE: DNA
<213> ORGANISM: Artificial Sequence
```

<220> FEATURE:
<223> OTHER INFORMATION: A DNA encoding a amino acid sequences of SEQ ID NO.19

<400> SEQUENCE: 24

| | | | | | |
|---|---|---|---|---|---:|
| atgagttctt | ctcttaaaat | tgcttcgact | caagaagcgc | gtcaatattt cgatactgac | 60 |
| cgcgttgttg | tcgatgctgt | aggctctgat | tttactgatg | tcggtgctgt tatcgcaatg | 120 |
| gattacgaaa | cagatgtcat | cgacgctgct | gatgcaacta | agtttggtat tcctgttttt | 180 |
| gccgtaacta | aggatgccca | agctatcagt | gctgatgagc | tgaagaagat tttccacatc | 240 |
| attgatttgg | aaaacaaatt | tgatgctact | gttaacgctc | gtgaaatcga aactgctgtt | 300 |
| aacaactacg | aagacagcat | tttaccacca | ttcttcaagt | cattgaaaga atacgttagc | 360 |
| cgtggtttaa | tccaattcga | ctgcccaggt | caccaaggtg | tcaatacta cagaaagcac | 420 |
| ccagctggtc | gtgaattcta | cgacttcttc | ggcgaaactg | tcttccgtgc agacttatgt | 480 |
| aacgctgacg | ttgccttggg | tgacttgctg | atccacgaag | gtcctgctgt tgctgctgaa | 540 |
| aagcatgctg | cacgtgttta | caacgctgac | aagacttact | tcgttttagg tggttcttcc | 600 |
| aacgctaaca | acactgtaac | atctgcttta | gttctaacg | gcgacttggt attgttcgac | 660 |
| cggaacaacc | acaagtccgt | ttacaactca | gctttagcta | tggctggtgg ccgtcctgtt | 720 |
| tacctccaaa | caaaccgtaa | cccatacggc | ttcatcggtg | gtatctacga cagcgacttc | 780 |
| gatgaaaaga | agatccgtga | actggcagct | aaggttgacc | agaacgtgc taagtggaag | 840 |
| cgtccattcc | gtctggctgt | tatccaatta | ggtacttacg | atggtactat ctacaacgca | 900 |
| cacgaagttg | taaagcgtat | cggtcacctt | tgtgattaca | tcgaattcga ctctgcttgg | 960 |
| gtaggttacg | aacaattcat | tcctatgatg | cgtaactctt | caccattatt gattgatgac | 1020 |
| cttggtccag | aagatcctgg | tatcattgtt | gttcaatcag | ttcacaagca acaagccggc | 1080 |
| ttctcacaaa | cttcacaaat | ccacaagaag | gatagccaca | tcaagggtca attacgttac | 1140 |
| tgtgaccaca | agcactttaa | caactccttc | aacttgttca | tgtctacttc accattctac | 1200 |
| ccaatgtatg | cagcattaga | cgttaacgct | gctatgcaag | aaggcgaagc aggtcgcaag | 1260 |
| ttatggcatg | accttctgat | tactaccatt | gaagctcgta | agaagttgat caaggctggc | 1320 |
| tcaatgttcc | gtccattcgt | tccacctgtt | gttaacggca | agaagtggga agatggcgac | 1380 |
| actgaagata | tggctaacaa | cattgactac | tggcgctttg | aaaagggtgc taagtggcat | 1440 |
| gcttacgaag | gctacggcga | caaccaatac | tacgttgatc | caaacaagtt catgttaact | 1500 |
| acacctggta | tcaacccaga | aactggtgac | tacgaagact | tcggtgttcc agctactatc | 1560 |
| gttgctaact | acttacgtga | ccacggtatc | atccctgaaa | agtctgactt gaactctatc | 1620 |
| ttgttcttga | tgactccagc | tgaaactcca | gctaagatga | caacctgat cactcaactt | 1680 |
| cttcaattac | aacgcttgat | cgaagaagat | gctccattga | agcaagttct tccttcaatc | 1740 |
| tacgctgcta | acgaagaacg | ttacaatggc | tacactatcc | gtgaacttg ccaagaattg | 1800 |
| cacgacttct | acaagaacaa | caacacgttc | acataccaga | agcgtctctt cttacgtgaa | 1860 |
| ttcttcccag | aacaaggtat | gcttccatac | gaagctcgtc | aagaattcat ccgcaaccac | 1920 |
| aacaagcttt | tccattgaa | caagatcgaa | ggcgaaatcg | ccctcgaagg tgctcttcca | 1980 |
| taccctccag | gagtattctg | tgtagcacca | ggtgaaaagt | ggtcagaaac tgctgttaag | 2040 |
| tacttcacta | tcttacaaga | tggtatcaac | aacttccctg | gattcgctcc agaaatccaa | 2100 |
| ggtgtatact | tcaagcaaga | aggcgacaag | gttgttgtgt | acggtgaagt ttacgatgca | 2160 |
| gaagttgcta | agaacgatga | tcgttacaac | aactaa | | 2196 |

<210> SEQ ID NO 25
<211> LENGTH: 2196
<212> TYPE: DNA
<213> ORGANISM: Artificial Sequence
<220> FEATURE:
<223> OTHER INFORMATION: A DNA encoding a amino acid sequences of SEQ ID
      NO.20

<400> SEQUENCE: 25

| | | | | | |
|---|---|---|---|---|---|
| atgagttctt | ctcttaaaat | tgcttcgact | caagaagcgc | gtcaatattt | cgatactgac | 60 |
| cgcgttgttg | tcgatgctgt | aggctctgat | tttactgatg | tcggtgctgt | tatcgcaatg | 120 |
| gattacgaaa | cagatgtcat | cgacgctgct | gatgcaacta | agtttggtat | tcctgttttt | 180 |
| gccgtaacta | aggatgccca | agctatcagt | gctgatgagc | tgaagaagat | tttccacatc | 240 |
| attgatttgg | aaaacaaatt | tgatgctact | gttaacgctc | gtgaaatcga | aactgctgtt | 300 |
| aacaactacg | aagacagcat | tttaccacca | ttcttcaagt | cattgaaaga | atacgttagc | 360 |
| cgtggtttaa | tccaattcga | ctgcccaggt | caccaaggtg | tcaatacta | cagaaagcac | 420 |
| ccagctggtc | gtgaattcta | cgacttcttc | ggcgaaactg | tcttccgtgc | agacttatgt | 480 |
| aacgctgacg | ttgccttggg | tgacttgctg | atccacgaag | gtcctgctgt | tgctgctgaa | 540 |
| aagcatgctg | cacgtgttta | caacgctgac | aagacttact | tcgttttagg | tggttcttcc | 600 |
| aacgctaaca | cactgtaac | atctgcttta | gtttctaacg | gcgacttggt | attgttcgac | 660 |
| cggaacaacc | acaagtccgt | ttacaactca | gctttagcta | tggctggtgg | ccgtcctgtt | 720 |
| tacctccaaa | caaaccgtaa | cccatacggc | ttcatcggtg | tatctacga | cagcgacttc | 780 |
| gatgaaaaga | agatccgtga | actggcagct | aaggttgacc | agaacgtgc | taagtggaag | 840 |
| cgtccattcc | gtctggctgt | tatccaatta | ggtacttacg | atggtactat | ctacaacgca | 900 |
| cacgaagttg | taaagcgtat | cggtcacctt | tgtgattaca | tcgaattcga | ctctgcttgg | 960 |
| gtaggttacg | aacaattcat | tcctatgatg | cgtaactctt | caccattatt | gattgatgac | 1020 |
| cttggtccag | aagatcctgg | tatcattgtt | gttcaatcag | ttcacaagca | acaagccggc | 1080 |
| ttctcacaaa | cttcacaaat | ccacaagaag | gatagccaca | tcaagggtca | attacgttac | 1140 |
| tgtgaccaca | agcactttaa | caactccttc | aacttgttca | tgtctacttc | accattctac | 1200 |
| ccaatgtatg | cagcattaga | cgttaacgct | gctatgcaag | aaggcgaagc | aggtcgcaag | 1260 |
| ttatggcatg | accttctgat | tactaccatt | gaagctcgta | agaagttgat | caaggctggc | 1320 |
| tcaatgttcc | gtccattcgt | tccacctgtt | gttaacggca | gaagtggga | agatggcgac | 1380 |
| actgaagata | tggctaacaa | cattgactac | tggcgctttg | aaaagggtgc | taagtggcat | 1440 |
| gcttacgaag | gctacggcga | caaccaatac | tacgttgatc | aaacaagtt | catgttaact | 1500 |
| acacctggta | tcaacccaga | aactggtgac | tacgaagact | tcggtgttcc | agctactatc | 1560 |
| gttgctaact | acttacgtga | ccacggtatc | atccctgaaa | agtctgactt | gaactctatc | 1620 |
| ttgttcttga | tgactccagc | tgaaactcca | gctaagatga | caacctgat | cactcaactt | 1680 |
| cttcaattac | aacgcttgat | cgaagaagat | gctccattga | agcaagttct | tccttcaatc | 1740 |
| tacgctgcta | acgaagaacg | ttacaatggc | tacactatcc | gtgaactttg | ccaagaattg | 1800 |
| cacgacttct | acaagaacaa | caacacgttc | acataccaga | agcgtctctt | cttacgtgaa | 1860 |
| ttcttcccag | aacaaggtat | gcttccatac | gaagctcgtc | aagaattcat | ccgcaaccac | 1920 |
| aacaagcttt | tccattgaa | caagatcgaa | ggcgaaatcg | ccctcgaagg | tgctcttcca | 1980 |
| taccctccag | gagtattctg | tgtagcacca | ggtgaaaagt | ggtcagaaac | tgctgttaag | 2040 |

```
tacttcacta tcttacaaga tggtatcaac aacttccctg gattcgctcc agaaatccaa    2100
ggtgtatact tcaagcaaga aggcgacaag gttgttaggt acggtgaagt ttacgatgca    2160
gaagttgcta agaacgatga tcgttacaac aactaa                              2196
```

<210> SEQ ID NO 26
<211> LENGTH: 2196
<212> TYPE: DNA
<213> ORGANISM: Artificial Sequence
<220> FEATURE:
<223> OTHER INFORMATION: A DNA encoding a amino acid sequences of SEQ ID
      NO.21

<400> SEQUENCE: 26

```
atgagttctt ctcttaaaat tgcttcgact caagaagcgc gtcaatattt cgatactgac     60
cgcgttgttg tcgatgctgt aggctctgat tttactgatg tcggtgctgt tatcgcaatg    120
gattacgaaa cagatgtcat cgacgctgct gatgcaacta gtttggtat tcctgttttt    180 gccgtaacta aggatgccca agctatcagt gctgatgagc tgaagaagat tttccacatc    240
attgatttgg aaaacaaatt tgatgctact gttaacgctc gtgaaatcga aactgctgtt    300
aacaactacg aagacagcat tttaccacca ttcttcaagt cattgaaaga atacgttagc    360
cgtggtttaa tccaattcga ctgcccaggt caccaaggtg gtcaatacta cagaaagcac    420
ccagctggtc gtgaattcta cgacttcttc ggcgaaactg tcttccgtgc agacttatgt    480
aacgctgacg ttgccttggg tgacttgctg atccacgaag gtcctgctgt tgctgctgaa    540
aagcatgctg cacgtgttta caacgctgac aagacttact cgttttagg tggttcttcc    600 aacgctaaca acactgtaac atctgcttta gtttctaacg gcgacttggt attgttcgac    660
cggaacaacc acaagtccgt ttacaactca gctttagcta tggctggtgg ccgtcctgtt    720
tacctccaaa caaaccgtaa cccatacggc ttcatcggtg gtatctacga cagcgacttc    780
gatgaaaaga gatccgtga actggcagct aaggttgacc cagaacgtgc taagtggaag    840
cgtccattcc gtctggctgt tatccaatta ggtacttacg atggtactat ctacaacgca    900
cacgaagttg taaagcgtat cggtcacctt tgtgattaca tcgaattcga ctctgcttgg    960
gtaggttacg acaattcat tcctatgatg cgtaactctt caccattatt gattgatgac    1020
cttggtccag aagatcctgg tatcattgtt gttcaatcag ttcacaagca acaagccggc    1080
ttctcacaaa cttcacaaat ccacaagaag gatagccaca tcaagggtca attacgttac    1140
tgtgaccaca agcactttaa caactccttc aacttgttca tgtctacttc accattctac    1200
ccaatgtatg cagcattaga cgttaacgct gctatgcaag aaggcgaagc aggtcgcaag    1260
ttatggcatg accttctgat tactaccatt gaagctcgta agaagttgat caaggctggc    1320
tcaatgttcc gtccattcgt tccacctgtt gttaacggca agaagtggga agatggcgac    1380
actgaagata tggctaacaa cattgactac tggcgctttg aaaagggtgc taagtggcat    1440
gcttacgaag gctacggcga caaccaatac acgttgatc aaacaagtt catgttaact    1500 acacctggta tcaacccaga aactggtgac tacgaagact tcggtgttcc agctactatc    1560
gttgctaact acttacgtga ccacggtatc atccctgaaa agtctgactt gaactctatc    1620
ttgttcttga tgactccagc tgaaactcca gctaagatga caacctgat cactcaactt    1680 cttcaattac aacgcttgat cgaagaagat gctccattga agcaagttct tccttcaatc    1740
tacgctgcta acgaagaacg ttacaatggc tacactatcc gtgaactttg ccaagaattg    1800
cacgacttct acaagaacaa caacacgttc acataccaga agcgtctctt cttacgtgaa    1860
```

```
ttcttcccag aacaaggtat gcttccatac gaagctcgtc aagaattcat ccgcaaccac    1920
aacaagcttg ttccattgaa caagatcgaa ggcgaaatcg ccctcgaagg tgctcttcca    1980
taccctccag gagtattctg tgtagcacca ggtgaaaagt ggtcagaaac tgctgttaag    2040
tacttcacta tcttacaaga tggtatcaac aacttccctg gattcgctcc agaaatccaa    2100
ggtgtatact tcaagcaaga aggcgacaag gttgttgact acggtgaagt ttacgatgca    2160
gaagttgcta gaacgatga tcgttacaac aactaa                              2196
```

<210> SEQ ID NO 27
<211> LENGTH: 2196
<212> TYPE: DNA
<213> ORGANISM: Artificial Sequence
<220> FEATURE:
<223> OTHER INFORMATION: A DNA encoding a amino acid sequences of SEQ ID NO.22

<400> SEQUENCE: 27

```
atgagttctt ctcttaaaat tgcttcgact caagaagcgc gtcaatattt cgatactgac     60
cgcgttgttg tcgatgctgt aggctctgat tttactgatg tcggtgctgt tatcgcaatg    120
gattacgaaa cagatgtcat cgacgctgct gatgcaacta agtttggtat tcctgttttt    180
gccgtaacta aggatgccca agctatcagt gctgatgagc tgaagaagat tttccacatc    240
attgatttgg aaaacaaatt tgatgctact gttaacgctc gtgaaatcga actgctgtt     300 aacaactacg aagacagcat tttaccacca ttcttcaagt cattgaaaga atacgttagc    360
cgtggtttaa tccaattcga ctgcccaggt caccaaggtg gtcaatacta cagaaagcac    420
ccagctggtc gtgaattcta cgacttcttc ggcgaaactg tcttccgtgc agacttatgt    480
aacgctgacg ttgccttggg tgacttgctg atccacgaag gtcctgctgt tgctgctgaa    540
aagcatgctg cacgtgttta caacgctgac aagacttact tcgttttagg tggttcttcc    600
aacgctaaca cactgtaac atctgcttta gtttctaacg gcgacttggt attgttcgac    660
cggaacaacc acaagtccgt ttacaactca gctttagcta tggctggtgg ccgtcctgtt    720
tacctccaaa caaaccgtaa cccatacggc ttcatcggtg gtatctacga cagcgacttc    780
gatgaaaaga gatccgtga actggcagct aaggttgacc agaacgtgc taagtggaag     840 cgtccattcc gtctggctgt tatccaatta ggtacttacg atggtactat ctacaacgca    900
cacgaagttg taaagcgtat cggtcacctt tgtgattaca tcgaattcga ctctgcttgg    960
gtaggttacg aacaattcat tcctatgatg cgtaactctt caccattatt gattgatgac   1020
cttggtccag aagatcctgg tatcattgtt gttcaatcag ttcacaagca acaagccggc   1080
ttctcacaaa cttcacaaat ccacaagaag gatagccaca tcaagggtca attacgttac   1140
tgtgaccaca agcactttaa caactccttc aacttgttca tgtctacttc accattctac   1200
ccaatgtatg cagcattaga cgttaacgct gctatgcaag aaggcgaagc aggtcgcaag   1260
ttatggcatg accttctgat tactaccatt gaagctcgta agaagttgat caaggctggc   1320
tcaatgttcc gtccattcgt tccacctgtt gttaacggca agaagtggga agatggcgac   1380
actgaagata tggctaacaa cattgactac tggcgctttg aaaagggtgc taagtggcat   1440
gcttacgaag gctacggcga caaccaatac tacgttgatc aaacaagtt catgttaact    1500 acacctggta tcaacccaga aactggtgac tacgaagact tcggtgttcc agctactatc   1560
gttgctaact acttacgtga ccacggtatc atccctgaaa agtctgactt gaactctatc   1620
ttgttcttga tgactccagc tgaaactcca gctaagatga acaacctgat cactcaactt   1680
```

```
cttcaattac aacgcttgat cgaagaagat gctccattga agcaagttct tccttcaatc    1740
tacgctgcta acgaagaacg ttacaatggc tacactatcc gtgaactttg ccaagaattg    1800
cacgacttct acaagaacaa caacacgttc acataccaga agcgtctctt cttacgtgaa    1860
ttcttcccag aacaaggtat gcttccatac gaagctcgtc aagaattcat ccgcaaccac    1920
aacaagcttg ttccattgaa caagatcgaa ggcgaaatcg ccctcgaagg tgctcttcca    1980
taccctccag gagtattctg tgtagcacca ggtgaaaagt ggtcagaaac tgctgttaag    2040
tacttcacta tcttacaaga tggtatcaac aacttccctg gattcgctcc agaaatccaa    2100
ggtgtatact tcaagcaaga aggcgacaag gttgtttggt acggtgaagt ttacgatgca    2160
gaagttgcta agaacgatga tcgttacaac aactaa                             2196
```

<210> SEQ ID NO 28
<211> LENGTH: 2196
<212> TYPE: DNA
<213> ORGANISM: Artificial Sequence
<220> FEATURE:
<223> OTHER INFORMATION: A DNA encoding a amino acid sequences of SEQ ID
      NO.23

<400> SEQUENCE: 28

```
atgagttctt ctcttaaaat tgcttcgact caagaagcgc gtcaatattt cgatactgac     60
cgcgttgttg tcgatgctgt aggctctgat tttactgatg tcggtgctgt tatcgcaatg    120
gattacgaaa cagatgtcat cgacgctgct gatgcaacta agtttggtat tcctgttttt    180
gccgtaacta aggatgccca agctatcagt gctgatgagc tgaagaagat tttccacatc    240
attgatttgg aaaacaaatt tgatgctact gttaacgctc gtgaaatcga actgctgtt     300 aacaactacg aagacagcat tttaccacca ttcttcaagt cattgaaaga atacgttagc    360
cgtggtttaa tccaattcga ctgcccaggt caccaaggtg gtcaatacta cagaaagcac    420
ccagctggtc gtgaattcta cgacttcttc ggcgaaactg tcttccgtgc agacttatgt    480
aacgctgacg ttgccttggg tgacttgctg atccacgaag gtcctgctgt gctgctgaa     540 aagcatgctg cacgtgttta caacgctgac aagacttact tcgttttagg tggttcttcc    600
aacgctaaca acactgtaac atctgcttta gtttctaacg gcgacttggt attgttcgac    660
cggaacaacc acaagtccgt ttacaactca gctttagcta tggctggtgg ccgtcctgtt    720
tacctccaaa caaaccgtaa cccatacggc ttcatcggtg gtatctacga cagcgacttc    780
gatgaaaaga agatccgtga actggcagct aaggttgacc agaacgtgc taagtggaag     840 cgtccattcc gtctggctgt tatccaatta ggtacttacg atggtactat ctacaacgca    900
cacgaagttg taaagcgtat cggtcacctt tgtgattaca tcgaattcga ctctgcttgg    960
gtaggttacg aacaattcat tcctatgatg cgtaactctt caccattatt gattgatgac   1020
cttggtccag aagatcctgg tatcattgtt gttcaatcag ttcacaagca acaagccggc   1080
ttctcacaaa cttcacaaat ccacaagaag gatagccaca tcaagggtca attacgttac   1140
tgtgaccaca agcactttaa caactccttc aacttgttca tgtctacttc accattctac   1200
ccaatgtatg cagcattaga cgttaacgct gctatgcaag aaggcgaagc aggtcgcaag   1260
ttatggcatg accttctgat tactaccatt gaagctcgta agaagttgat caaggctggc   1320
tcaatgttcc gtccattcgt tccacctgtt gttaacggca agaagtggga agatggcgac   1380
actgaagata tggctaacaa cattgactac tggcgctttg aaaagggtgc taagtggcat   1440
gcttacgaag gctacggcga caaccaatac tacgttgatc caaacaagtt catgttaact   1500
```

```
acacctggta tcaacccaga aactggtgac tacgaagact tcggtgttcc agctactatc    1560
gttgctaact acttacgtga ccacggtatc atccctgaaa agtctgactt gaactctatc    1620
ttgttcttga tgactccagc tgaaactcca gctaagatga acaacctgat cactcaactt    1680
cttcaattac aacgcttgat cgaagaagat gctccattga agcaagttct tccttcaatc    1740
tacgctgcta acgaagaacg ttacaatggc tacactatcc gtgaactttg ccaagaattg    1800
cacgacttct acaagaacaa caacacgttc ataccaga agcgtctctt cttacgtgaa      1860
ttcttcccag aacaaggtat gcttccatac gaagctcgtc aagaattcat ccgcaaccac    1920
aacaagcttg ttccattgaa caagatcgaa ggcgaaatcg ccctcgaagg tgctcttcca    1980
taccctccag gagtattctg tgtagcacca ggtgaaaagt ggtcagaaac tgctgttaag    2040
tacttcacta tcttacaaga tggtatcaac aacttccctg gattcgctcc agaaatccaa    2100
ggtgtatact tcaagcaaga aggcgacaag gttgttcaat acggtgaagt ttacgatgca    2160
gaagttgcta agaacgatga tcgttacaac aactaa                             2196
```